(12) United States Patent
Huitema et al.

(10) Patent No.: US 8,371,491 B2
(45) Date of Patent: Feb. 12, 2013

(54) SURGICAL END EFFECTOR HAVING BUTTRESS RETENTION FEATURES

(75) Inventors: Thomas W. Huitema, Cincinnati, OH (US); Frederick E. Shelton, IV, Hillsboro, OH (US); Jeffrey S. Swayze, Hamilton, OH (US); Jerome R. Morgan, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 191 days.

(21) Appl. No.: 12/032,002

(22) Filed: Feb. 15, 2008

(65) Prior Publication Data

US 2009/0206143 A1 Aug. 20, 2009

(51) Int. Cl.
*A61B 17/072* (2006.01)

(52) U.S. Cl. ............... 227/176.1; 227/175.1; 227/19

(58) Field of Classification Search .......... 227/175, 227/1–182.1, 19; 606/154, 151
See application file for complete search history.

(56) References Cited

U.S. PATENT DOCUMENTS

| | | | |
|---|---|---|---|
| 2,853,074 A | 9/1958 | Olson | |
| 3,490,675 A | 1/1970 | Green et al. | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| RE28,932 E | 8/1976 | Noiles et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,414 A | 3/1985 | Filipi | |
| 4,506,671 A | 3/1985 | Green | |
| 4,522,327 A | 6/1985 | Korthoff et al. | |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Lindsay Low

(57) ABSTRACT

A piece of buttress material and an end-effector of a surgical instrument including features which can aid a surgeon in properly and quickly attaching the piece of buttress material to the end-effector. In various embodiments, a piece of buttress material can include retention features which can be engaged with portions of an end-effector to releasably retain the piece of buttress material to at least a portion of the end-effector. Similarly, an end-effector can include features configured to engage portions of a piece of buttress material to releasably retain the piece of buttress material to the end-effector. In at least one embodiment, more than one piece of buttress material can be releasably retained to an end-effector.

15 Claims, 46 Drawing Sheets

U.S. PATENT DOCUMENTS

| | | |
|---|---|---|
| 4,530,453 A | 7/1985 | Green |
| 4,548,202 A * | 10/1985 | Duncan .................. 606/220 |
| 4,566,620 A | 1/1986 | Green et al. |
| 4,573,622 A | 3/1986 | Green et al. |
| 4,580,712 A | 4/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,664,305 A | 5/1987 | Blake, III et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,844,068 A * | 7/1989 | Arata et al. ................ 227/175.1 |
| 4,869,414 A | 9/1989 | Green et al. |
| 4,869,415 A | 9/1989 | Fox |
| 4,941,623 A | 7/1990 | Pruitt |
| 4,944,443 A | 7/1990 | Oddsen et al. |
| 5,065,929 A | 11/1991 | Schulze et al. |
| 5,074,454 A | 12/1991 | Peters |
| 5,129,570 A | 7/1992 | Schulze et al. |
| 5,137,198 A | 8/1992 | Nobis et al. |
| 5,141,144 A | 8/1992 | Foslien et al. |
| 5,190,544 A * | 3/1993 | Chapman et al. ............. 606/71 |
| 5,197,966 A * | 3/1993 | Sommerkamp ............. 606/286 |
| 5,221,036 A | 6/1993 | Takase |
| 5,263,629 A | 11/1993 | Trumbull et al. |
| 5,336,232 A | 8/1994 | Green et al. |
| 5,397,324 A * | 3/1995 | Carroll et al. ................ 606/139 |
| 5,405,072 A | 4/1995 | Zlock et al. |
| 5,413,272 A | 5/1995 | Green et al. |
| 5,417,361 A | 5/1995 | Williamson, IV |
| 5,441,193 A | 8/1995 | Gravener |
| 5,445,644 A | 8/1995 | Pietrafitta et al. |
| 5,452,837 A | 9/1995 | Williamson, IV et al. |
| 5,480,089 A | 1/1996 | Blewett |
| 5,482,197 A | 1/1996 | Green et al. |
| 5,484,095 A | 1/1996 | Green et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,638 A * | 4/1996 | Cooper et al. ............. 623/11.11 |
| 5,505,363 A | 4/1996 | Green et al. |
| 5,507,426 A | 4/1996 | Young et al. |
| 5,509,596 A | 4/1996 | Green et al. |
| 5,529,235 A | 6/1996 | Boiarski et al. |
| 5,533,661 A | 7/1996 | Main et al. |
| 5,535,934 A | 7/1996 | Boiarski et al. |
| 5,540,375 A | 7/1996 | Bolanos et al. |
| 5,542,594 A | 8/1996 | McKean et al. |
| 5,549,628 A * | 8/1996 | Cooper et al. ................ 606/220 |
| 5,553,765 A | 9/1996 | Knodel et al. |
| 5,560,530 A | 10/1996 | Bolanos et al. |
| 5,560,532 A | 10/1996 | DeFonzo et al. |
| 5,562,241 A | 10/1996 | Knodel et al. |
| 5,564,615 A | 10/1996 | Bishop et al. |
| 5,575,803 A * | 11/1996 | Cooper et al. ................ 606/151 |
| 5,577,654 A | 11/1996 | Bishop |
| 5,580,067 A | 12/1996 | Hamblin et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,601,224 A | 2/1997 | Bishop et al. |
| 5,603,443 A | 2/1997 | Clark et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,620,452 A | 4/1997 | Yoon |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,780 A | 6/1997 | Green et al. |
| 5,639,008 A | 6/1997 | Gallagher et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,680,981 A | 10/1997 | Mililli et al. |
| 5,680,982 A | 10/1997 | Schulze et al. |
| 5,685,474 A | 11/1997 | Seeber |
| 5,690,269 A | 11/1997 | Bolanos et al. |
| 5,692,668 A | 12/1997 | Schulze et al. |
| 5,697,543 A | 12/1997 | Burdorff |
| 5,702,409 A | 12/1997 | Rayburn et al. |
| 5,704,534 A | 1/1998 | Huitema et al. |
| 5,711,472 A | 1/1998 | Bryan |
| 5,713,505 A | 2/1998 | Huitema |
| 5,715,987 A | 2/1998 | Kelley et al. |
| 5,718,360 A | 2/1998 | Green et al. |
| 5,732,871 A | 3/1998 | Clark et al. |
| 5,732,872 A | 3/1998 | Bolduc et al. |
| 5,743,456 A | 4/1998 | Jones et al. |
| 5,752,644 A | 5/1998 | Bolanos et al. |
| 5,752,965 A | 5/1998 | Francis et al. |
| 5,758,814 A | 6/1998 | Gallagher et al. |
| 5,762,256 A | 6/1998 | Mastri et al. |
| 5,766,188 A | 6/1998 | Igaki |
| 5,769,892 A | 6/1998 | Kingwell |
| 5,779,130 A | 7/1998 | Alesi et al. |
| 5,779,131 A | 7/1998 | Knodel et al. |
| 5,779,132 A | 7/1998 | Knodel et al. |
| 5,782,397 A | 7/1998 | Koukline |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,810,855 A | 9/1998 | Rayburn et al. |
| 5,814,057 A * | 9/1998 | Oi et al. .................. 606/151 |
| 5,820,009 A | 10/1998 | Melling et al. |
| 5,826,776 A | 10/1998 | Schulze et al. |
| 5,829,662 A | 11/1998 | Allen et al. |
| 5,833,695 A * | 11/1998 | Yoon .......................... 606/139 |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,871,135 A | 2/1999 | Williamson, IV et al. |
| 5,901,895 A | 5/1999 | Heaton et al. |
| 5,902,312 A * | 5/1999 | Frater et al. .................... 606/148 |
| 5,908,427 A | 6/1999 | McKean et al. |
| 5,911,353 A | 6/1999 | Bolanos et al. |
| 5,915,616 A | 6/1999 | Viola et al. |
| 5,937,951 A | 8/1999 | Izuchukwu et al. |
| 5,941,442 A | 8/1999 | Geiste et al. |
| 5,954,259 A | 9/1999 | Viola et al. |
| 5,964,774 A * | 10/1999 | McKean et al. ................ 606/151 |
| 6,010,054 A | 1/2000 | Johnson et al. |
| 6,032,849 A | 3/2000 | Mastri et al. |
| 6,053,390 A | 4/2000 | Green et al. |
| 6,063,097 A | 5/2000 | Oi et al. |
| 6,099,551 A * | 8/2000 | Gabbay .................. 606/219 |

| | | | | | | |
|---|---|---|---|---|---|---|
| 6,102,271 | A | 8/2000 | Longo et al. | 7,128,748 B2 | 10/2006 | Mooradian et al. |
| 6,119,913 | A | 9/2000 | Adams et al. | 7,140,527 B2 * | 11/2006 | Ehrenfels et al. .......... 227/175.1 |
| 6,126,058 | A | 10/2000 | Adams et al. | 7,143,926 B2 | 12/2006 | Shelton, IV et al. |
| 6,193,129 | B1 | 2/2001 | Bittner et al. | 7,147,138 B2 * | 12/2006 | Shelton, IV ................ 227/176.1 |
| 6,202,914 | B1 | 3/2001 | Geiste et al. | 7,147,139 B2 | 12/2006 | Schwemberger et al. |
| 6,241,139 | B1 | 6/2001 | Milliman et al. | 7,159,750 B2 | 1/2007 | Racenet et al. |
| 6,250,532 | B1 | 6/2001 | Green et al. | 7,168,604 B2 | 1/2007 | Milliman et al. |
| 6,264,086 | B1 | 7/2001 | McGuckin, Jr. | 7,172,593 B2 | 2/2007 | Trieu et al. |
| 6,264,087 | B1 | 7/2001 | Whitman | 7,182,239 B1 | 2/2007 | Myers |
| 6,273,897 | B1 | 8/2001 | Dalessandro et al. | 7,188,758 B2 | 3/2007 | Viola et al. |
| 6,302,311 | B1 | 10/2001 | Adams et al. | 7,207,471 B2 | 4/2007 | Heinrich et al. |
| 6,315,184 | B1 | 11/2001 | Whitman | 7,207,472 B2 | 4/2007 | Wukusick et al. |
| 6,325,810 | B1 * | 12/2001 | Hamilton et al. ............. 606/151 | 7,210,609 B2 | 5/2007 | Leiboff et al. |
| 6,330,965 | B1 | 12/2001 | Milliman et al. | 7,213,736 B2 | 5/2007 | Wales et al. |
| 6,488,196 | B1 | 12/2002 | Fenton, Jr. | 7,225,964 B2 | 6/2007 | Mastri et al. |
| 6,488,197 | B1 | 12/2002 | Whitman | 7,234,624 B2 | 6/2007 | Gresham et al. |
| 6,491,201 | B1 | 12/2002 | Whitman | 7,237,708 B1 | 7/2007 | Guy et al. |
| 6,503,257 | B2 | 1/2003 | Grant et al. | 7,246,734 B2 | 7/2007 | Shelton, IV |
| 6,505,768 | B2 | 1/2003 | Whitman | 7,258,262 B2 | 8/2007 | Mastri et al. |
| 6,551,333 | B2 | 4/2003 | Kuhns et al. | 7,267,679 B2 | 9/2007 | McGuckin, Jr. et al. |
| 6,578,751 | B2 | 6/2003 | Hartwick | 7,278,562 B2 | 10/2007 | Mastri et al. |
| 6,588,643 | B2 | 7/2003 | Bolduc et al. | 7,278,563 B1 | 10/2007 | Green |
| 6,592,597 | B2 | 7/2003 | Grant et al. | 7,296,724 B2 | 11/2007 | Green et al. |
| 6,601,749 | B2 | 8/2003 | Sullivan et al. | 7,303,106 B2 | 12/2007 | Milliman et al. |
| 6,619,529 | B2 | 9/2003 | Green et al. | 7,303,107 B2 | 12/2007 | Milliman et al. |
| 6,629,630 | B2 | 10/2003 | Adams | 7,303,108 B2 | 12/2007 | Shelton, IV |
| 6,638,285 | B2 * | 10/2003 | Gabbay ........................ 606/151 | 7,328,828 B2 | 2/2008 | Ortiz et al. |
| 6,644,532 | B2 | 11/2003 | Green et al. | 7,328,829 B2 | 2/2008 | Arad et al. |
| 6,656,193 | B2 | 12/2003 | Grant et al. | 7,334,717 B2 | 2/2008 | Rethy et al. |
| 6,681,978 | B2 | 1/2004 | Geiste et al. | 7,354,447 B2 | 4/2008 | Shelton, IV et al. |
| 6,681,979 | B2 | 1/2004 | Whitman | 7,357,287 B2 | 4/2008 | Shelton, IV et al. |
| 6,695,199 | B2 | 2/2004 | Whitman | 7,364,060 B2 | 4/2008 | Milliman |
| 6,698,643 | B2 | 3/2004 | Whitman | 7,364,061 B2 | 4/2008 | Swayze et al. |
| 6,704,210 | B1 * | 3/2004 | Myers .......................... 361/773 | 7,377,928 B2 | 5/2008 | Zubik et al. |
| 6,722,552 | B2 | 4/2004 | Fenton, Jr. | 7,380,695 B2 | 6/2008 | Doll et al. |
| 6,755,338 | B2 | 6/2004 | Hahnen et al. | 7,380,696 B2 | 6/2008 | Shelton, IV et al. |
| 6,769,594 | B2 | 8/2004 | Orban, III | 7,398,907 B2 | 7/2008 | Racenet et al. |
| 6,786,382 | B1 | 9/2004 | Hoffman | 7,398,908 B2 | 7/2008 | Holsten et al. |
| 6,805,273 | B2 | 10/2004 | Bilotti et al. | 7,404,508 B2 | 7/2008 | Smith et al. |
| 6,817,508 | B1 | 11/2004 | Racenet et al. | 7,404,509 B2 | 7/2008 | Ortiz et al. |
| 6,817,509 | B2 | 11/2004 | Geiste et al. | 7,407,075 B2 | 8/2008 | Holsten et al. |
| 6,821,284 | B2 | 11/2004 | Sturtz et al. | 7,407,078 B2 | 8/2008 | Shelton, IV et al. |
| 6,830,174 | B2 | 12/2004 | Hillstead et al. | 7,410,086 B2 | 8/2008 | Ortiz et al. |
| 6,843,403 | B2 | 1/2005 | Whitman | 7,416,101 B2 | 8/2008 | Shelton, IV et al. |
| RE38,708 | E | 3/2005 | Bolanos et al. | 7,419,080 B2 | 9/2008 | Smith et al. |
| 6,866,178 | B2 | 3/2005 | Adams et al. | 7,422,136 B1 | 9/2008 | Marczyk |
| 6,874,669 | B2 | 4/2005 | Adams et al. | 7,422,139 B2 | 9/2008 | Shelton, IV et al. |
| 6,877,647 | B2 | 4/2005 | Green et al. | 7,424,965 B2 | 9/2008 | Racenet et al. |
| 6,905,057 | B2 | 6/2005 | Swayze et al. | 7,431,188 B1 | 10/2008 | Marczyk |
| 6,913,608 | B2 | 7/2005 | Liddicoat et al. | 7,438,209 B1 | 10/2008 | Hess et al. |
| 6,939,358 | B2 | 9/2005 | Palacios et al. | 7,441,685 B1 | 10/2008 | Boudreaux |
| 6,945,444 | B2 | 9/2005 | Gresham et al. | 7,455,208 B2 | 11/2008 | Wales et al. |
| 6,953,138 | B1 | 10/2005 | Dworak et al. | 7,481,347 B2 | 1/2009 | Roy |
| 6,953,139 | B2 | 10/2005 | Milliman et al. | 7,481,349 B2 | 1/2009 | Holsten et al. |
| 6,959,851 | B2 | 11/2005 | Heinrich | 7,490,749 B2 | 2/2009 | Schall et al. |
| 6,959,852 | B2 | 11/2005 | Shelton, IV et al. | 7,494,039 B2 | 2/2009 | Racenet et al. |
| 6,964,363 | B2 | 11/2005 | Wales et al. | 7,506,790 B2 | 3/2009 | Shelton, IV |
| 6,978,921 | B2 | 12/2005 | Shelton, IV et al. | 7,510,107 B2 | 3/2009 | Timm et al. |
| 6,978,922 | B2 | 12/2005 | Bilotti et al. | 7,546,940 B2 | 6/2009 | Milliman et al. |
| 6,981,628 | B2 | 1/2006 | Wales | 7,547,312 B2 | 6/2009 | Bauman et al. |
| 6,986,451 | B1 | 1/2006 | Mastri et al. | 7,549,563 B2 | 6/2009 | Mather et al. |
| 6,988,650 | B2 | 1/2006 | Schwemberger et al. | 7,556,185 B2 | 7/2009 | Viola |
| 7,000,818 | B2 | 2/2006 | Shelton, IV et al. | 7,556,186 B2 | 7/2009 | Milliman |
| 7,000,819 | B2 | 2/2006 | Swayze et al. | 7,559,450 B2 | 7/2009 | Wales et al. |
| 7,032,798 | B2 | 4/2006 | Whitman et al. | 7,559,452 B2 | 7/2009 | Wales et al. |
| 7,032,799 | B2 | 4/2006 | Viola et al. | 7,568,604 B2 | 8/2009 | Ehrenfels et al. |
| 7,044,352 | B2 | 5/2006 | Shelton, IV et al. | 7,575,144 B2 | 8/2009 | Ortiz et al. |
| 7,044,353 | B2 | 5/2006 | Mastri et al. | 7,611,038 B2 | 11/2009 | Racenet et al. |
| 7,052,499 | B2 * | 5/2006 | Steger et al. ................... 606/291 | 7,624,902 B2 | 12/2009 | Marczyk et al. |
| 7,055,731 | B2 | 6/2006 | Shelton, IV et al. | 7,631,793 B2 | 12/2009 | Rethy et al. |
| 7,066,944 | B2 | 6/2006 | Laufer et al. | 7,637,409 B2 | 12/2009 | Marczyk |
| 7,070,083 | B2 | 7/2006 | Jankowski | 7,665,646 B2 | 2/2010 | Prommersberger |
| 7,080,769 | B2 | 7/2006 | Vresh et al. | 7,699,204 B2 | 4/2010 | Viola |
| 7,083,075 | B2 | 8/2006 | Swayze et al. | 7,717,312 B2 | 5/2010 | Beetel |
| 7,111,769 | B2 | 9/2006 | Wales et al. | 7,721,930 B2 | 5/2010 | McKenna et al. |
| 7,114,642 | B2 | 10/2006 | Whitman | 7,726,537 B2 | 6/2010 | Olson et al. |
| 7,121,446 | B2 | 10/2006 | Arad et al. | 7,726,538 B2 | 6/2010 | Holsten et al. |
| 7,128,253 | B2 | 10/2006 | Mastri et al. | 7,743,960 B2 | 6/2010 | Whitman et al. |
| 7,128,254 | B2 | 10/2006 | Shelton, IV et al. | 7,766,209 B2 | 8/2010 | Baxter, III et al. |

| Patent/Publication | Date | Inventor |
|---|---|---|
| 7,776,060 B2 | 8/2010 | Mooradian et al. |
| 7,780,054 B2 | 8/2010 | Wales |
| 7,780,685 B2 | 8/2010 | Hunt et al. |
| 7,784,662 B2 | 8/2010 | Wales et al. |
| 7,793,812 B2 | 9/2010 | Moore et al. |
| 7,810,692 B2 | 10/2010 | Hall et al. |
| 7,832,611 B2 | 11/2010 | Boyden et al. |
| 7,837,081 B2 | 11/2010 | Holsten et al. |
| 7,845,533 B2 | 12/2010 | Marczyk et al. |
| 7,909,221 B2 | 3/2011 | Viola et al. |
| 7,922,063 B2 | 4/2011 | Zemlok et al. |
| 7,938,307 B2 | 5/2011 | Bettuchi |
| 7,950,560 B2 | 5/2011 | Zemlok et al. |
| 7,967,180 B2 | 6/2011 | Scirica |
| 8,038,046 B2 | 10/2011 | Smith et al. |
| D650,074 S | 12/2011 | Hunt et al. |
| 8,113,410 B2 | 2/2012 | Hall et al. |
| 8,123,103 B2 | 2/2012 | Milliman |
| 8,136,712 B2 | 3/2012 | Zingman |
| 8,211,125 B2 | 7/2012 | Spivey |
| 2002/0117534 A1 | 8/2002 | Green et al. |
| 2002/0143340 A1* | 10/2002 | Kaneko ............................ 606/72 |
| 2003/0220660 A1 | 11/2003 | Kortenbach et al. |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0164123 A1 | 8/2004 | Racenet et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2005/0070929 A1 | 3/2005 | Dalessandro et al. |
| 2005/0103819 A1 | 5/2005 | Racenet et al. |
| 2005/0145675 A1 | 7/2005 | Hartwick et al. |
| 2005/0177181 A1 | 8/2005 | Kagan et al. |
| 2005/0184121 A1 | 8/2005 | Heinrich |
| 2005/0189397 A1 | 9/2005 | Jankowski |
| 2005/0203550 A1 | 9/2005 | Laufer et al. |
| 2005/0240222 A1* | 10/2005 | Shipp ............................ 606/219 |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0049229 A1 | 3/2006 | Milliman et al. |
| 2006/0108393 A1 | 5/2006 | Heinrich et al. |
| 2006/0173470 A1 | 8/2006 | Oray et al. |
| 2006/0180634 A1 | 8/2006 | Shelton, IV et al. |
| 2006/0226196 A1 | 10/2006 | Hueil et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0034668 A1 | 2/2007 | Holsten et al. |
| 2007/0045379 A1 | 3/2007 | Shelton, IV |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton, IV et al. |
| 2007/0246505 A1* | 10/2007 | Pace-Floridia et al. .... 227/175.1 |
| 2007/0262116 A1 | 11/2007 | Hueil et al. |
| 2007/0295780 A1 | 12/2007 | Shelton et al. |
| 2008/0003196 A1 | 1/2008 | Jonn et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0185419 A1 | 8/2008 | Smith et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0251569 A1 | 10/2008 | Smith et al. |
| 2008/0283570 A1 | 11/2008 | Boyden et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0308608 A1* | 12/2008 | Prommersberger ....... 227/176.1 |
| 2008/0314954 A1 | 12/2008 | Boudreaux |
| 2008/0314955 A1 | 12/2008 | Boudreaux et al. |
| 2008/0314956 A1 | 12/2008 | Boudreaux |
| 2008/0314957 A1 | 12/2008 | Boudreaux |
| 2008/0314960 A1* | 12/2008 | Marczyk et al. ........... 227/178.1 |
| 2008/0314961 A1 | 12/2008 | Boudreaux et al. |

| Publication No. | Date | Inventor(s) |
|---|---|---|
| 2008/0314962 A1 | 12/2008 | Boudreaux |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0057369 A1 | 3/2009 | Smith et al. |
| 2009/0076534 A1 | 3/2009 | Shelton, IV et al. |
| 2009/0108048 A1 | 4/2009 | Zemlok et al. |
| 2009/0114701 A1 | 5/2009 | Zemlok et al. |
| 2009/0149871 A9 | 6/2009 | Kagan et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0289096 A1 | 11/2009 | Shelton, IV et al. |
| 2010/0001036 A1 | 1/2010 | Marczyk et al. |
| 2010/0012704 A1 | 1/2010 | Tarinelli Racenet et al. |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072251 A1 | 3/2010 | Baxter, III et al. |
| 2010/0072252 A1 | 3/2010 | Baxter, III et al. |
| 2010/0072253 A1 | 3/2010 | Baxter, III et al. |
| 2010/0072254 A1 | 3/2010 | Aranyi et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096435 A1 | 4/2010 | Fuchs et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0237132 A1 | 9/2010 | Measamer et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0264194 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0210156 A1 | 9/2011 | Smith et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |

| | | | | | | |
|---|---|---|---|---|---|---|
| 2012/0029544 A1 | 2/2012 | Shelton, IV et al. | | EP | 0033548 B1 | 5/1986 |
| 2012/0029547 A1 | 2/2012 | Shelton, IV et al. | | EP | 0276104 A2 | 7/1988 |
| 2012/0061448 A1 | 3/2012 | Zingman | | EP | 0248844 B1 | 1/1993 |
| 2012/0071711 A1 | 3/2012 | Shelton, IV et al. | | EP | 0545029 A1 | 6/1993 |
| 2012/0071866 A1 | 3/2012 | Kerr et al. | | EP | 0277959 B1 | 10/1993 |
| 2012/0074196 A1 | 3/2012 | Shelton, IV et al. | | EP | 0233940 B1 | 11/1993 |
| 2012/0074198 A1 | 3/2012 | Huitema et al. | | EP | 0261230 B1 | 11/1993 |
| 2012/0074200 A1 | 3/2012 | Schmid et al. | | EP | 0639349 A2 | 2/1994 |
| 2012/0074201 A1 | 3/2012 | Baxter, III et al. | | EP | 0324636 B1 | 3/1994 |
| 2012/0080332 A1 | 4/2012 | Shelton, IV et al. | | EP | 0593920 A1 | 4/1994 |
| 2012/0080333 A1 | 4/2012 | Woodard, Jr. et al. | | EP | 0594148 A1 | 4/1994 |
| 2012/0080334 A1 | 4/2012 | Shelton, IV et al. | | EP | 0427949 B1 | 6/1994 |
| 2012/0080335 A1 | 4/2012 | Shelton, IV et al. | | EP | 0523174 B1 | 6/1994 |
| 2012/0080336 A1 | 4/2012 | Shelton, IV et al. | | EP | 0600182 A2 | 6/1994 |
| 2012/0080337 A1 | 4/2012 | Shelton, IV et al. | | EP | 0310431 B1 | 11/1994 |
| 2012/0080338 A1 | 4/2012 | Shelton, IV et al. | | EP | 0375302 B1 | 11/1994 |
| 2012/0080339 A1 | 4/2012 | Shelton, IV et al. | | EP | 0376562 B1 | 11/1994 |
| 2012/0080340 A1 | 4/2012 | Shelton, IV et al. | | EP | 0630612 A1 | 12/1994 |
| 2012/0080344 A1 | 4/2012 | Shelton, IV | | EP | 0634144 A1 | 1/1995 |
| 2012/0080345 A1 | 4/2012 | Morgan et al. | | EP | 0646356 A2 | 4/1995 |
| 2012/0080475 A1 | 4/2012 | Smith et al. | | EP | 0646357 A1 | 4/1995 |
| 2012/0080477 A1 | 4/2012 | Leimbach et al. | | EP | 0653189 A2 | 5/1995 |
| 2012/0080478 A1 | 4/2012 | Morgan et al. | | EP | 0669104 A1 | 8/1995 |
| 2012/0080479 A1 | 4/2012 | Shelton, IV | | EP | 0511470 B1 | 10/1995 |
| 2012/0080480 A1 | 4/2012 | Woodard, Jr. et al. | | EP | 0679367 A2 | 11/1995 |
| 2012/0080481 A1 | 4/2012 | Widenhouse et al. | | EP | 0392547 B1 | 12/1995 |
| 2012/0080482 A1 | 4/2012 | Schall et al. | | EP | 0685204 A1 | 12/1995 |
| 2012/0080483 A1 | 4/2012 | Riestenberg et al. | | EP | 0364216 B1 | 1/1996 |
| 2012/0080484 A1 | 4/2012 | Morgan et al. | | EP | 0699418 A1 | 3/1996 |
| 2012/0080485 A1 | 4/2012 | Woodard, Jr. et al. | | EP | 0702937 A1 | 3/1996 |
| 2012/0080486 A1 | 4/2012 | Woodard, Jr. et al. | | EP | 0705571 A1 | 4/1996 |
| 2012/0080487 A1 | 4/2012 | Woodard, Jr. et al. | | EP | 0711611 A2 | 5/1996 |
| 2012/0080488 A1 | 4/2012 | Shelton, IV et al. | | EP | 0484677 B2 | 6/1996 |
| 2012/0080489 A1 | 4/2012 | Shelton, IV et al. | | EP | 0541987 B1 | 7/1996 |
| 2012/0080490 A1 | 4/2012 | Shelton, IV et al. | | EP | 0667119 B1 | 7/1996 |
| 2012/0080491 A1 | 4/2012 | Shelton, IV et al. | | EP | 0708618 B1 | 3/1997 |
| 2012/0080493 A1 | 4/2012 | Shelton, IV et al. | | EP | 0770355 A1 | 5/1997 |
| 2012/0080496 A1 | 4/2012 | Schall et al. | | EP | 0503662 B1 | 6/1997 |
| 2012/0080498 A1 | 4/2012 | Shelton, IV et al. | | EP | 0447121 B1 | 7/1997 |
| 2012/0080499 A1 | 4/2012 | Schall et al. | | EP | 0625077 B1 | 7/1997 |
| 2012/0080500 A1 | 4/2012 | Morgan et al. | | EP | 0633749 B1 | 8/1997 |
| 2012/0080501 A1 | 4/2012 | Morgan et al. | | EP | 0710090 B1 | 8/1997 |
| 2012/0080502 A1 | 4/2012 | Morgan et al. | | EP | 0578425 B1 | 9/1997 |
| 2012/0080503 A1 | 4/2012 | Woodard, Jr. et al. | | EP | 0625335 B1 | 11/1997 |
| 2012/0083833 A1 | 4/2012 | Shelton, IV et al. | | EP | 0552423 B1 | 1/1998 |
| 2012/0083834 A1 | 4/2012 | Shelton, IV et al. | | EP | 0592244 B1 | 1/1998 |
| 2012/0083835 A1 | 4/2012 | Shelton, IV et al. | | EP | 0648476 B1 | 1/1998 |
| 2012/0083836 A1 | 4/2012 | Shelton, IV et al. | | EP | 0649290 B1 | 3/1998 |
| 2012/0132450 A1 | 5/2012 | Timm et al. | | EP | 0598618 B1 | 9/1998 |
| 2012/0138660 A1 | 6/2012 | Shelton, IV | | EP | 0676173 B1 | 9/1998 |
| 2012/0160721 A1 | 6/2012 | Shelton, IV et al. | | EP | 0678007 B1 | 9/1998 |
| 2012/0175399 A1 | 7/2012 | Shelton et al. | | EP | 0603472 B1 | 11/1998 |
| 2012/0199630 A1 | 8/2012 | Shelton, IV | | EP | 0605351 B1 | 11/1998 |
| 2012/0199631 A1 | 8/2012 | Shelton, IV et al. | | EP | 0878169 A1 | 11/1998 |
| 2012/0199632 A1 | 8/2012 | Spivey et al. | | EP | 0879742 A1 | 11/1998 |
| 2012/0199633 A1 | 8/2012 | Shelton, IV et al. | | EP | 0695144 B1 | 12/1998 |
| 2012/0203247 A1 | 8/2012 | Shelton, IV et al. | | EP | 0722296 B1 | 12/1998 |
| 2012/0205421 A1 | 8/2012 | Shelton, IV | | EP | 0760230 B1 | 2/1999 |
| 2012/0211546 A1 | 8/2012 | Shelton, IV | | EP | 0623316 B1 | 3/1999 |
| | | | | EP | 0650701 B1 | 3/1999 |
| | FOREIGN PATENT DOCUMENTS | | | EP | 0537572 B1 | 6/1999 |
| CA | 2514274 A1 | 1/2006 | | EP | 0923907 A1 | 6/1999 |
| CN | 1868411 A | 11/2006 | | EP | 0843906 B1 | 3/2000 |
| CN | 1915180 A | 2/2007 | | EP | 0552050 B1 | 5/2000 |
| CN | 101095621 A | 1/2008 | | EP | 0833592 B1 | 5/2000 |
| DE | 273689 C | 5/1914 | | EP | 0830094 B1 | 9/2000 |
| DE | 1775926 A | 1/1972 | | EP | 1034747 A1 | 9/2000 |
| DE | 9412228 U | 9/1994 | | EP | 1034748 A1 | 9/2000 |
| DE | 19509116 A1 | 9/1996 | | EP | 0694290 B1 | 11/2000 |
| DE | 19851291 A1 | 1/2000 | | EP | 1050278 A1 | 11/2000 |
| DE | 19924311 A1 | 11/2000 | | EP | 1053719 A1 | 11/2000 |
| DE | 69328576 T2 | 1/2001 | | EP | 1053720 A1 | 11/2000 |
| DE | 10052679 A1 | 5/2001 | | EP | 1055399 A1 | 11/2000 |
| DE | 20112837 U1 | 10/2001 | | EP | 1055400 A1 | 11/2000 |
| DE | 20121753 U1 | 4/2003 | | EP | 1080694 A1 | 3/2001 |
| DE | 10314072 A1 | 10/2004 | | EP | 1090592 A1 | 4/2001 |
| EP | 0122046 A1 | 10/1984 | | EP | 1095627 A1 | 5/2001 |
| EP | 0070230 B1 | 10/1985 | | EP | 1256318 B1 | 5/2001 |
| EP | 0387980 B1 | 10/1985 | | EP | 0806914 B1 | 9/2001 |

| | | | | | | |
|---|---|---|---|---|---|---|
| EP | 0768840 B1 | 12/2001 | | EP | 1256317 B1 | 12/2006 |
| EP | 0908152 B1 | 1/2002 | | EP | 1285633 B1 | 12/2006 |
| EP | 0872213 B1 | 5/2002 | | EP | 1728473 A1 | 12/2006 |
| EP | 0862386 B1 | 6/2002 | | EP | 1728475 A2 | 12/2006 |
| EP | 0949886 B1 | 9/2002 | | EP | 1479346 B1 | 1/2007 |
| EP | 1238634 A2 | 9/2002 | | EP | 1484024 B1 | 1/2007 |
| EP | 0858295 B1 | 12/2002 | | EP | 1754445 A2 | 2/2007 |
| EP | 0656188 B1 | 1/2003 | | EP | 1759812 A1 | 3/2007 |
| EP | 1284120 A1 | 2/2003 | | EP | 1767163 A1 | 3/2007 |
| EP | 1287788 A1 | 3/2003 | | EP | 1769756 A1 | 4/2007 |
| EP | 0717966 B1 | 4/2003 | | EP | 1769758 A1 | 4/2007 |
| EP | 0869742 B1 | 5/2003 | | EP | 1581128 B1 | 5/2007 |
| EP | 0829235 B1 | 6/2003 | | EP | 1785097 A2 | 5/2007 |
| EP | 0887046 B1 | 7/2003 | | EP | 1790293 A2 | 5/2007 |
| EP | 0852480 B1 | 8/2003 | | EP | 1800610 A1 | 6/2007 |
| EP | 0891154 B1 | 9/2003 | | EP | 1300117 B1 | 8/2007 |
| EP | 0813843 B1 | 10/2003 | | EP | 1813199 A1 | 8/2007 |
| EP | 0873089 B1 | 10/2003 | | EP | 1813201 A1 | 8/2007 |
| EP | 0856326 B1 | 11/2003 | | EP | 1813203 A2 | 8/2007 |
| EP | 1374788 A1 | 1/2004 | | EP | 1813207 A1 | 8/2007 |
| EP | 0741996 B1 | 2/2004 | | EP | 1813209 A1 | 8/2007 |
| EP | 0814712 B1 | 2/2004 | | EP | 1487359 B1 | 10/2007 |
| EP | 1402837 A1 | 3/2004 | | EP | 1599146 B1 | 10/2007 |
| EP | 0705570 B1 | 4/2004 | | EP | 1402821 B1 | 12/2007 |
| EP | 0959784 B1 | 4/2004 | | EP | 1872727 A1 | 1/2008 |
| EP | 1407719 A2 | 4/2004 | | EP | 1839596 A2 | 2/2008 |
| EP | 1086713 B1 | 5/2004 | | EP | 1897502 A1 | 3/2008 |
| EP | 0996378 B1 | 6/2004 | | EP | 1330201 B1 | 6/2008 |
| EP | 1426012 A1 | 6/2004 | | EP | 1702568 B1 | 7/2008 |
| EP | 0833593 B2 | 7/2004 | | EP | 1943957 A2 | 7/2008 |
| EP | 1442694 A1 | 8/2004 | | EP | 1943976 A2 | 7/2008 |
| EP | 0888749 B1 | 9/2004 | | EP | 1593337 B1 | 8/2008 |
| EP | 0959786 B1 | 9/2004 | | EP | 1970014 A1 | 9/2008 |
| EP | 1459695 A1 | 9/2004 | | EP | 1980213 A2 | 10/2008 |
| EP | 1473819 A1 | 11/2004 | | EP | 1759645 B1 | 11/2008 |
| EP | 1477119 A1 | 11/2004 | | EP | 1990014 A2 | 11/2008 |
| EP | 1479345 A1 | 11/2004 | | EP | 1693008 B1 | 12/2008 |
| EP | 1479347 A1 | 11/2004 | | EP | 1759640 B1 | 12/2008 |
| EP | 1479348 A1 | 11/2004 | | EP | 2000102 A2 | 12/2008 |
| EP | 0754437 B2 | 12/2004 | | EP | 1736104 B1 | 3/2009 |
| EP | 1025807 B1 | 12/2004 | | EP | 1749486 B1 | 3/2009 |
| EP | 1001710 B1 | 1/2005 | | EP | 2039316 A2 | 3/2009 |
| EP | 1520521 A1 | 4/2005 | | EP | 1721576 B1 | 4/2009 |
| EP | 1520523 A1 | 4/2005 | | EP | 1733686 B1 | 4/2009 |
| EP | 1520525 A1 | 4/2005 | | EP | 2044890 A1 | 4/2009 |
| EP | 1522264 A1 | 4/2005 | | EP | 1550413 B1 | 6/2009 |
| EP | 1523942 A2 | 4/2005 | | EP | 1745748 B1 | 8/2009 |
| EP | 1550408 A1 | 7/2005 | | EP | 2090256 A2 | 8/2009 |
| EP | 1557129 A1 | 7/2005 | | EP | 1813208 B1 | 11/2009 |
| EP | 1064883 B1 | 8/2005 | | EP | 1607050 B1 | 12/2009 |
| EP | 1067876 B1 | 8/2005 | | EP | 1566150 B1 | 4/2010 |
| EP | 0870473 B1 | 9/2005 | | EP | 1813206 B1 | 4/2010 |
| EP | 1157666 B1 | 9/2005 | | EP | 1769754 B1 | 6/2010 |
| EP | 0880338 B1 | 10/2005 | | EP | 1535565 B1 | 10/2010 |
| EP | 1158917 B1 | 11/2005 | | EP | 1702570 B1 | 10/2010 |
| EP | 1344498 B1 | 11/2005 | | EP | 1785098 B1 | 10/2010 |
| EP | 1330989 B1 | 12/2005 | | EP | 1627605 B1 | 12/2010 |
| EP | 0771176 B2 | 1/2006 | | EP | 1813205 B1 | 6/2011 |
| EP | 1621138 A2 | 2/2006 | | EP | 1785102 B1 | 1/2012 |
| EP | 1621139 A2 | 2/2006 | | FR | 999646 A | 2/1952 |
| EP | 1621141 A2 | 2/2006 | | FR | 1112936 A | 3/1956 |
| EP | 1621145 A2 | 2/2006 | | FR | 2765794 A | 1/1999 |
| EP | 1621151 A2 | 2/2006 | | GB | 939929 A | 10/1963 |
| EP | 1034746 B1 | 3/2006 | | GB | 1210522 A | 10/1970 |
| EP | 1632191 A2 | 3/2006 | | GB | 1217159 A | 12/1970 |
| EP | 1065981 B1 | 5/2006 | | GB | 1339394 A | 12/1973 |
| EP | 1082944 B1 | 5/2006 | | GB | 2109241 A | 6/1983 |
| EP | 1652481 A2 | 5/2006 | | GB | 2272159 A | 5/1994 |
| EP | 1382303 B1 | 6/2006 | | GB | 2284242 A | 5/1995 |
| EP | 1253866 B1 | 7/2006 | | GB | 2336214 A | 10/1999 |
| EP | 1032318 B1 | 8/2006 | | GB | 2425903 A | 11/2006 |
| EP | 1045672 B1 | 8/2006 | | JP | 58500053 A | 1/1983 |
| EP | 1617768 B1 | 8/2006 | | JP | 61-98249 A | 5/1986 |
| EP | 1693015 A2 | 8/2006 | | JP | 63-203149 | 8/1988 |
| EP | 1400214 B1 | 9/2006 | | JP | 3-12126 A | 1/1991 |
| EP | 1702567 A2 | 9/2006 | | JP | 5-212039 A | 8/1993 |
| EP | 1129665 B1 | 11/2006 | | JP | 6007357 A | 1/1994 |
| EP | 1400206 B1 | 11/2006 | | JP | 7051273 A | 2/1995 |
| EP | 1721568 A1 | 11/2006 | | JP | 8033641 A | 2/1996 |

| | | | | | | | |
|---|---|---|---|---|---|---|---|
| JP | 8229050 | A | 9/1996 | WO | WO 96/39088 | A1 | 12/1996 |
| JP | 2000033071 | A | 2/2000 | WO | WO 96/39089 | A1 | 12/1996 |
| JP | 2000171730 | A | 6/2000 | WO | WO 97/00646 | A1 | 1/1997 |
| JP | 2000287987 | A | 10/2000 | WO | WO 97/00647 | A1 | 1/1997 |
| JP | 2000325303 | A | 11/2000 | WO | WO 97/06582 | A1 | 2/1997 |
| JP | 2001-514541 | A | 9/2001 | WO | WO 97/10763 | A1 | 3/1997 |
| JP | 2001286477 | A | 10/2001 | WO | WO 97/10764 | A1 | 3/1997 |
| JP | 2002143078 | A | 5/2002 | WO | WO 97/11648 | A2 | 4/1997 |
| JP | 2002369820 | A | 12/2002 | WO | WO 97/11649 | A1 | 4/1997 |
| JP | 2004-344663 | | 12/2004 | WO | WO 97/15237 | A1 | 5/1997 |
| JP | 2005-028149 | A | 2/2005 | WO | WO 97/24073 | A1 | 7/1997 |
| JP | 2005505322 | T | 2/2005 | WO | WO 97/24993 | A1 | 7/1997 |
| JP | 2005103293 | A | 4/2005 | WO | WO 97/30644 | A1 | 8/1997 |
| JP | 2005131163 | A | 5/2005 | WO | WO 97/34533 | A1 | 9/1997 |
| JP | 2005131164 | A | 5/2005 | WO | WO 97/37598 | A1 | 10/1997 |
| JP | 2005131173 | A | 5/2005 | WO | WO 97/39688 | A2 | 10/1997 |
| JP | 2005131211 | A | 5/2005 | WO | WO 98/17180 | A1 | 4/1998 |
| JP | 2005131212 | A | 5/2005 | WO | WO 98/27880 | A1 | 7/1998 |
| JP | 2005137423 | A | 6/2005 | WO | WO 98/30153 | A1 | 7/1998 |
| JP | 2005152416 | A | 6/2005 | WO | WO 98/47436 | A1 | 10/1998 |
| JP | 2005-523105 | A | 8/2005 | WO | WO 99/03407 | A1 | 1/1999 |
| JP | 2005524474 | A | 8/2005 | WO | WO 99/03408 | A1 | 1/1999 |
| JP | 2006-281405 | A | 10/2006 | WO | WO 99/03409 | A1 | 1/1999 |
| RU | 2008830 | C1 | 3/1994 | WO | WO 99/12483 | A1 | 3/1999 |
| RU | 2187249 | C2 | 8/2002 | WO | WO 99/12487 | A1 | 3/1999 |
| RU | 2225170 | C2 | 3/2004 | WO | WO 99/12488 | A1 | 3/1999 |
| SU | 189517 | A | 1/1967 | WO | WO 99/15086 | A1 | 4/1999 |
| SU | 328636 | A | 9/1972 | WO | WO 99/15091 | A1 | 4/1999 |
| SU | 886900 | A1 | 12/1981 | WO | WO 99/23933 | A2 | 5/1999 |
| SU | 1333319 | A2 | 8/1987 | WO | WO 99/23959 | A1 | 5/1999 |
| SU | 1377053 | A1 | 2/1988 | WO | WO 99/25261 | A1 | 5/1999 |
| SU | 1561964 | A1 | 5/1990 | WO | WO 99/29244 | A1 | 6/1999 |
| SU | 1722476 | A1 | 3/1992 | WO | WO 99/34744 | A1 | 7/1999 |
| WO | WO 82/02824 | A1 | 9/1982 | WO | WO 99/45849 | A1 | 9/1999 |
| WO | WO 91/15157 | A1 | 10/1991 | WO | WO 99/48430 | A1 | 9/1999 |
| WO | WO 92/20295 | A1 | 11/1992 | WO | WO 99/51158 | A1 | 10/1999 |
| WO | WO 92/21300 | A1 | 12/1992 | WO | WO 00/24322 | A1 | 5/2000 |
| WO | WO 93/08755 | A1 | 5/1993 | WO | WO 00/24330 | A1 | 5/2000 |
| WO | WO 93/13718 | A1 | 7/1993 | WO | WO 00/41638 | A1 | 7/2000 |
| WO | WO 93/14690 | A1 | 8/1993 | WO | WO 00/48506 | A1 | 8/2000 |
| WO | WO 93/15648 | A1 | 8/1993 | WO | WO 00/53112 | A2 | 9/2000 |
| WO | WO 93/15850 | A1 | 8/1993 | WO | WO 00/54653 | A1 | 9/2000 |
| WO | WO 93/19681 | A1 | 10/1993 | WO | WO 00/57796 | A1 | 10/2000 |
| WO | WO 94/00060 | A1 | 1/1994 | WO | WO 00/64365 | A1 | 11/2000 |
| WO | WO 94/11057 | A1 | 5/1994 | WO | WO 00/72762 | A1 | 12/2000 |
| WO | WO 94/12108 | A1 | 6/1994 | WO | WO 00/72765 | A1 | 12/2000 |
| WO | WO 94/18893 | A1 | 9/1994 | WO | WO 01/03587 | A1 | 1/2001 |
| WO | WO 94/22378 | A1 | 10/1994 | WO | WO 01/05702 | A1 | 1/2001 |
| WO | WO 94/23659 | A1 | 10/1994 | WO | WO 01/10482 | A1 | 2/2001 |
| WO | WO 95/02369 | A1 | 1/1995 | WO | WO 01/35845 | A1 | 5/2001 |
| WO | WO 95/03743 | A1 | 2/1995 | WO | WO 01/54594 | A1 | 8/2001 |
| WO | WO 95/06817 | A1 | 3/1995 | WO | WO 01/58371 | A1 | 8/2001 |
| WO | WO 95/09576 | A1 | 4/1995 | WO | WO 01/62158 | A2 | 8/2001 |
| WO | WO 95/09577 | A1 | 4/1995 | WO | WO 01/62161 | A1 | 8/2001 |
| WO | WO 95/14436 | A1 | 6/1995 | WO | WO 01/62162 | A1 | 8/2001 |
| WO | WO 95/17855 | A1 | 7/1995 | WO | WO 01/62164 | A2 | 8/2001 |
| WO | WO 95/18383 | A1 | 7/1995 | WO | WO 01/62169 | A1 | 8/2001 |
| WO | WO 95/18572 | A1 | 7/1995 | WO | WO 01/78605 | A2 | 10/2001 |
| WO | WO 95/19739 | A1 | 7/1995 | WO | WO 01/91646 | A1 | 12/2001 |
| WO | WO 95/20360 | A1 | 8/1995 | WO | WO 02/07608 | A2 | 1/2002 |
| WO | WO 95/23557 | A1 | 9/1995 | WO | WO 02/07618 | A1 | 1/2002 |
| WO | WO 95/24865 | A1 | 9/1995 | WO | WO 02/17799 | A1 | 3/2002 |
| WO | WO 95/25471 | A3 | 9/1995 | WO | WO 02/19920 | A1 | 3/2002 |
| WO | WO 95/26562 | A1 | 10/1995 | WO | WO 02/19932 | A1 | 3/2002 |
| WO | WO 95/29639 | A1 | 11/1995 | WO | WO 02/30297 | A2 | 4/2002 |
| WO | WO 96/04858 | A1 | 2/1996 | WO | WO 02/32322 | A2 | 4/2002 |
| WO | WO 96/19151 | A1 | 6/1996 | WO | WO 02/36028 | A1 | 5/2002 |
| WO | WO 96/19152 | A1 | 6/1996 | WO | WO 02/43571 | A2 | 6/2002 |
| WO | WO 96/20652 | A1 | 7/1996 | WO | WO 02/058568 | A1 | 8/2002 |
| WO | WO 96/21119 | A1 | 7/1996 | WO | WO 02/060328 | A1 | 8/2002 |
| WO | WO 96/22055 | A1 | 7/1996 | WO | WO 02/067785 | A2 | 9/2002 |
| WO | WO 96/23448 | A1 | 8/1996 | WO | WO 02/098302 | A1 | 12/2002 |
| WO | WO 96/24301 | A1 | 8/1996 | WO | WO 03/000138 | A2 | 1/2003 |
| WO | WO 96/27337 | A1 | 9/1996 | WO | WO 03/001329 | A2 | 1/2003 |
| WO | WO 96/31155 | A1 | 10/1996 | WO | WO 03/013363 | A1 | 2/2003 |
| WO | WO 96/35464 | A1 | 11/1996 | WO | WO 03/015604 | A2 | 2/2003 |
| WO | WO 96/39085 | A1 | 12/1996 | WO | WO 03/020106 | A2 | 3/2003 |
| WO | WO 96/39086 | A1 | 12/1996 | WO | WO 03/020139 | A2 | 3/2003 |
| WO | WO 96/39087 | A1 | 12/1996 | WO | WO 03/024339 | A1 | 3/2003 |

| | | |
|---|---|---|
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/089404 A2 | 7/2008 |
| WO | WO 2008/109125 A1 | 9/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000. 7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

European Search Report, Application No. 09250379.6, dated Nov. 4, 2010 (12 pages).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

* cited by examiner

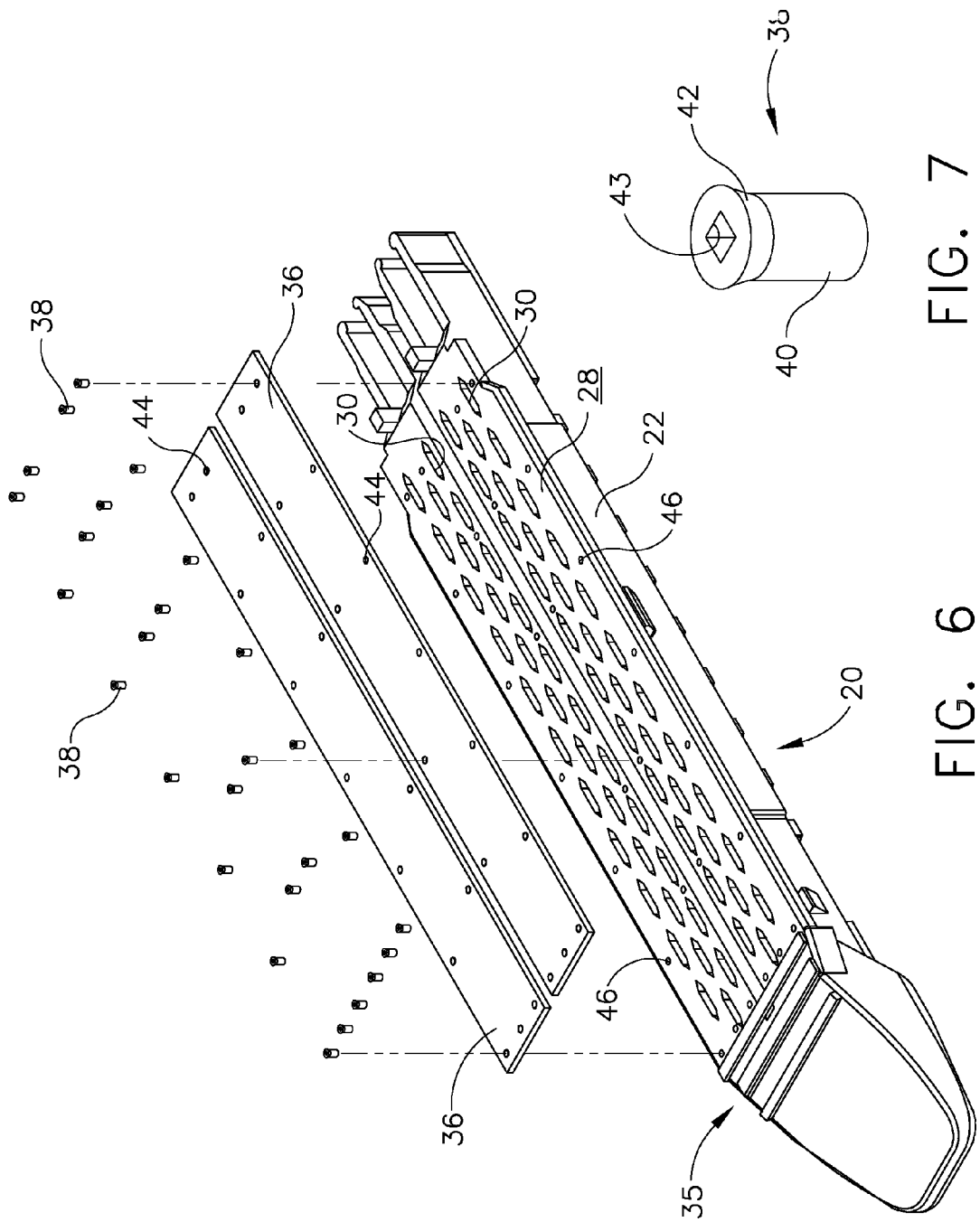

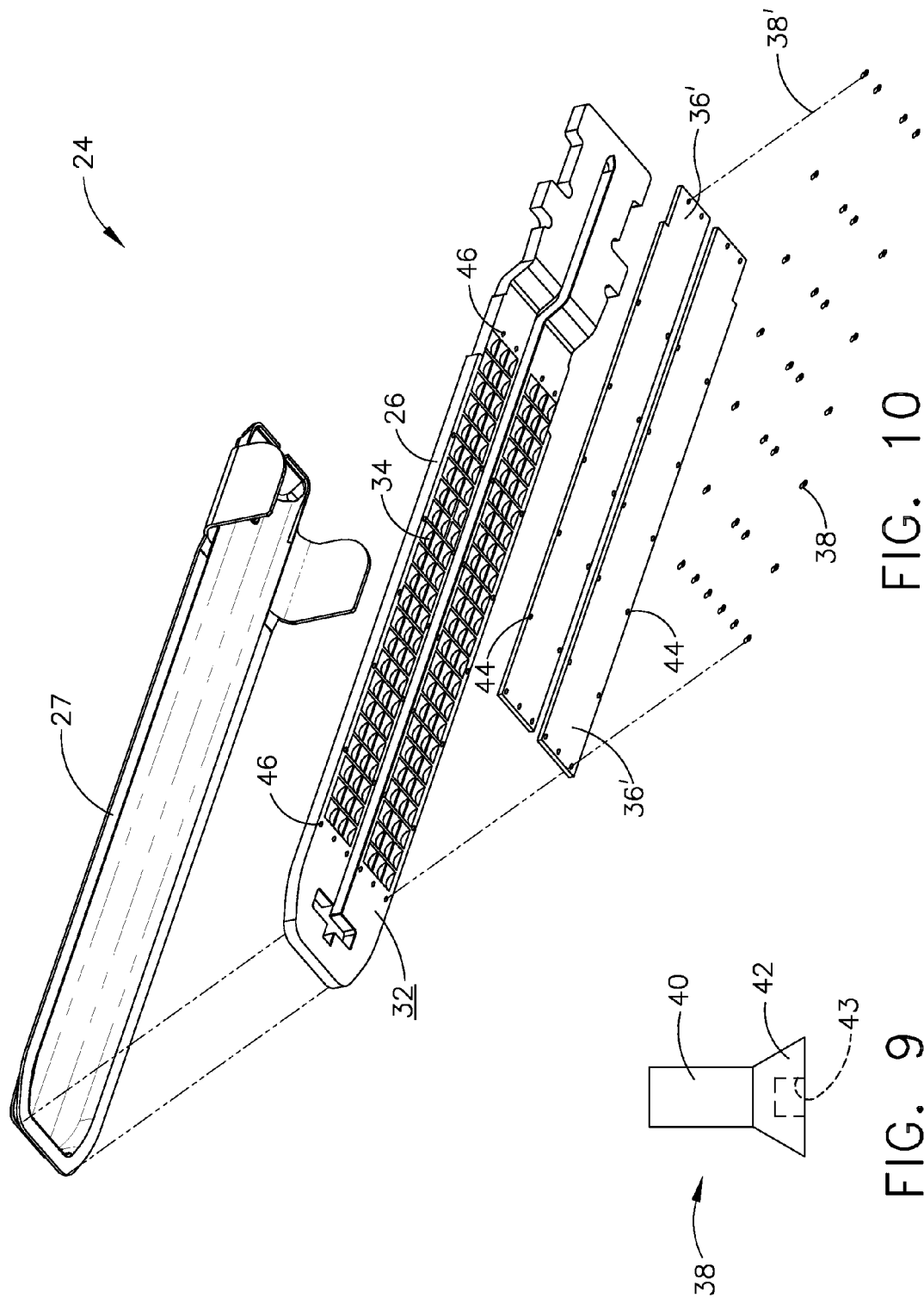

SURGICAL END EFFECTOR HAVING BUTTRESS RETENTION FEATURES

BACKGROUND i. Field of the Invention

The present invention generally relates to buttress material for a surgical instrument, and to buttress material configured to be releasably attached to an end-effector assembly of a surgical instrument.

ii. Description of the Related Art

A surgical instrument, such as a surgical stapler, for example, can be configured to deploy staples into tissue during a surgical procedure. In various embodiments, the surgical stapler can include an end-effector configured to be positioned on a distal end of the surgical stapler. The end-effector can be configured to be positioned within, and slid at least partially through, a cannula, or trocar, positioned in a wall of a patient's body such that a surgeon can utilize the end-effector to perform work within a surgical site. In various embodiments, the end-effector can comprise a first jaw member including a staple cartridge and, additionally, a second jaw member including an anvil. The first and second jaw members can be configured to be moved proximally towards each other to clamp layers of tissue therebetween and apply a compressive force thereto. In at least one embodiment, the staple cartridge can be configured to removably store staples therein and the anvil can be configured to deform the staples as they are deployed from the staple cartridge.

In some circumstances, the layers of tissue can be relatively thin, can have a high fluid content, and/or can have a non-uniform thickness, which can cause the staples to be improperly formed within the tissue. To ameliorate this problem, a piece of buttress material can be utilized to support the tissue as the tissue is being clamped and stapled. In at least one embodiment, a piece of buttress material can be releasably attached to at least one of the first and second jaw members before they are inserted into a surgical site. In various embodiments, the piece of buttress material can be utilized to distribute the compressive force applied by the anvil over the surface area of the buttress material in order to create a more uniform tissue compression profile within the tissue. In at least one embodiment, a uniform tissue compression profile can increase the likelihood that that the staples will be properly formed in the tissue.

In various embodiments, a piece of buttress material can be difficult for a surgeon to attach to the jaw members of an end-effector. In at least one embodiment, the piece of buttress material can be attached to one of the jaw members using an adhesive configured to releasably retain the piece of buttress material thereto. In such an embodiment, a surgeon must carefully align the piece of buttress material with the jaw member owing to the possibility that the adhesive may immediately bond the buttress material to the jaw member. In such circumstances, the piece of buttress material may have to be removed from the jaw member and replaced a new piece of buttress material. As a result, the surgeon can spend valuable time positioning and aligning a piece of buttress material on a jaw member of an end-effector. What is needed is an improvement over the foregoing.

SUMMARY

In at least one form of the invention, a piece of buttress material and/or an end-effector of a surgical instrument can include features which can aid a surgeon, or other clinician, in properly aligning and attaching a piece of buttress material to an end-effector. In at least one embodiment, the piece of buttress material can include at least one member extending therefrom, wherein the member can be configured to be engaged with one of a staple cavity defined in a staple cartridge and/or an anvil pocket defined in an anvil. In at least one such embodiment, the member can be friction-fit and/or press-fit within the staple cavity and/or the anvil pocket to releasably retain the piece of buttress material to one of the staple cartridge and the anvil, for example. In various embodiments, a notch or slot can be defined in one of a staple cartridge and/or an anvil wherein the notch can be configured to receive a portion of a piece of buttress material and releasably retain the piece of buttress material thereto. In at least one embodiment, a piece of buttress material can include a projection extending therefrom, wherein the projection can be configured to be releasably engaged with a cutting member channel in at least one of the staple cartridge and the anvil. In such an embodiment, the projection can be press-fit, friction-fit, and/or otherwise engaged with the channel, for example In at least one form of the invention, a piece of buttress material and an end-effector can include co-operating features, such as lips, for example, which can allow the piece of buttress material to be attached to the end-effector in a snap-fit fashion. In various embodiments, an end-effector can include resilient members extending therefrom, wherein the resilient members can be configured to contact portions of the piece of buttress material and releasably retain the buttress material to the end-effector. In at least one embodiment, one of the staple cartridge and the anvil can include a plurality of retaining members wherein portions of a piece of buttress material can be friction-fit against the retaining members to releasably retain the piece of buttress material to the staple cartridge and/or anvil.

In at least one form of the invention, a piece of buttress material can be releasably attached to a sleeve, wherein the sleeve can be configured to be slid over at least one of the staple cartridge and the anvil of an end-effector. In at least one embodiment, the piece of buttress material can include a side portion which can be attached to the sleeve and, in addition, a body portion configured to be engaged with staples when the staples are deployed from the staple cartridge. In such an embodiment, the side portion can be used to releasably retain the body portion to the sleeve. In at least one embodiment, a recess and/or perforation can be defined in the piece of buttress material intermediate the side portion and the body portion, for example, such that the body portion can be separated from the side portion. In at least one embodiment, as a result, the perforation and/or recess can allow the sleeve to be removed from the buttress material after the staples have been deployed into the body portion.

In at least one form of the invention, a package for a piece of buttress material can be utilized to quickly align and position a piece of buttress material within an end-effector. In various embodiments, a package can include a first portion, a second portion, and a piece of buttress material which can be releasably attached to the first portion. In at least one embodiment, the second portion can be configured to be moved between a first position in which it is adjacent to the piece of buttress material and a second position. In various embodiments, the piece of buttress material can be exposed when the second portion is in the second position such that the package can be positioned intermediate jaw members of an open end-effector to engage the exposed piece of buttress material to one of the jaw members of the end-effector. In various embodiments, the buttress material can include an adhesive thereon for retaining the buttress material to one of the maw members. After the piece of buttress material is engaged with one of the jaw members, the second portion can be pulled away from the end-effector to release the first portion from the piece of the buttress material.

In at least one form of the invention, a piece of buttress material can be fastened to at least one of an anvil and a staple cartridge of an end-effector. In various embodiments, an anvil and/or staple cartridge can include one or more apertures, or openings, therein which can be configured to receive one or more fasteners to retain a piece of buttress material to the anvil or staple cartridge. In various embodiments, the fasteners can be released from the apertures in the anvil and/or staple cartridge to allow the piece of buttress material to separate from the end-effector. The fasteners can also be configured to detach from the piece of buttress material and can be comprised of a bioabsorbable material such that they can be resorbed within the patient's body. In at least one embodiment, a piece of buttress material can be attached to an end effector by one or more detachable clips.

In at least one form of the invention, a piece of buttress material configured to be releasably attached to an end-effector can include an unactivated adhesive. In various embodiments, a surgeon can position and align the piece of buttress material on the end-effector multiple times without the un-activated adhesive bonding to the end-effector. Once the surgeon is satisfied with the alignment of the piece of buttress material on the end-effector, the surgeon can then apply a reactant to the un-activated adhesive. In various embodiments, the reactant can activate the adhesive and cause the adhesive to releasably bond the piece of buttress material to a portion of the end-effector. In at least one embodiment, the piece of buttress material can include a recess configured to receive an applicator such that the application of the reactant to the un-activated adhesive can be facilitated.

In at least one form of the invention, an end effector can include a retractable retention member for retaining a piece of buttress material on an end-effector. In various embodiments, the retention member can be movable between a first, or distal, position and a second, or proximal, position. In at least one embodiment, the flexible member can be operably engaged with a handle portion such that a surgeon can utilize the handle portion to retract the flexible member relative to the end-effector. In various embodiments, the flexible member can hold the piece of buttress material in position while staples are deployed through the buttress material. In at least one embodiment, the retention member can be retracted relative to the end effector such that the buttress material can be disengaged from the end effector and the end effector can be removed from the surgical site.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 6 is an exploded perspective view of the staple cartridge and the buttress material of FIG. 5;

FIG. 7 is a perspective view of a connection member configured to be used with the end-effector assembly of FIG. 4;

FIG. 9 is a side view of the connection member of FIG. 7;

FIG. 10 is an exploded perspective view of the anvil and the buttress material of FIG. 8;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 1:
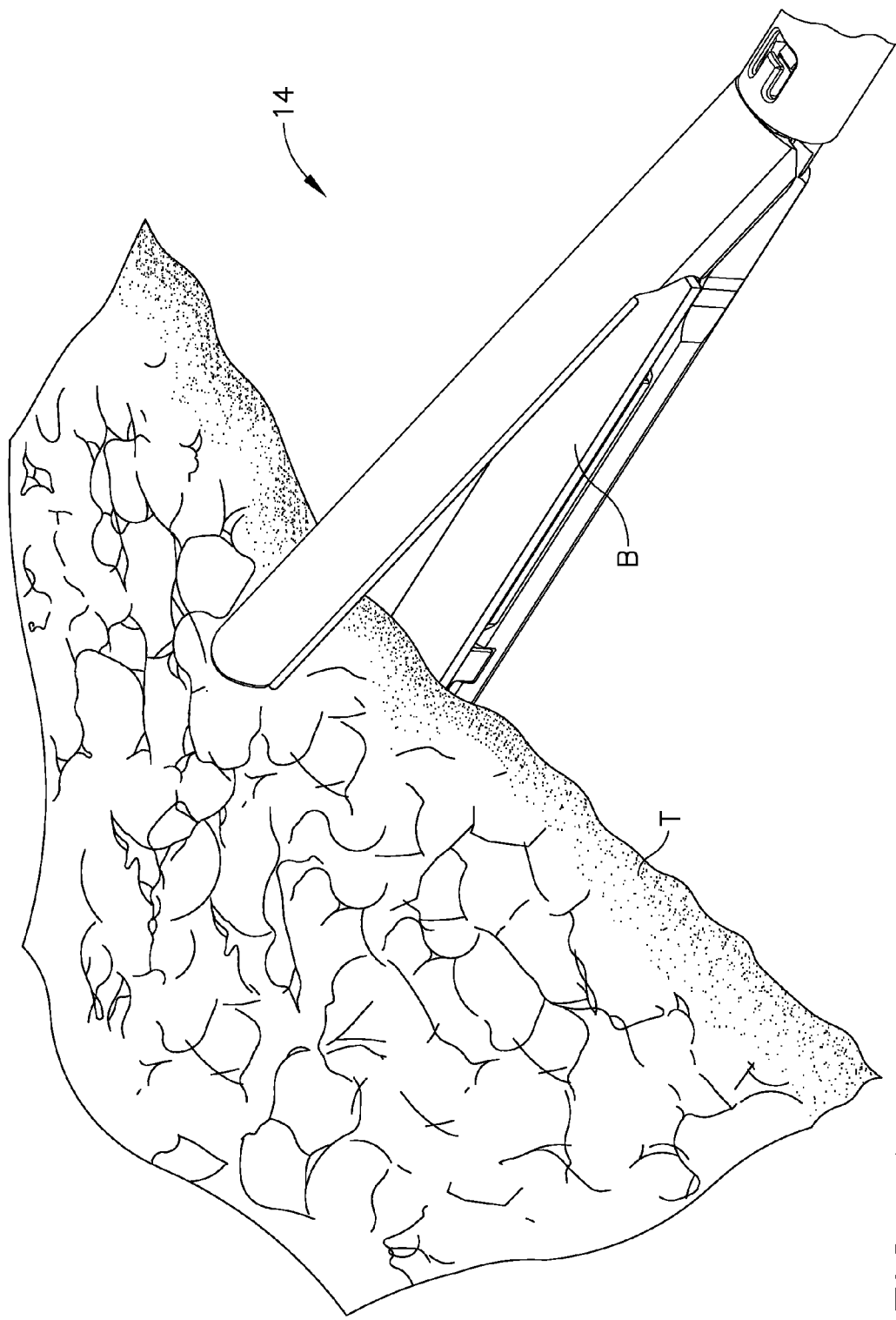
FIG. 1 is a perspective view of an end-effector assembly configured to engage, cut, staple, and apply a piece of buttress material to tissue in accordance with one non-limiting embodiment of the present invention.
Figure 2:
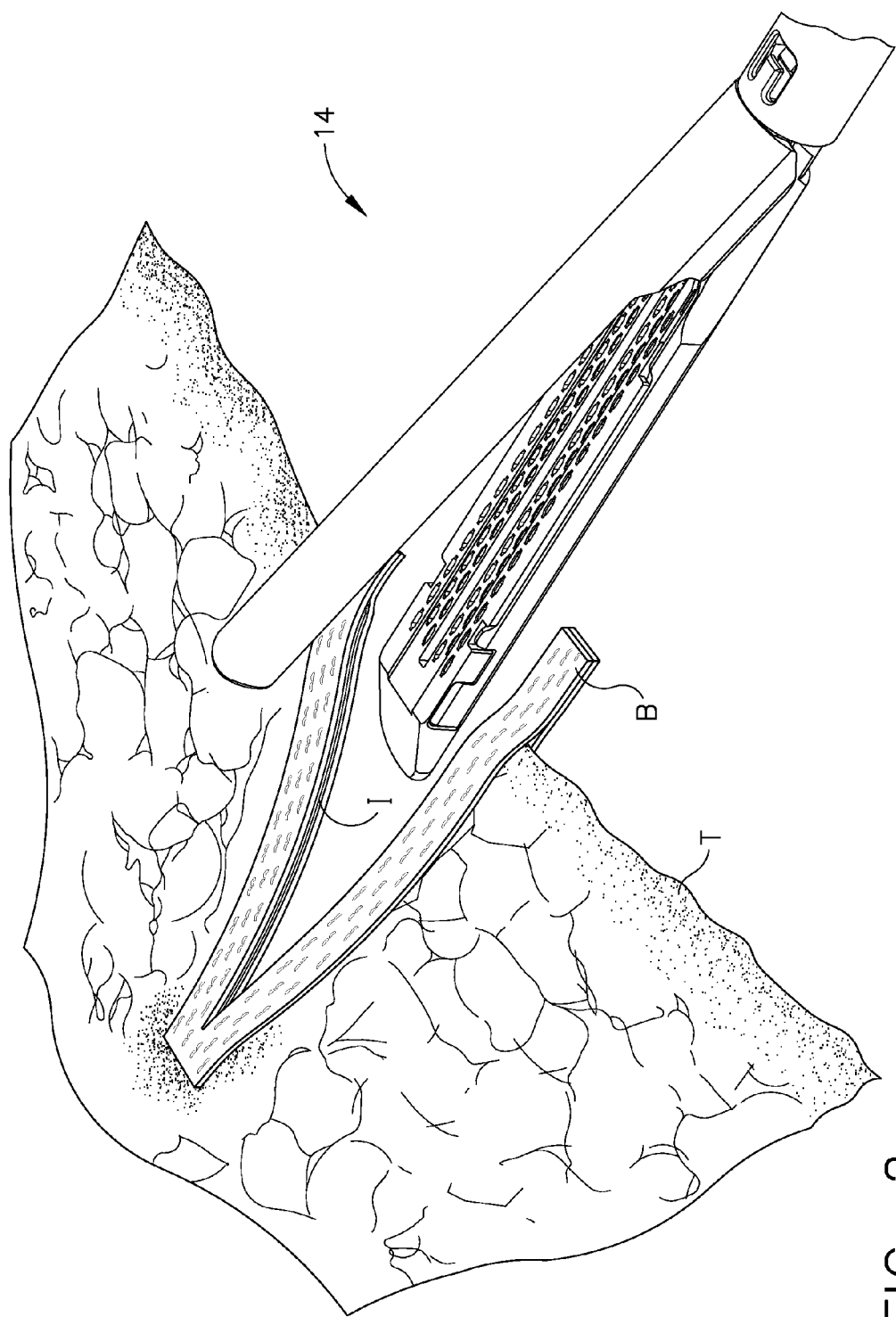
FIG. 2 is a perspective view of the end-effector assembly of FIG. 1 after the end-effector has been utilized to engage, cut, staple, and apply the piece of buttress material to the tissue in accordance with one non-limiting embodiment of the present invention.
Figure 3:
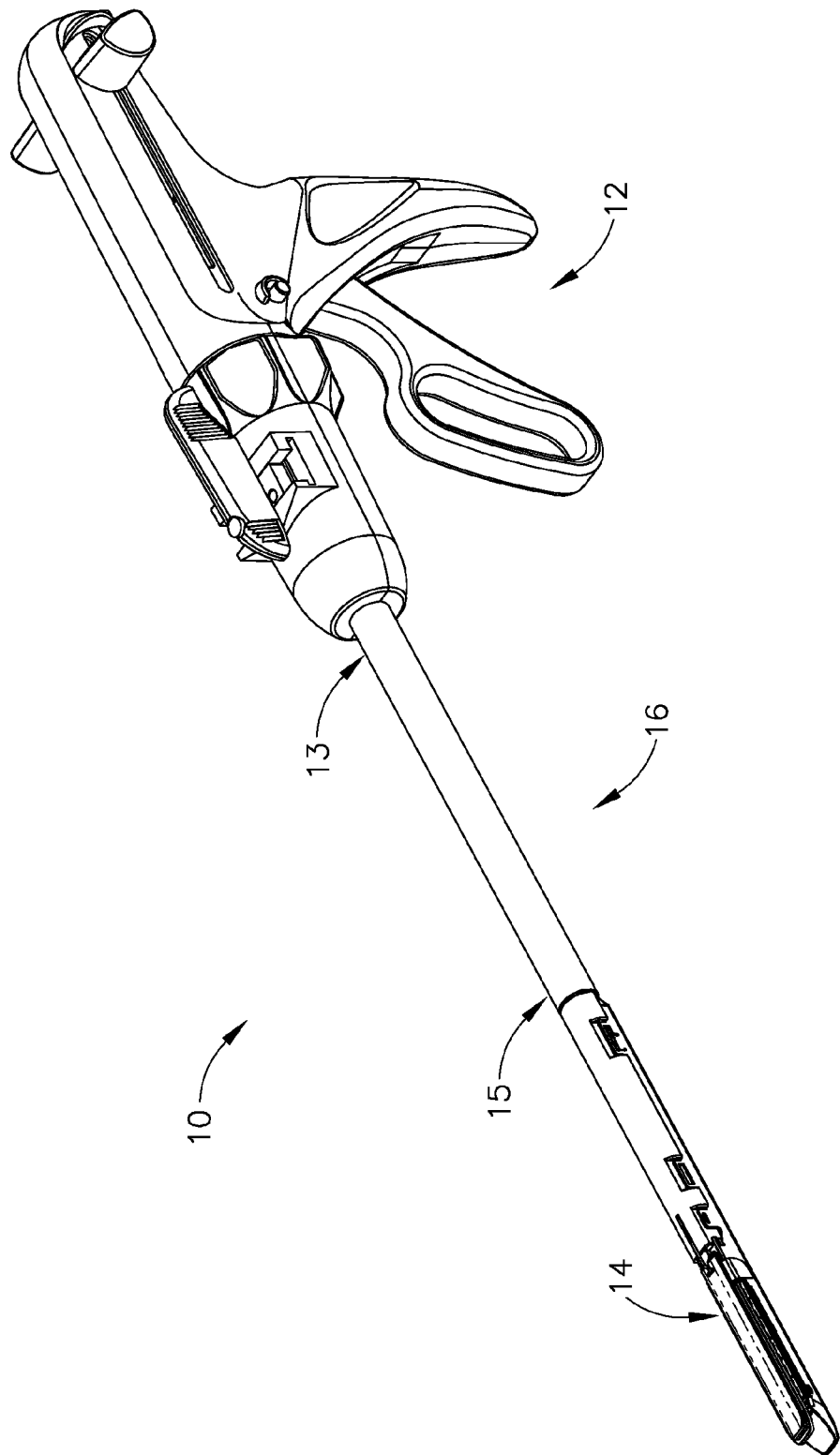
FIG. 3 is a perspective view of an end-effector assembly attached to a distal end of a surgical instrument in accordance with one non-limiting embodiment of the present invention.
Figure 4:
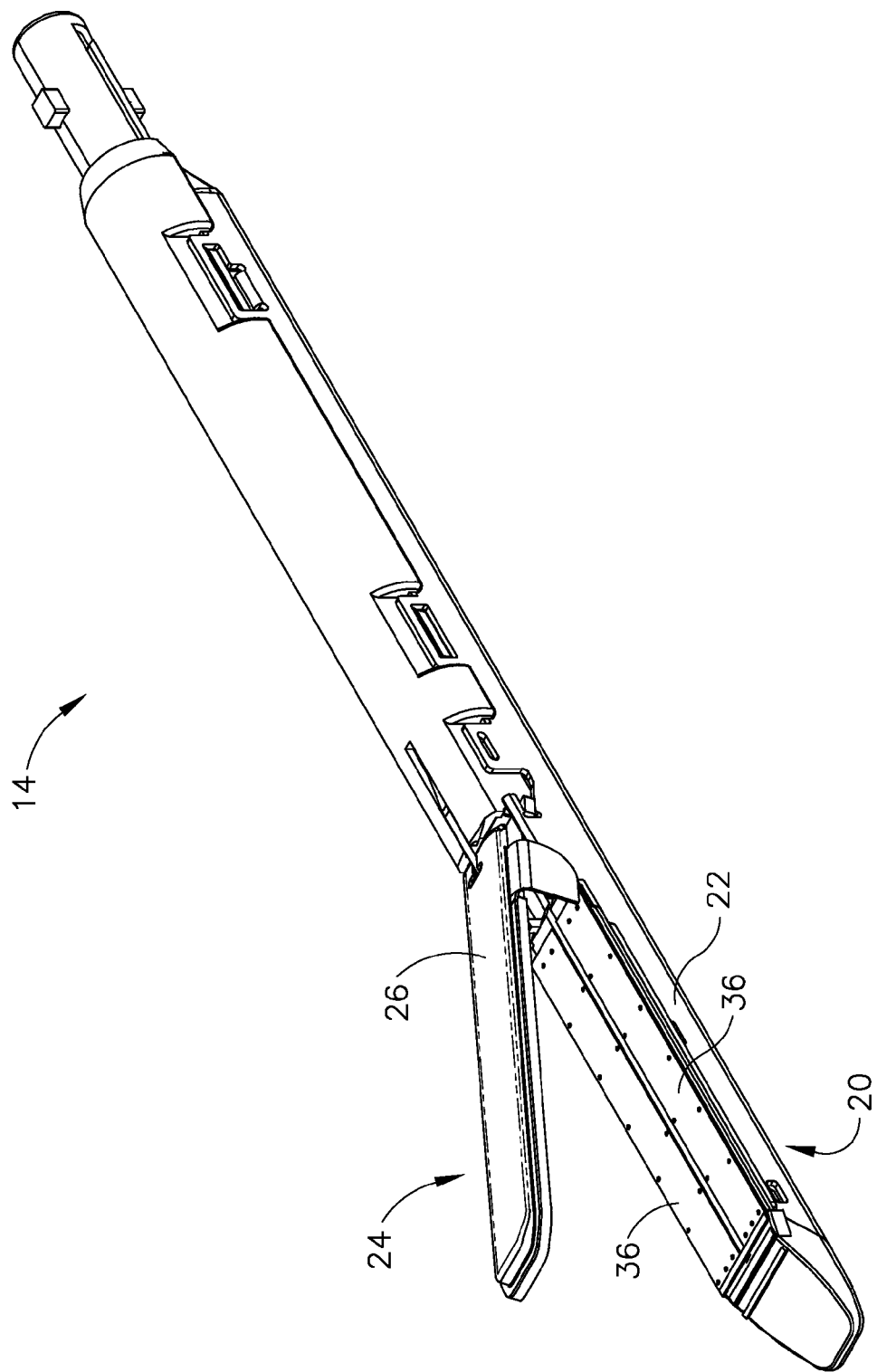
FIG. 4 is a perspective view of an end-effector assembly including at least one piece of buttress material, wherein the end-effector assembly is in an open configuration in accordance with one non-limiting embodiment of the present invention.
Figure 5:
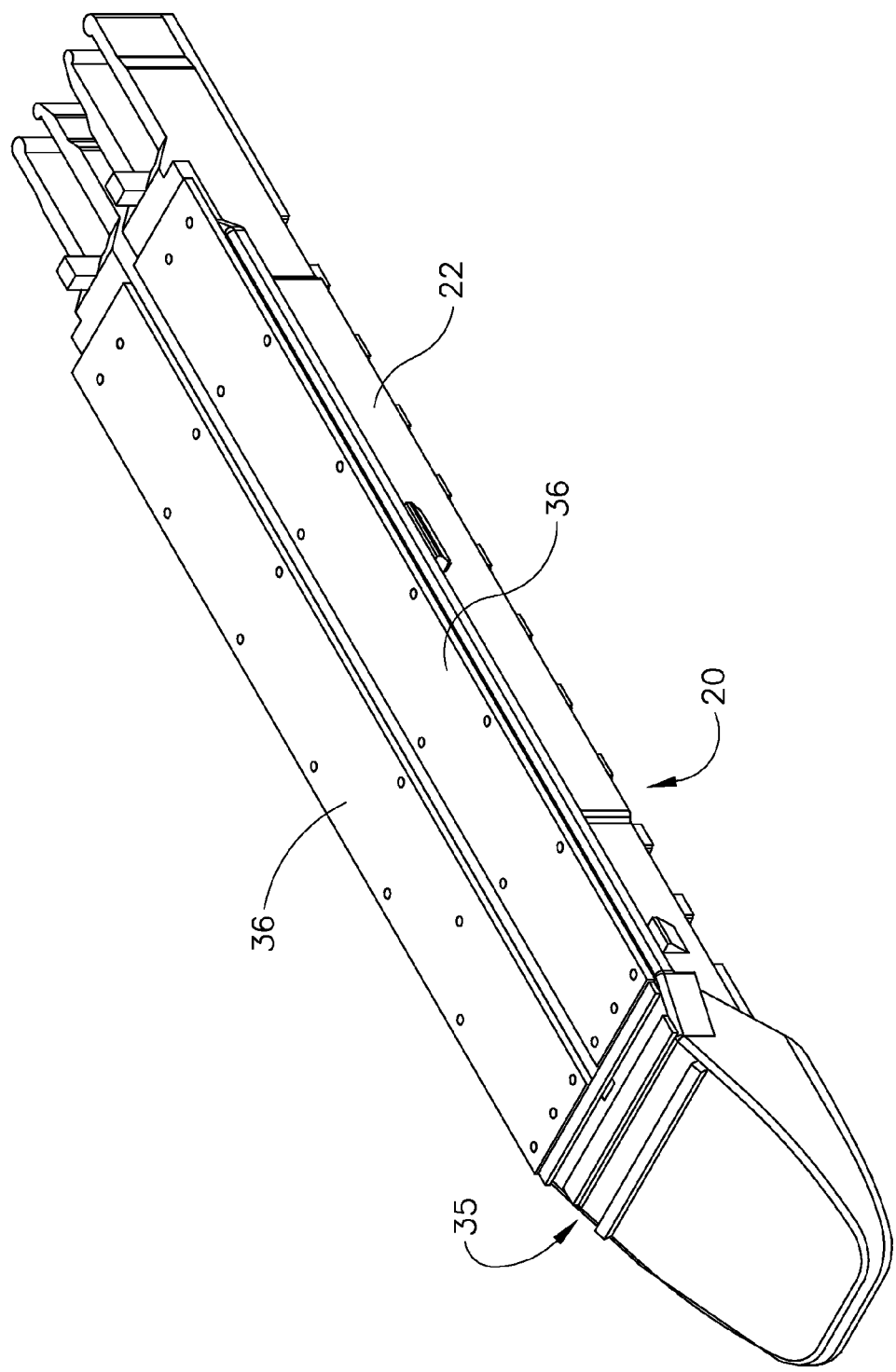
FIG. 5 is a perspective view of a staple cartridge of the end-effector assembly of FIG. 4, wherein the buttress material is releasably retained thereto.
Figure 8:
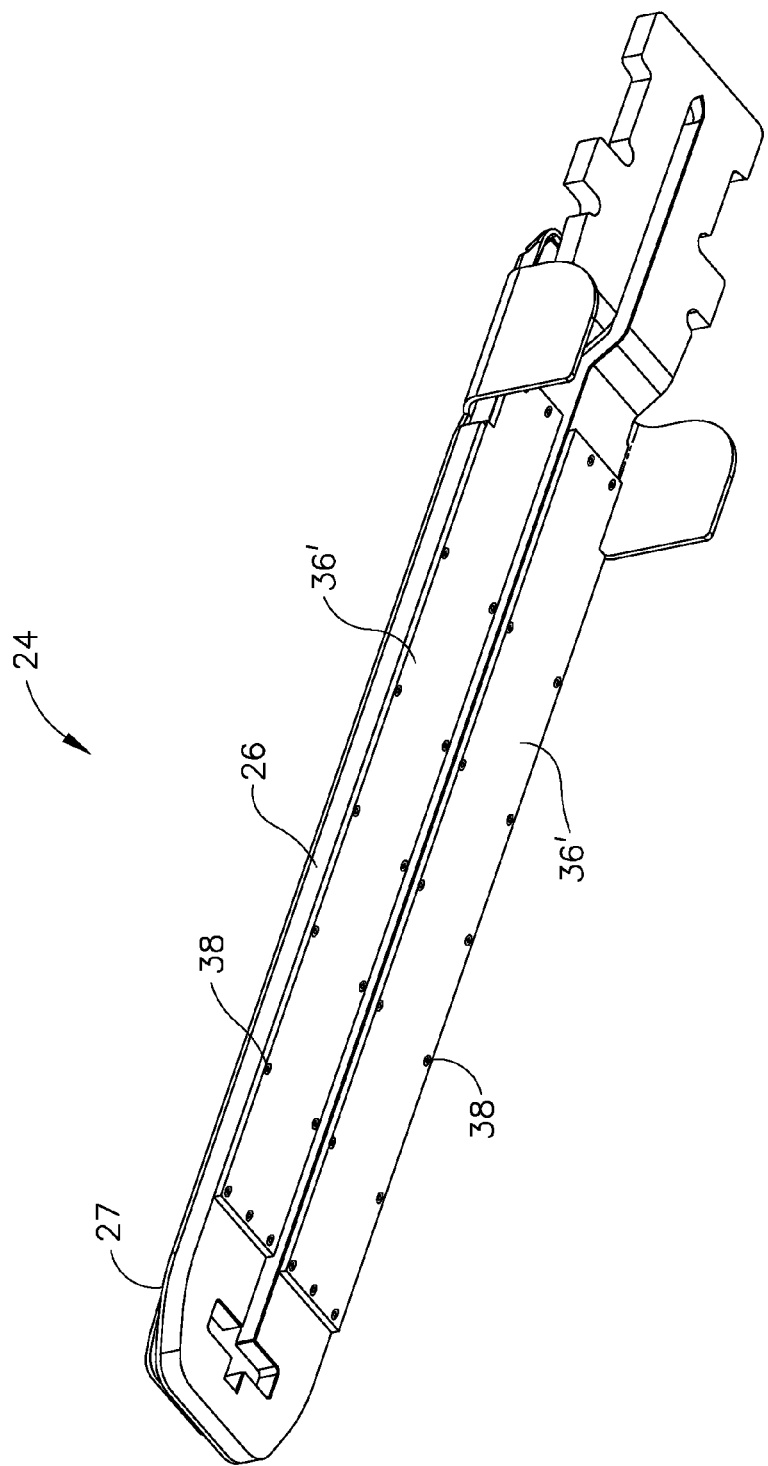
FIG. 8 is a perspective view of an anvil of the end-effector assembly of FIG. 4, wherein the anvil has at least one piece of buttress material releasably retained thereto.

In various embodiments, referring to FIGS. 1-2, an end-effector of a surgical instrument can include at least one piece of buttress material "B" releasably attached thereto. In at least one embodiment, the end-effector can be configured to engage and clamp tissue "T", deploy staples into the tissue, and cut the tissue and the piece of buttress material. In such an embodiment, the end-effector can then be removed from the tissue leaving the staples and the piece of buttress material attached to the tissue on either side of an incision "I". In various embodiments, a surgical instrument can include a handle assembly, an end-effector assembly, an instrument shaft, and at least one piece of buttress material releasably attached to the end-effector assembly. In at least one embodiment, referring to FIG. 3, handle assembly 12 can be attached to a first, or proximal, end 13 of instrument shaft 16 and, additionally, end-effector assembly 14 can be configured to be attached to a second, or distal, end 15 of instrument shaft 16. In various embodiments, end-effector assembly 14 and at least a portion of instrument shaft 16 can be configured to be positioned within, and inserted at least partially through, a cannula, or trocar, in a patient's body during a minimally invasive surgical procedure. Various surgical instruments are described in further detail in U.S. patent application Ser. No. 11/329,020, entitled SURGICAL INSTRUMENT HAVING AN ARTICULATING END EFFECTOR, which was filed on Jan. 10, 2006; U.S. patent application Ser. No. 11/343,321, entitled SURGICAL CUTTING AND FASTENING INSTRUMENT WITH CLOSURE TRIGGER LOCKING MECHANISM, which was filed on Jan. 31, 2006; and U.S. patent application Ser. No. 11/529,935, entitled SURGICAL STAPLES HAVING ATTACHED DRIVERS AND STAPLING INSTRUMENTS FOR DEPLOYING THE SAME, which was filed on Sep. 29, 2006, the entire disclosures of which are hereby incorporated by reference herein.

In various embodiments, an end-effector assembly of a surgical instrument can include a first jaw member and a second jaw member wherein at least one of the first and second jaw members can be configured to be moved relative to the other jaw member such that tissue can be clamped therebetween. In various embodiments, referring to FIGS. 4-11, first jaw member 20 can include staple cartridge 22 and, additionally, second jaw member 24 can include anvil 26. In at least one embodiment, staple cartridge 22 can include deck 28 having a plurality of staple cavities 30 defined therein. Anvil 26 can include anvil cover 27 and anvil face 32, wherein anvil face 32 can have a plurality of anvil pockets 34 defined therein. In various embodiments, each staple cavity 30 can be configured to removably store a staple therein and each anvil pocket 34 can be configured to deform at least a portion of the staple as the staple is deployed. In various embodiments, at least one of the staple cartridge and the anvil can comprise one or more gripping features, or ridges, 35 which can be configured to hold the tissue within the end effector.

Further to the above, referring to FIGS. 4-11, end-effector assembly 14 can include at least one piece of buttress material 36 and/or 36' which can be configured to be positioned intermediate the first and second jaw members and can be releasably retained to one of deck 28 and/or face 32, for example. In at least one embodiment, a surface on the piece of buttress material can be configured to contact tissue as the tissue is clamped between the first and second jaw members. In such an embodiment, the buttress material surface can be used to distribute the compressive clamping force over the tissue, remove excess fluid from the tissue, and/or improve the purchase of the staples. In various embodiments, one or more pieces of buttress material can be positioned within the end-effector assembly. In at least one embodiment, referring to FIG. 11, one piece of buttress material 36a can be attached to staple cartridge 22 and one piece of buttress material 36a' can be attached to anvil 24. In at least one other embodiment, two pieces of buttress material 36 can be positioned on deck 28 and one piece of buttress material 36' can be positioned on face 32, for example. In other various embodiments, any suitable number of pieces of buttress material can be situated within an end-effector assembly. In any event, in various embodiments, the piece(s) of buttress material can be comprised of a material such as, a bioabsorbable material, a biofragmentable material, and/or a dissolvable material, for example, such that the buttress material can be absorbed, fragmented, and/or dissolved during the healing process. In at least one embodiment, the piece(s) of buttress material can be at least partially comprised of a therapeutic drug which can be configured to be released over time to aid the tissue in healing, for example. In further various embodiments, the piece(s) of buttress material can include a non-absorbable and/or non-dissolvable material, for example.

In various embodiments, referring to FIGS. 6, 7, 9, and 10, an end-effector assembly can include at least one connection member or fastener which can be utilized to releasably retain a piece of buttress material to at least one of an anvil and a staple cartridge, for example. In at least one embodiment, each connection member, such as connection member 38, for example, can include body 40, wherein body 40 can be cylindrically-shaped, for example. In at least one such embodiment, connection member 38 can also include an outwardly flared head portion 42 configured to prevent, or at least inhibit, the connection member from sliding through an aperture or opening 44 in the piece of buttress material. In other various embodiments, a connection member can include any other suitably shaped configuration to retain a piece of buttress material to an end effector. In at least one embodiment, one or more connection members can comprise a clasp which can be configured to detachably retain the buttress material to a staple cartridge and/or anvil.

In various embodiments, referring to FIGS. 7 and 9, head portion 42 can include recess 43, wherein recess 43 can be configured to receive a driver, a press, or any other suitable device. In at least one embodiment, the driver or press can be engaged with recess 43 and utilized to insert connection members 38 through the piece of buttress material and into engagement with one of staple cartridge deck 28 and anvil face 32, for example. In at least one such embodiment, deck 28 and/or face 32 can include apertures 46 which can be configured to receive at least a portion of the connection members, such as body 40, for example. In various embodiments, the outer perimeter of body 40 and the inner perimeter of an aperture 46 can cooperate to retain connection members 38 to one of the anvil and the staple cartridge in a friction-fit or press-fit manner. Further to the above, referring to FIGS. 6 and 10, a piece of buttress material can include pre-formed apertures 44 which can be configured to allow connection members 38 to pass therethrough into apertures 46, for example. In at least one embodiment, piece of buttress material 36 can be positioned adjacent to, or against, one of deck 28 and face 32 such that buttress apertures 44 can be axially aligned with apertures 46. In such circumstances, connection members 38 can then be positioned through buttress apertures 44 and into apertures 46 to releasably retain the piece of buttress material to one of deck 28 and face 32.

Figure 9A:
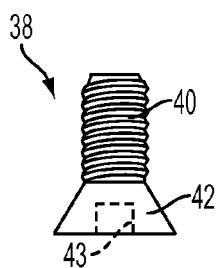
FIG. 9A is a side view of the connection member of FIG. 7.
Figure 11:
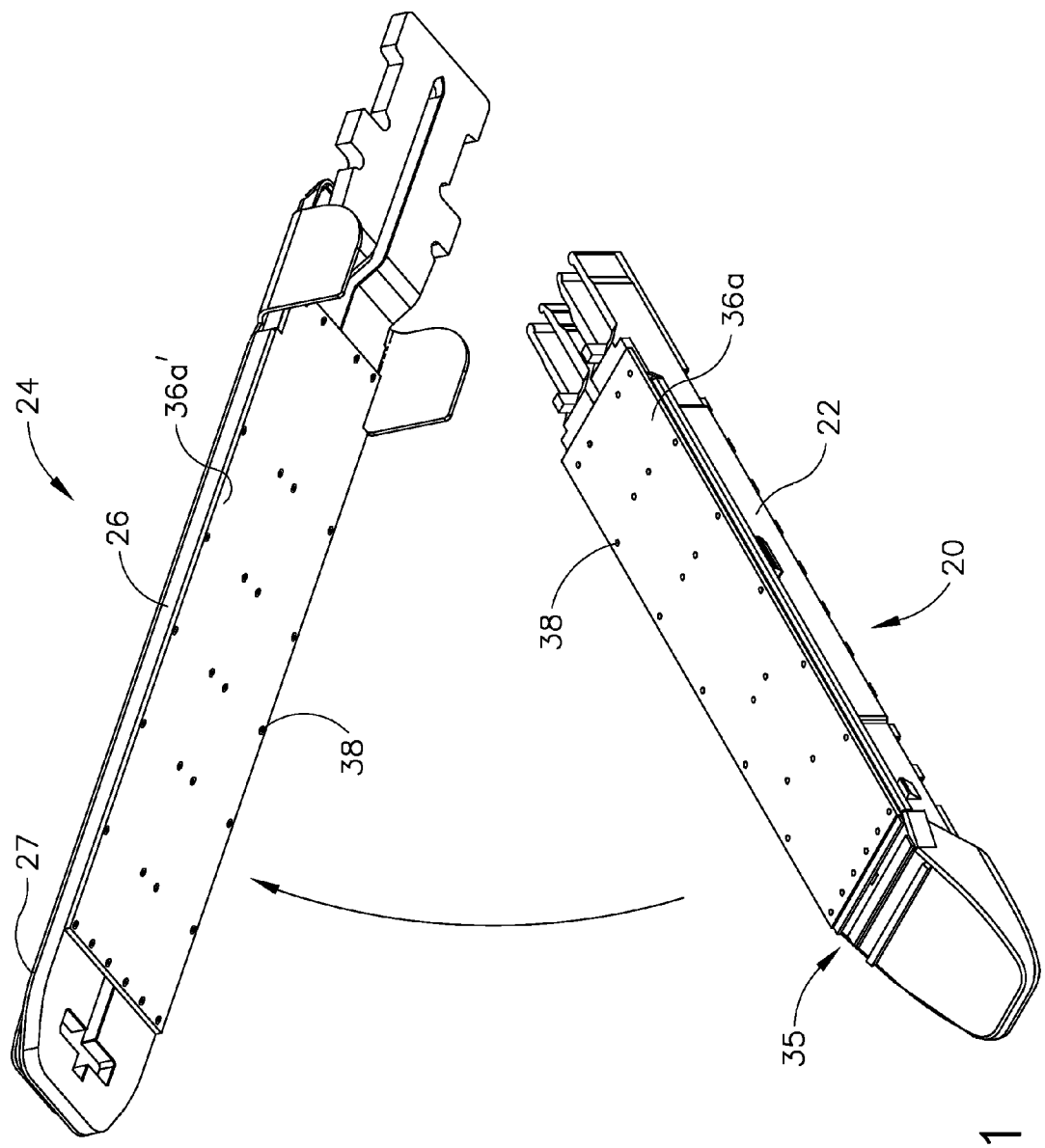
FIG. 11 is a perspective view of a staple cartridge and an anvil of an end-effector assembly with pieces of buttress material attached thereto in accordance with one non-limiting embodiment of the present invention.

Further to the above, referring to FIG. 9A, a connection member can include threads which can be threadably engaged with an aperture in a staple cartridge and/or anvil, for example. In various embodiments, such threads can include self-tapping threads and/or they can be configured to threadably engage threads within the aperture. In embodiments which utilize self-tapping connection members, the connection members can be used in conjunction with a piece of buttress material, a staple cartridge, and/or anvil which do not have pre-formed or pre-bored apertures defined therein. In either event, the purchase between the connection members and the anvil or staple cartridge apertures may be sufficient to hold the buttress material in place, yet allow the buttress material to strip away from the staple cartridge and/or deck when appropriate. In at least one embodiment, outwardly flared head portion 42 can be configured to be countersunk into a bevel surrounding an aperture 46 in order to provide a smooth, or at least substantially smooth, tissue-contacting surface on the piece of buttress material and reduce the possibility that tissue may be caught or snagged on a connection member.

In various embodiments, connection members can be configured to be released from an end effector and deployed along with a piece of buttress material. In at least one embodiment, head portions of the connection members can be configured to be separated from body portions of the connection members such that the head portions can be deployed with the piece of buttress material while the body portions remain attached to the end effector. In other various embodiments, the entirety of the connection members can remain engaged with the end effector when the piece of buttress material is detached from the end-effector. In any event, in at least one embodiment, the connection members can be at least partially comprised of at least one of a bioabsorbable material, a biofragmentable material, and a dissolvable material such that the connection members can be absorbed, fragmented, and/or dissolved within the body. In various embodiments, the connection members comprised of a therapeutic drug which can be configured to be released over time to aid the tissue in healing, for example. In further various embodiments, the connection members can include a non-absorbable and/or non-dissolvable material, for example, such as a plastic.

In various embodiments, the connection members can be arranged in any suitable pattern or configuration. In at least one embodiment, the connection members can be situated around the outer perimeter of piece of buttress material 36, for example. In at least one embodiment, the connection members can be positioned proximate to one or more sides and/or ends of the piece of buttress material, for example, to prevent, or at least assist in preventing, the buttress material from peeling away from the staple cartridge deck and/or the anvil face when the end-effector is inserted through a trocar or engaged with tissue. In various embodiments, the connection members can be used in conjunction with any suitable adhesive, such as cyanoacrilate, for example, to releasably retain the piece of buttress material, or at least a portion of the buttress material, to the end effector. In at least one embodiment, the adhesive can be applied to connection members prior to the connection members being engaged with the apertures in the piece of buttress material, staple cartridge, and/or anvil.

Figure 12:
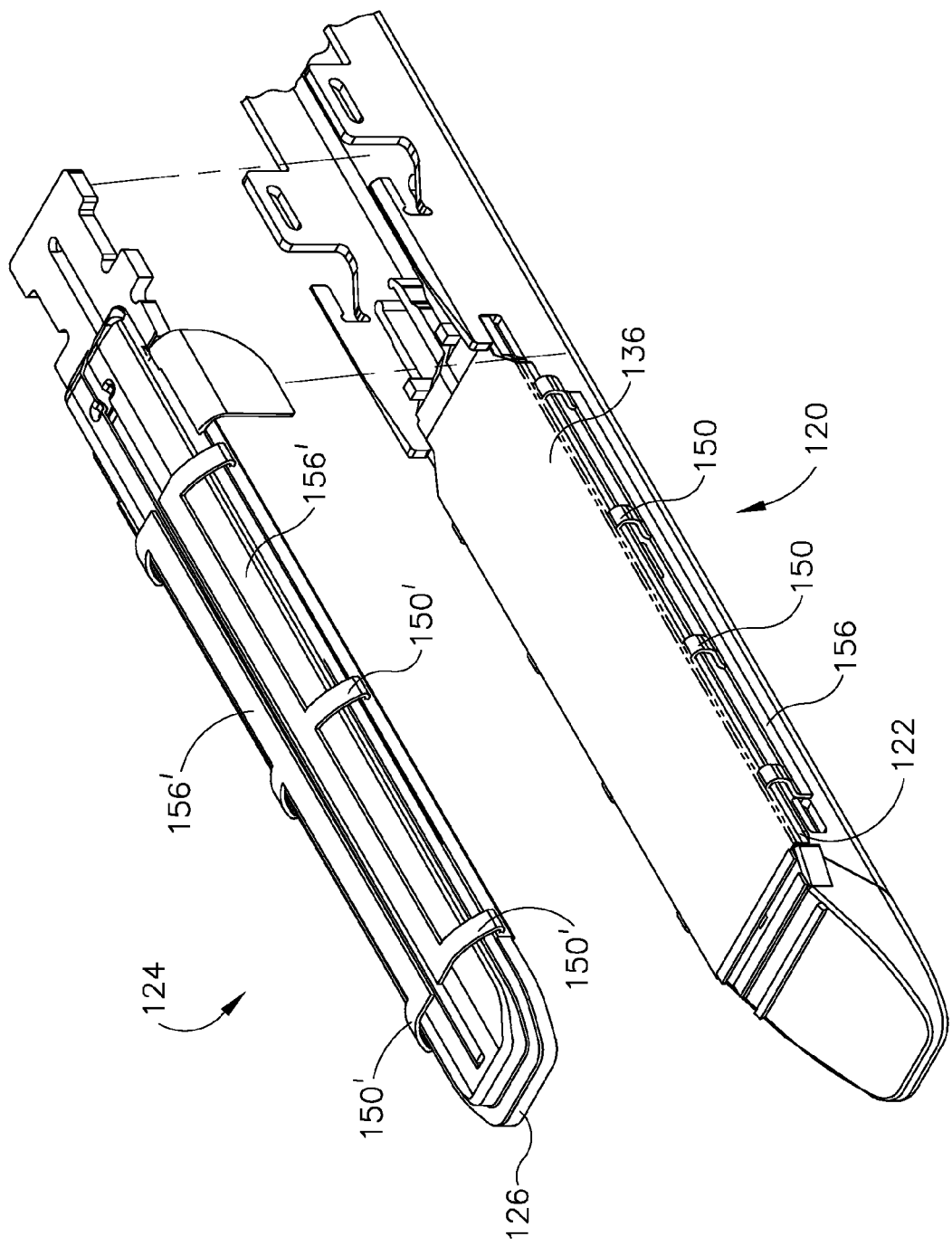
FIG. 12 is an exploded view of an end-effector assembly including a staple cartridge and an anvil in accordance with one non-limiting embodiment of the present invention.
Figure 13:
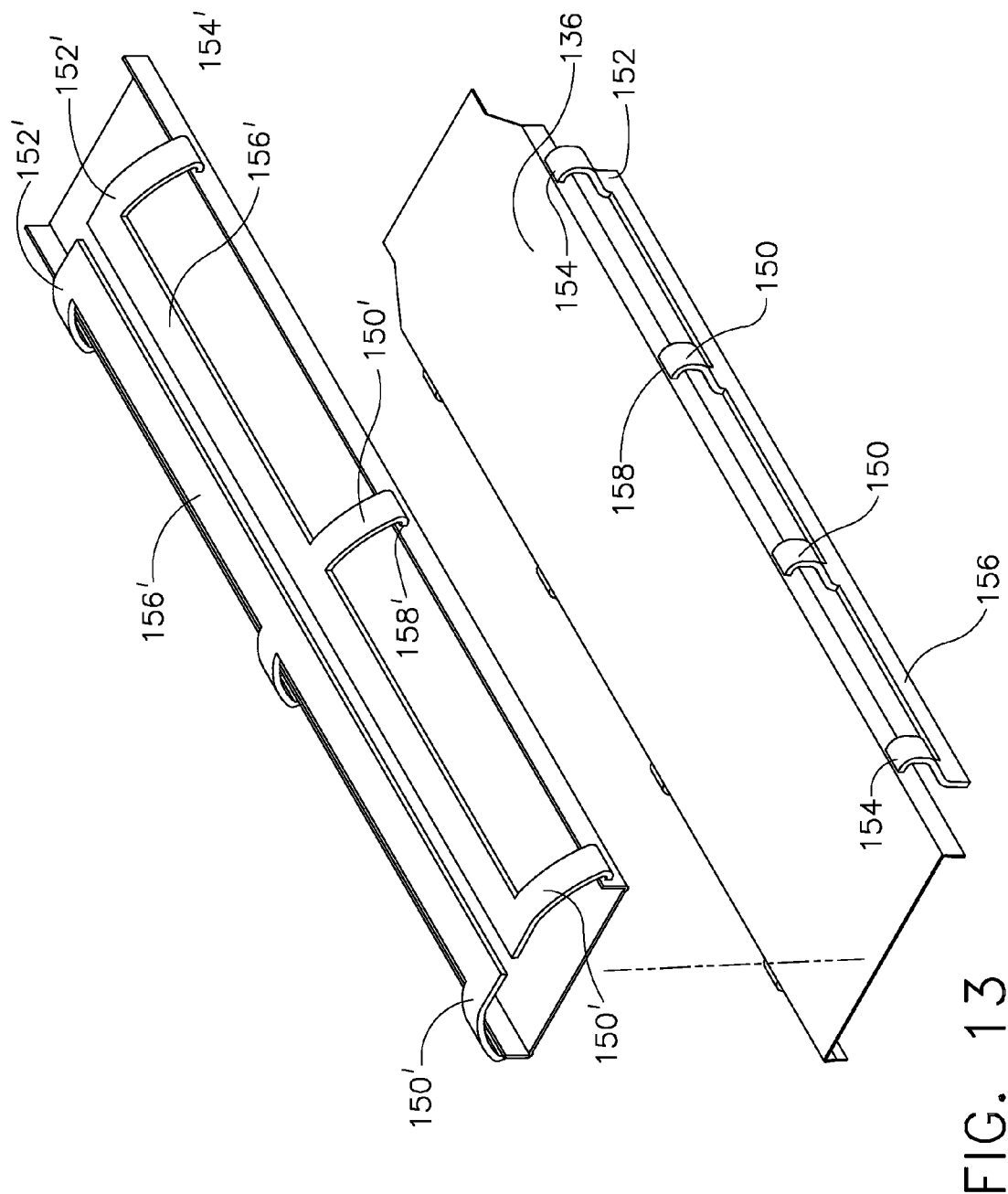
FIG. 13 is an exploded view of the end-effector assembly of FIG. 12 with some components removed.
Figure 14:
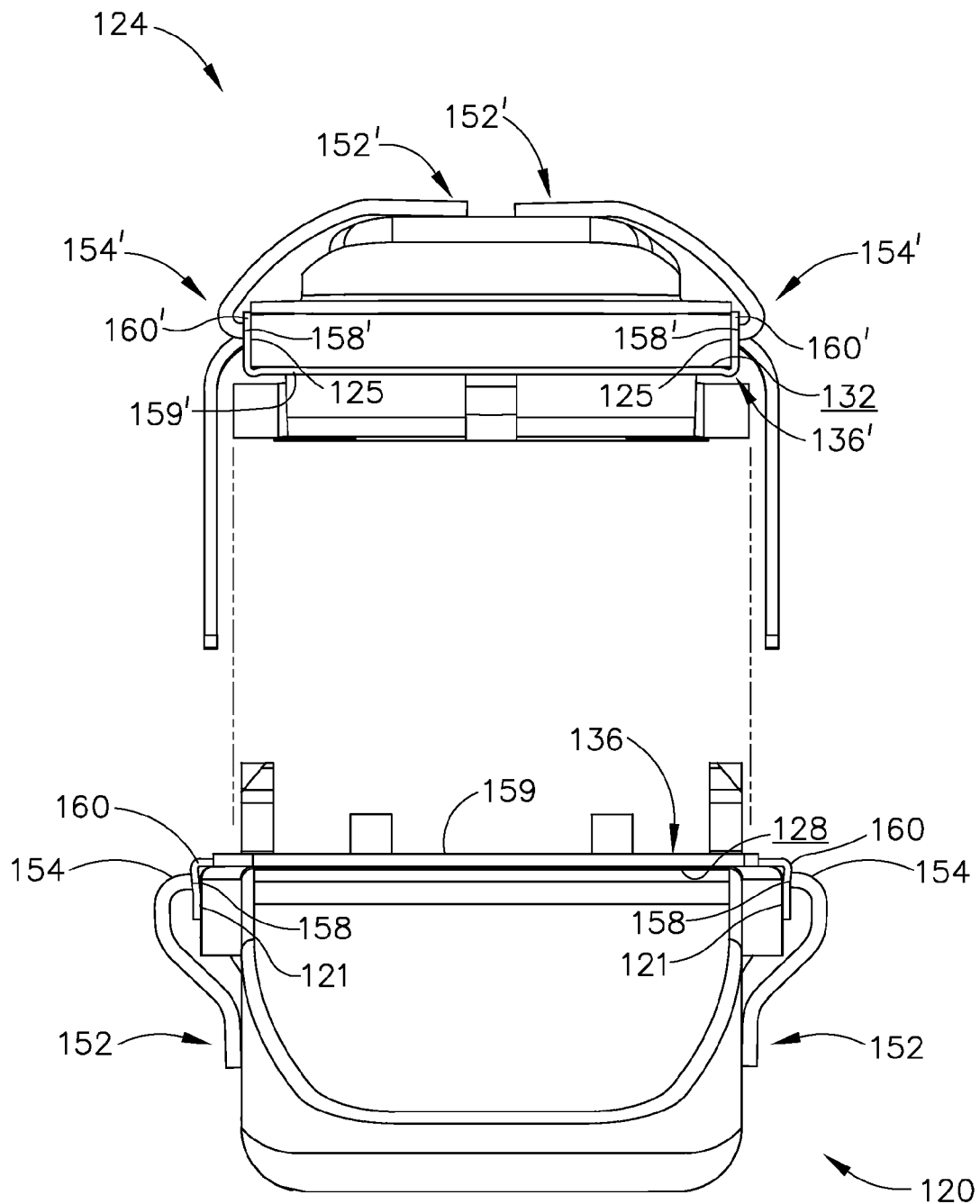
FIG. 14 is a front view of the end-effector assembly of FIG. 12.
Figure 15:
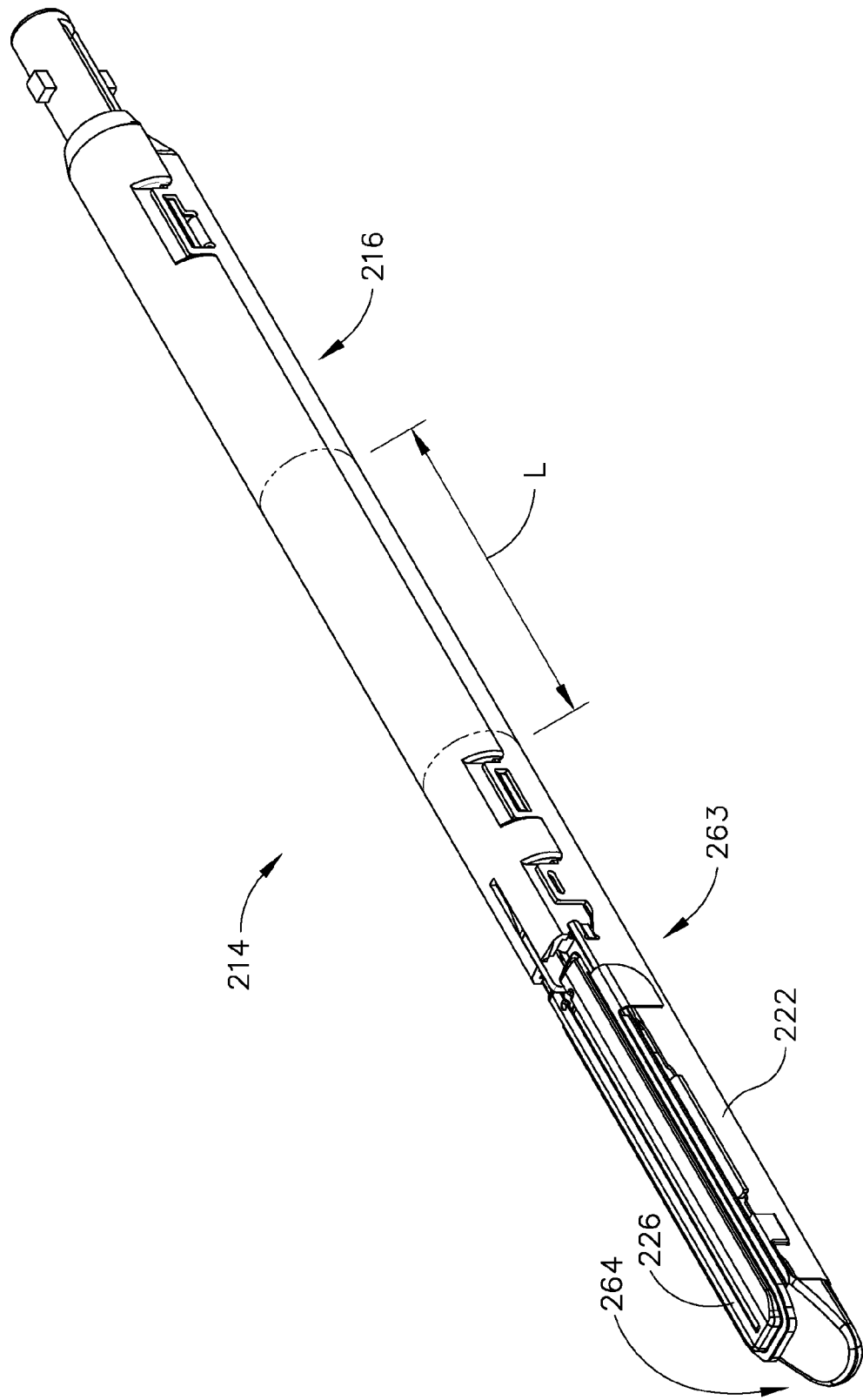
FIG. 15 is a perspective view of an end-effector assembly in accordance with another non-limiting embodiment of the present invention.
Figure 16:
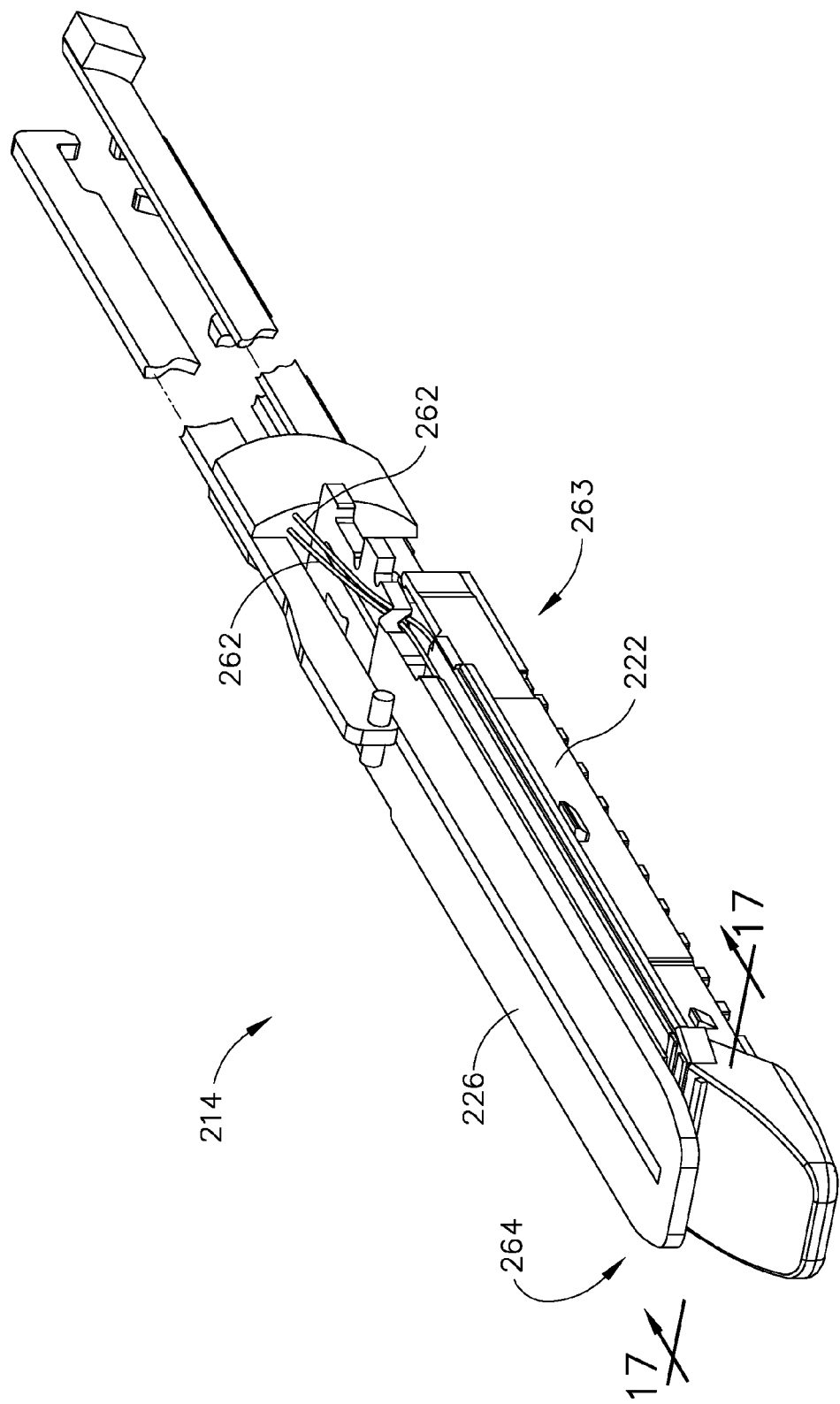
FIG. 16 is a partial perspective view of the end-effector assembly of FIG. 15 with some components removed, wherein the end-effector assembly includes a retractable member configured to releasably retain at least one piece of buttress material.
Figure 17:
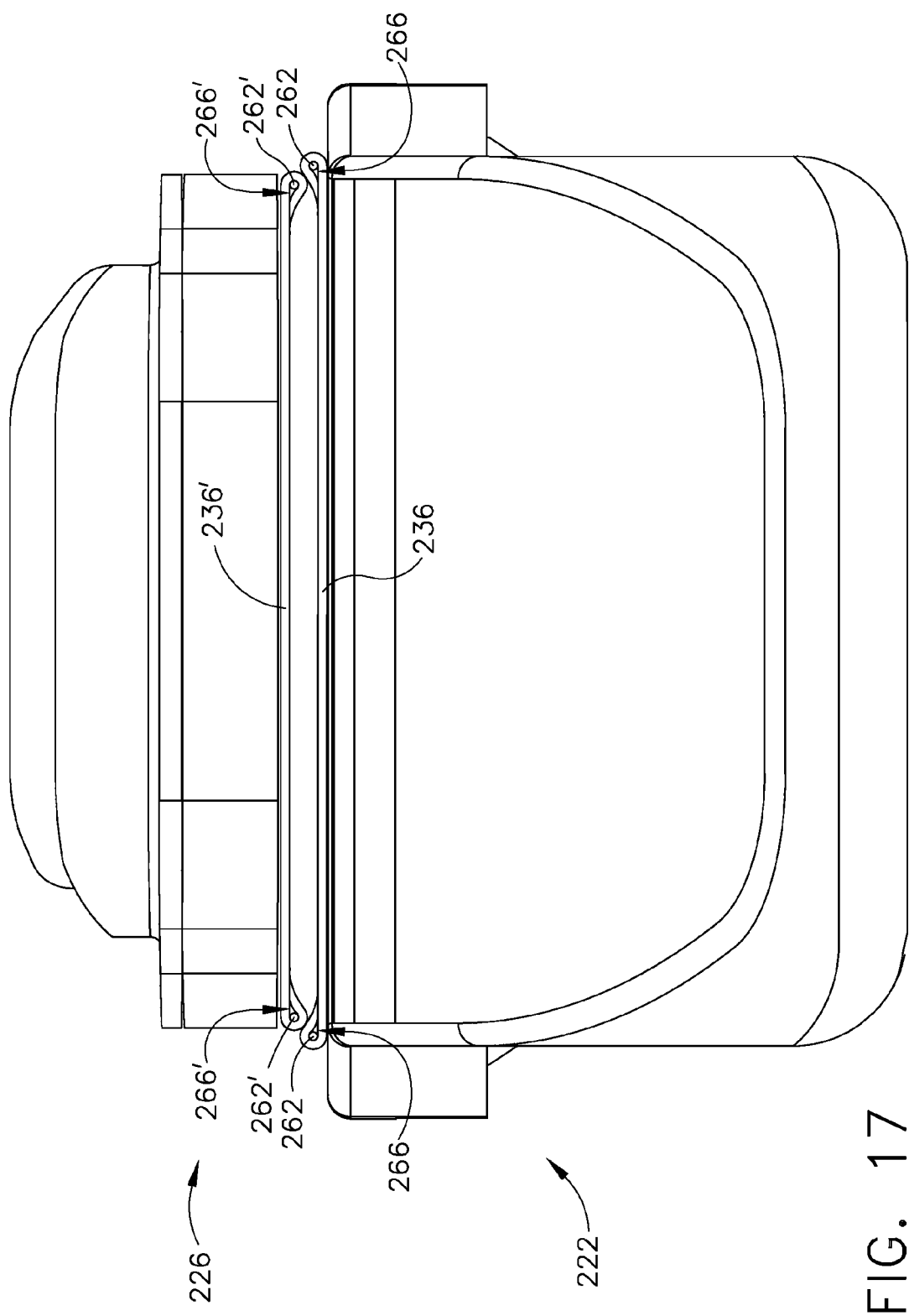
FIG. 17 is an end view of the end-effector assembly of FIG. 15 taken along line 17-17 in FIG. 16.
Figure 18:
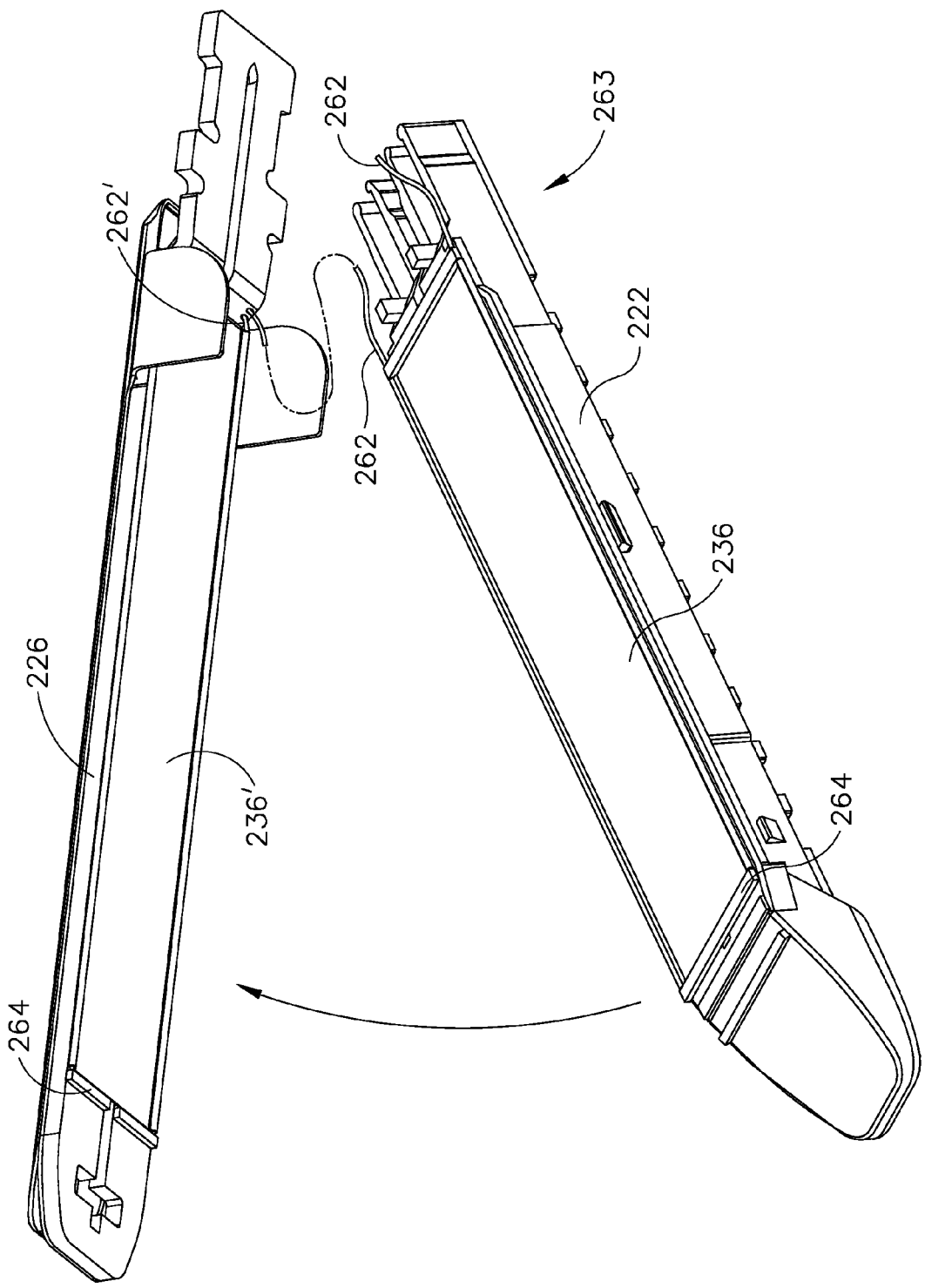
FIG. 18 is an exploded partial perspective view of the end-effector assembly of FIG. 15.

In various embodiments, referring to FIGS. 12-14, at least one resilient member can be utilized to releasably retain a piece of buttress material to a staple cartridge and/or anvil of an end effector. In at least one embodiment, at least one resilient member, such as resilient members 150 or 150', for example, can include a first end, such as first ends 152 or 152', configured to be attached to, or integrally formed with, at least one of first and second jaw members 120 and 124. In at least one embodiment, each resilient member 150 can include a second end, such as second ends 154 or 154', for example, configured to contact and releasably retain a piece of buttress material, such as piece of buttress material 136 or 136', to at least one of the first and second jaw members. In various embodiments, second end 154 can include tip 158 which can be configured to grip at least a portion of piece of buttress material 136, for example. In various embodiments, tip 158 can be contoured and/or configured to include a rough or ribbed surface, for example, in order to frictionally engage the piece of buttress material.

In various embodiments, referring again to FIGS. 12-14, a plurality of resilient members can be provided on at least two sides of a jaw member to retain side portions of the piece of buttress material to the jaw member. In at least one embodiment, first ends 152 of each individual resilient member 150 can be attached to one another by a connecting member, such as connecting member, or bar, 156 or 156', for example. In various embodiments, connecting member 156 can be attached to second jaw member 124 such that connection member 156 can provide support to resilient members 150. In other various embodiments, a plurality of resilient members 150 can be attached to at least one of the first and second jaw members without the use of a connecting member. In such an embodiment, the first ends of the resilient members can be attached directly to one of the first and second jaw members, for example.

Further to the above, in various embodiments, at least one resilient member can be biased towards the piece of buttress material such that the resilient members can apply a retaining force to the piece of buttress material and releasably retain the piece of buttress material to one of the first and second jaw members. In at least one embodiment, the piece of buttress material can include tissue-contacting portion 159 or 159' and two side portions 160 or 160' extending in a substantially perpendicular and/or transverse direction with respect to tissue-contacting portion 159 or 159'. In at least one such embodiment, tissue contacting portion 159 can be configured to be positioned adjacent to or in contact with deck 128 and, in addition, side portions 160 can be configured to abut side walls 121 of first jaw member 120. Similarly, tissue contacting portion 159' can be positioned adjacent to or in contact with surface 132 and, in addition, side portions 160' can be configured to abut side walls 125 of second jaw member 124. In various embodiments, each second end 154 of each resilient member 150 can be configured to engage the side portions 160 of piece of buttress material 136 and apply a retaining force thereto. In at least one embodiment, resilient members 150, for example, can be configured to release buttress material 136 after staples have been deployed through the buttress material and/or when the buttress material is disengaged from the end-effector. In at least one embodiment, the resilient members can be comprised of an elastic material such as metal or plastic, for example.

In various embodiments, referring to FIGS. 15-18, a retention member can be configured to be moved within an end-effector between a first position and a second position to releasably retain a piece of buttress material to the end-effector. In at least one embodiment, end-effector assembly 214 can include a first jaw including staple cartridge 222 and a second jaw including anvil 226 wherein retention member 262 can be moved relative to staple cartridge 222 and anvil 226. In various embodiments, retention member 262 can be moved between a first, or extended, position near distal end 264 to a second, or retracted, position near proximal end 263. In its extend position, retention member 262 can hold buttress material 236 in position as end effector 214 is inserted into a surgical site. Thereafter, end effector 214 can be closed onto tissue, for example, and staples can be deployed through the buttress material into the tissue. In various embodiments, retention member 262 can be moved into its retracted position such that retention member 262 can be operably disengaged from buttress material 236. In at least one embodiment, retention member 262 can be retracted prior to the staples being deployed. In any event, as a result of the above, end effector 214 can be opened and withdrawn from the surgical site leaving behind the stapled buttress material and tissue.

In various embodiments, a retention member can have proximal ends which can be operably engaged with a lever or other actuating mechanism in a handle portion of a surgical stapling instrument such that a surgeon can remotely retract the retention member as outlined above. In at least one embodiment, retention member 262 can have distal ends which can be engaged with, or otherwise releasably retained by, retention bar 264 such that a force may need to be applied to retention members 262 to dislodge them from retention bar 264. Thereafter, retention members 262 can be retracted proximally a distance L in order to move them into their second position. In at least one embodiment, retention members 262 can be retracted through channels or apertures 266 in buttress material 236, for example, until they are sufficiently removed from the buttress material. In at least one such embodiment, apertures 266 can encircle and guide retention members 262 as they are retracted. In various embodiments, the retention members can be comprised of flexible wires. In at least one embodiment, an end effector can include two or more pieces of buttress material retained to an end effector by retractable retention members. In at least one such embodiment, referring to FIGS. 17 and 18, end effector 214 can include retention members 262' for holding buttress material 236' in position.

Figure 19:
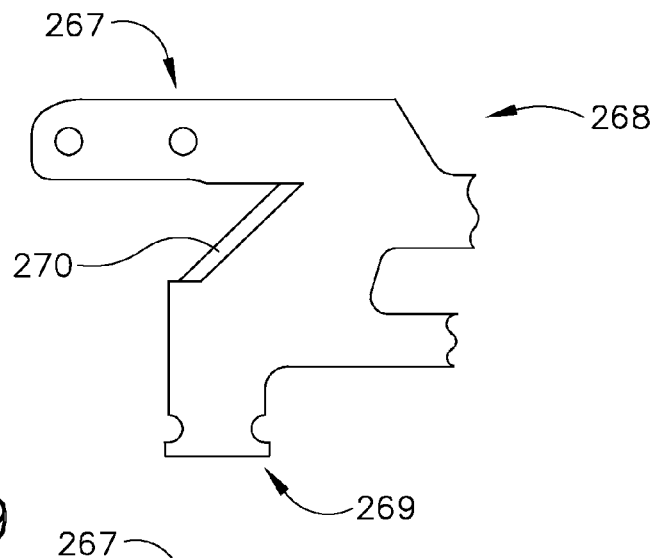
FIGS. 19-21 are side views of various cutting members configured to be used with an end-effector assembly in accordance with non-limiting embodiments of the present invention.
Figure 20:
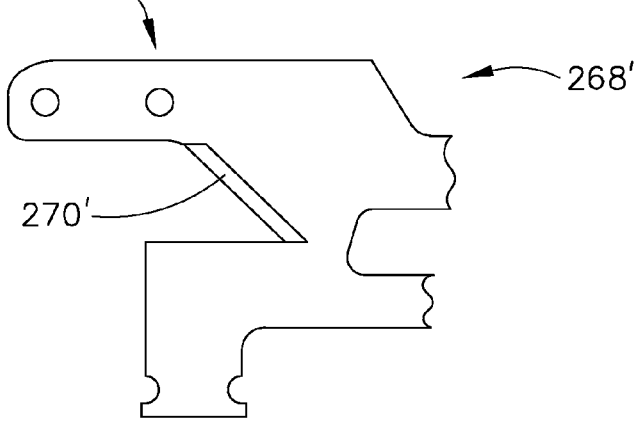
Figure 21:
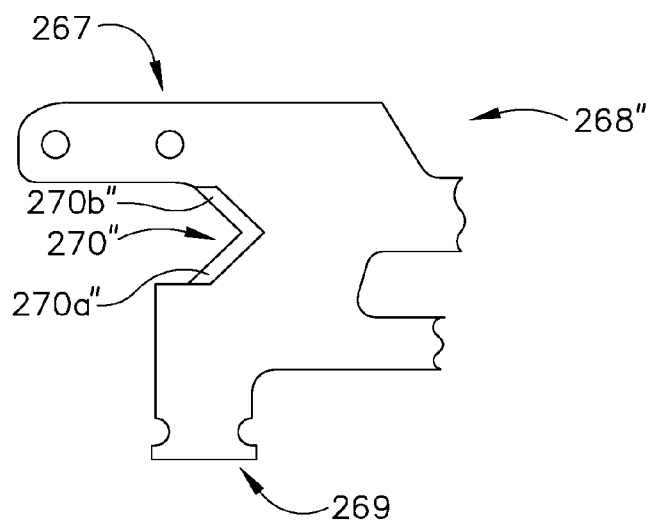

In various embodiments, an end-effector assembly can include a cutting member configured to incise one or more pieces of buttress material. In at least one embodiment, a cutting member can be motivated relative to an end-effector by a surgical instrument firing drive and can be guided by a cutting member slot within an anvil and/or staple cartridge of an end-effector. In at least one embodiment, referring to FIG. 19, top portion 267 of cutting member 268 can be configured to slide within a slot in the anvil and, additionally, bottom portion 269 of the cutting member can be configured to slide within a slot within the staple cartridge. In various embodiments, cutting member 268 can include blade 270 having a positive slope, i.e., a cutting edge having a bottom end which is positioned distally with respect to a top end. In at least one embodiment, such a configuration can be configured to incise the buttress material without substantially pushing the buttress material distally and disrupting the alignment of the buttress material within the end-effector. In at least one alternative embodiment, referring to FIG. 20, blade 270' of cutting member 268' can include a negative slope, i.e., a cutting edge having a bottom end which is positioned proximally with respect to a top end. In further alternative embodiments, referring to FIG. 21, blade 270" of cutting member 268" can include first portion 270a" having a positive slope and second portion 270b" having a negative slope.

Figure 22:
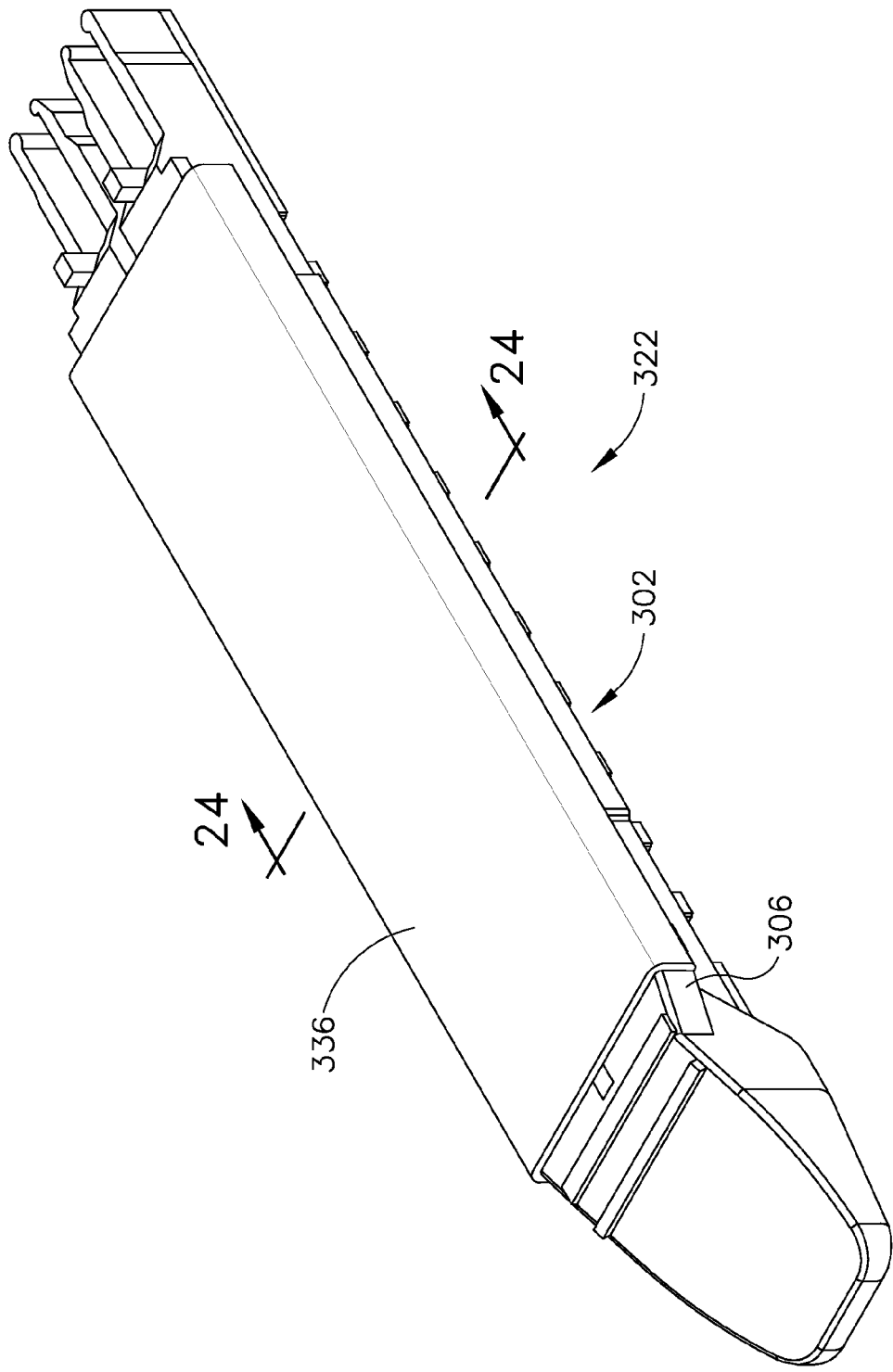
FIG. 22 is a perspective view of a staple cartridge having a piece of buttress material releasably retained thereto in accordance with one non-limiting embodiment of the present invention.
Figure 23:
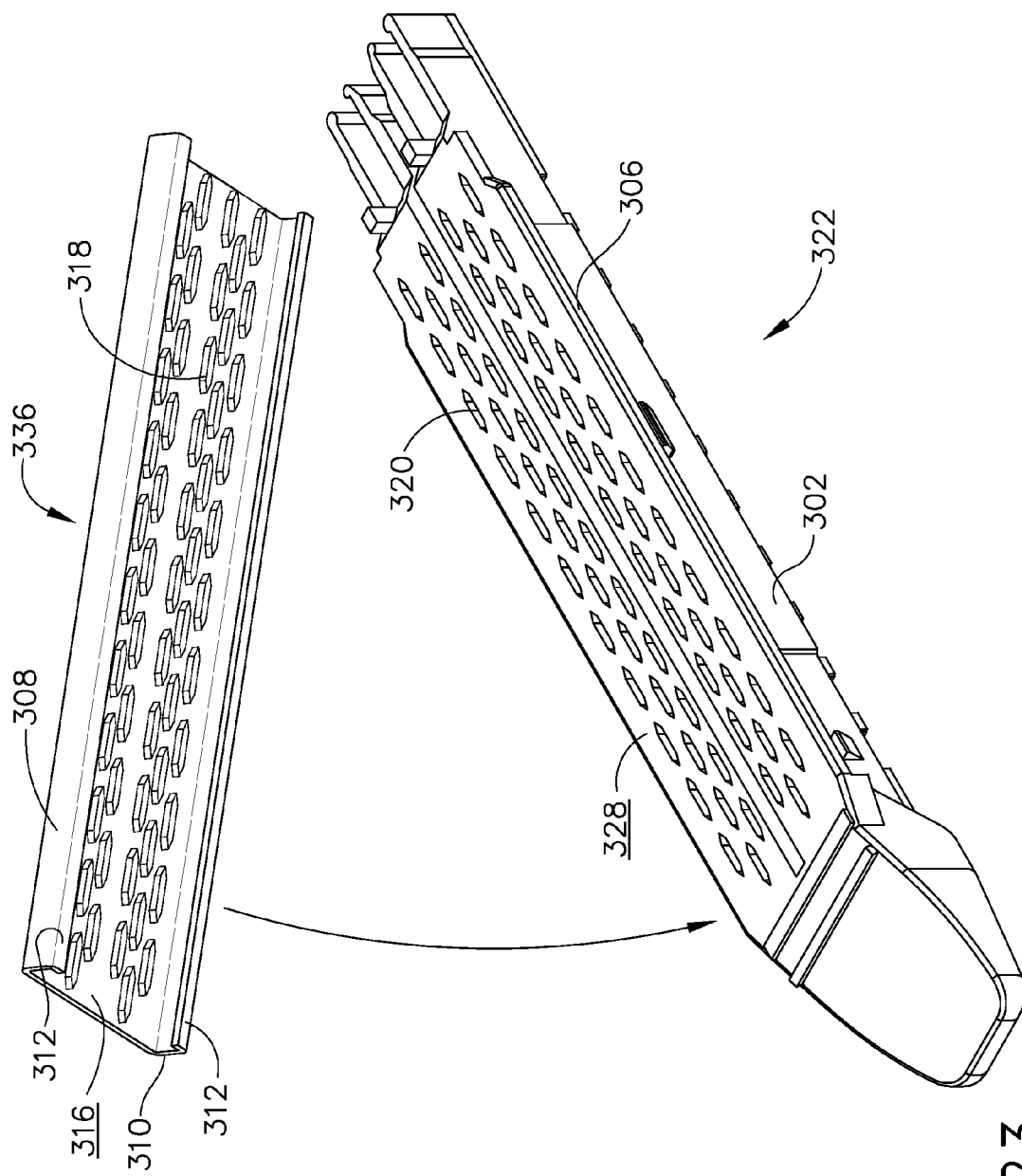
FIG. 23 is an exploded perspective view of the staple cartridge and the piece of buttress material of FIG. 22, wherein the piece of buttress material includes a plurality of members extending therefrom.
Figure 24:
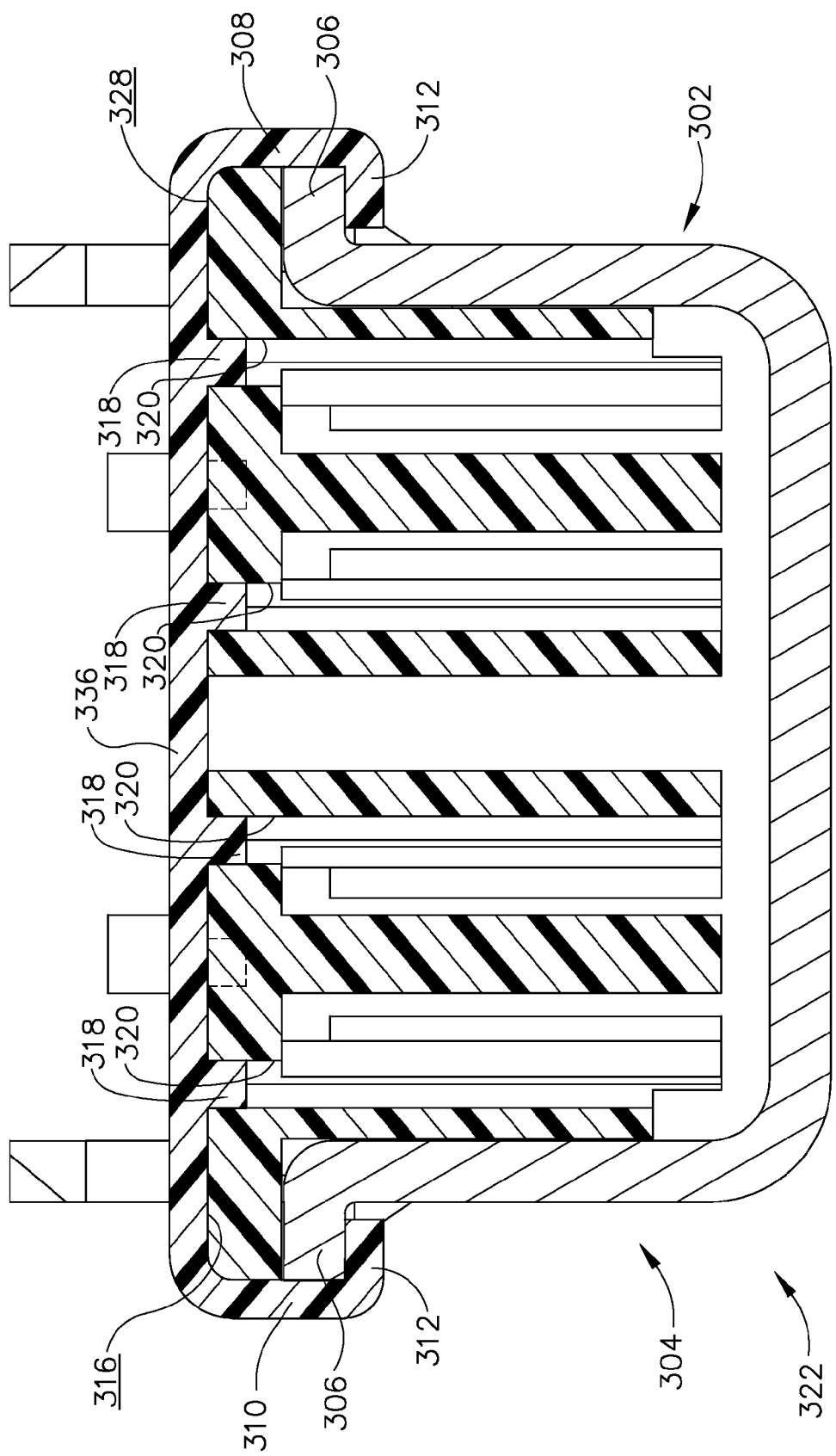
FIG. 24 is a cross-sectional view taken along line 24-24 in FIG. 22 illustrating the members of FIG. 23 engaged with staple cavities in accordance with one non-limiting embodiment of the present invention.

As outlined above, an end-effector assembly can include a staple cartridge, an anvil, and at least one piece of buttress material positioned intermediate the staple cartridge and the anvil. In at least one embodiment, referring to FIGS. 22-24, a piece of buttress material, such as buttress material 336, can be configured to be snap-fit to at least one of staple cartridge 322 and/or an anvil (not illustrated) to releasably retain the piece of buttress material within the end effector. Referring to FIGS. 23 and 24, staple cartridge 322 can include first side wall 302 and second side wall 304, wherein at least one of the first and second side walls can include a lip 306 extending outwardly therefrom. In various embodiments, buttress material 336 can include first edge, or side, 308, second edge, or side, 310, and at least one lip 312 extending at least partially along the length of edges 308 and 310. In at least one embodiment, referring to FIG. 24, lips 312 can be configured to engage lips 306 in a snap-fit fashion in order to releasably retain buttress material 336 to staple cartridge 322.

Further to the above, referring to FIG. 24, buttress material 336 can include surface 316 which can be configured to be positioned adjacent to or against deck 328 of staple cartridge 322. In at least one embodiment, side edges 308 and 310 can comprise sidewalls which can extend in a perpendicular or transverse direction relative to surface 316. In such embodiments, lips 312 can extend from these sidewalls such that lips 312 can be interlocked behind lips 306 of staple cartridge 322. In various embodiments, lips 312 of buttress material 336 can be disengaged from lips 306 of staple cartridge 322 when the staples are deployed from staple cartridge 322. More particularly, when the staples are deployed, the staples can contact buttress material 336, apply an upward force to buttress material 336, and dislodge buttress material 336 from staple cartridge 322. Advantageously, as a result, buttress material 336 may be automatically disengaged from staple cartridge 322 when the staples are deployed therefrom and/or when the end-effector is opened as described above.

In various embodiments, referring to FIGS. 23 and 24, a piece of buttress material can include at least one member extending therefrom which can be configured to releasably retain the buttress material to one of a staple cartridge and/or an anvil. In at least one embodiment, member 318 can extend from buttress material 336 in a direction which is perpendicular or transverse to surface 316. In various embodiments, member 318 can be engaged with one of staple cavity 320, and/or an anvil pocket, in a friction-fit or press-fit manner to releasably retain the piece of buttress material to one of the staple cartridge and the anvil. Similar to the above, in various embodiments, staples deployed from staple cavities 320 can apply an upward force to buttress material 336 and disengage members 318 from staple cavities 320. In various embodiments, the staples can pierce projections 318 and/or buttress material 336 to secure the buttress material to the tissue as outlined above.

Figure 25:
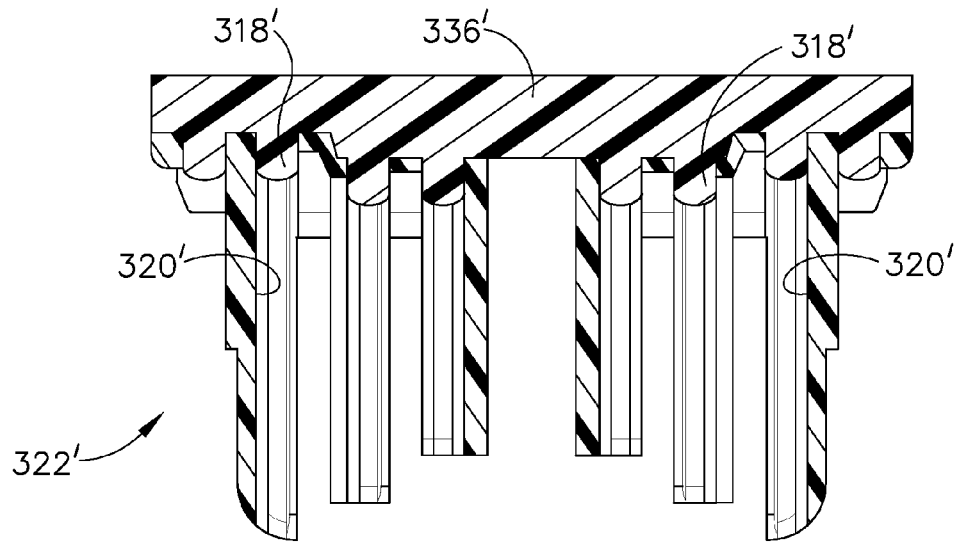
FIG. 25 is a cross-sectional view of a piece of buttress material including members engaged with staple cavities of a staple cartridge in accordance with one non-limiting embodiment of the present invention.
Figure 26:
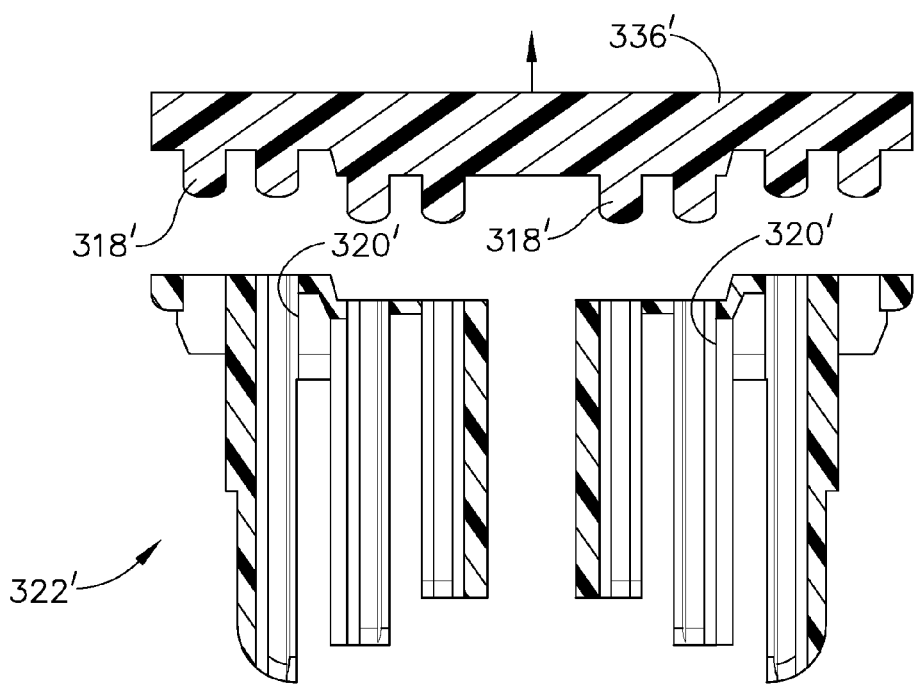
FIG. 26 is an exploded view of FIG. 25 illustrating the members separated from the staple cavities of the staple cartridge in accordance with one non-limiting embodiment of the present invention.

As illustrated in FIG. 23, a piece of buttress material can include more than one member, or projection, extending therefrom to retain a piece of buttress material to one of a staple cartridge and an anvil. In various embodiments, referring to FIGS. 25-26, more than one member 318' can extend from piece of buttress material 336', for example. In at least one embodiment, members 318' can be can press-fit into staple cavities 320' of staple cartridge 322', and/or into anvil pockets of an anvil (not illustrated), such that the members can frictionally retain the piece of buttress material to the staple cartridge and/or the anvil as outlined above. As described in greater detail below, a staple cartridge and/or anvil can include slots or apertures therein in addition to the staple cavities of the staple cartridge and the anvil pockets of the anvil for receiving projections, or retaining members, extending from a piece of buttress material.

Figure 33:
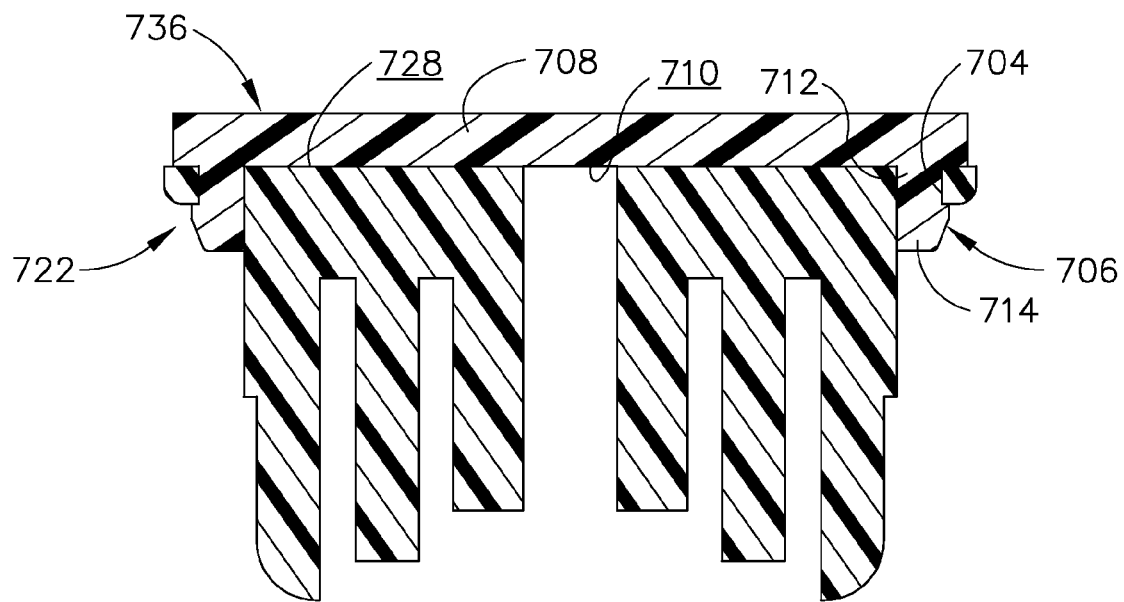
FIG. 33 is a cross-section view of a staple cartridge including a piece of buttress material releasably retained thereto in accordance with one non-limiting embodiment of the present invention.

In various embodiments, referring to FIG. 33, at least one of an anvil and a staple cartridge of an end-effector assembly can include one or more slots and/or grooves configured to releasably retain a piece of buttress material to the end-effector assembly. In at least one embodiment, staple cartridge 722 can include at least one aperture 704 defined therein which can be configured to receive projection 706 extending from buttress material 736. In at least one such embodiment, projection 706 can be received within aperture 704 in a press-fit and/or friction-fit fashion to releasably retain buttress material 736 thereto. In at least one embodiment, referring to FIG. 33, buttress material 736 can include body 708 having surface 710, wherein surface 710 can be configured to be positioned adjacent to and/or abut deck 728. In various embodiments, projection 706 can extend from body 708 in a direction which is perpendicular or transverse to a plane defined by surface 710, for example.

In various embodiments, projection 706, for example, can include first portion, or leg, 712 and second portion, or foot, 714, wherein first portion 712 can be configured to extend through aperture 704 and wherein second portion 714 can have a size and shape which can be slightly larger than aperture 704, for example. In at least one such embodiment, projection 706 can be inserted into and pushed through aperture 704 until second portion 714 at least partially extends therethrough. In various embodiments, projection 706 can deflect inwardly as it is inserted into aperture 704 and then snap outwardly after it has been inserted therethrough. In addition to or in lieu of the above, second portion 714 can be compressed as it is inserted into aperture 704 and then expand once it has been inserted therethrough. In any event, second portion 714 can engage a backside surface of deck 728 near aperture 704 in order to releasably retain buttress material 736 to staple cartridge 702 in a snap-fit fashion. In at least one embodiment, projection 706 can be releasably retained within aperture 704 until a force is applied thereto by staples deployed from the staple cartridge and/or when the end-effector is opened as described above.

Figure 27:
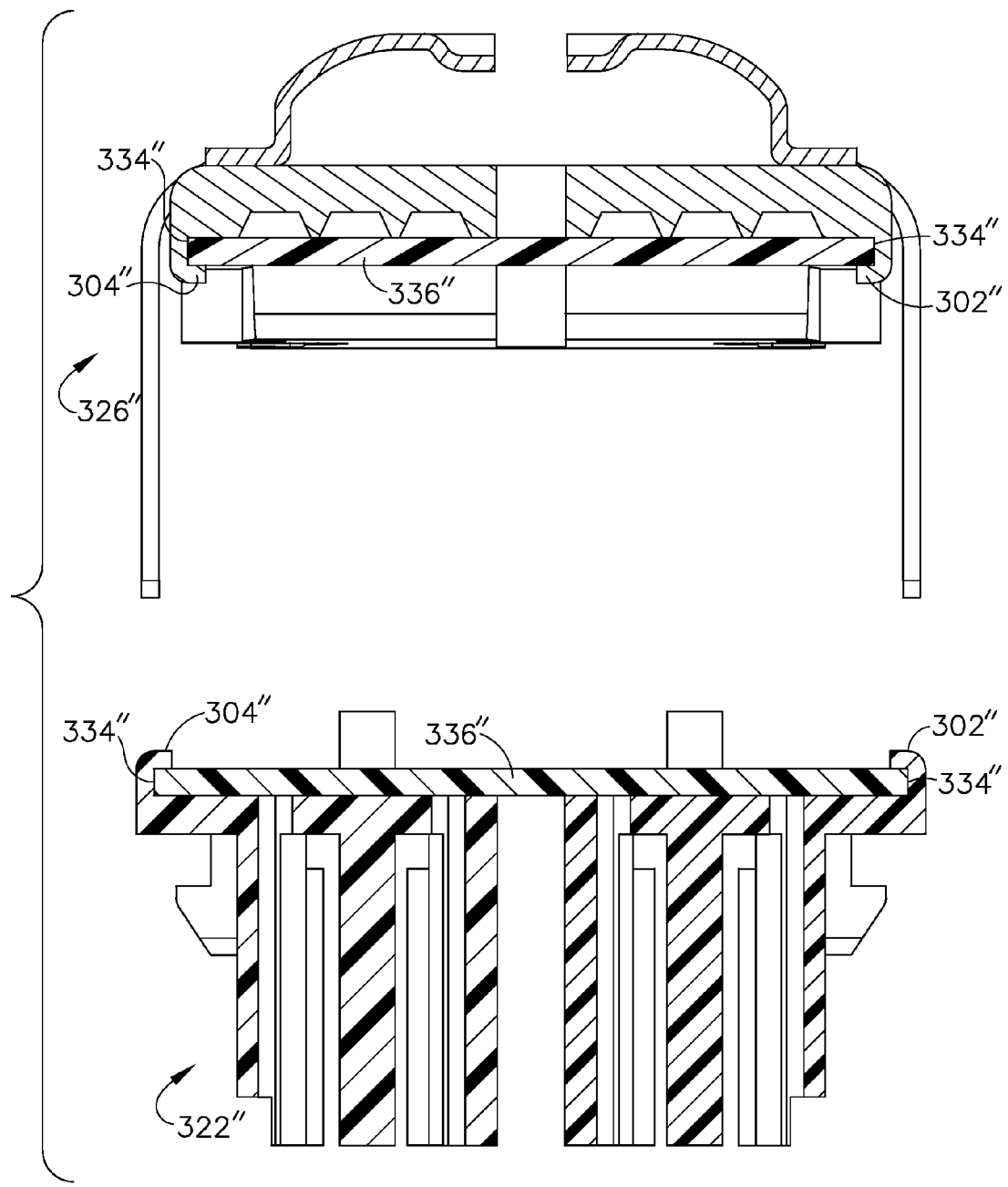
FIG. 27 is an exploded cross-sectional view of an end-effector assembly including retaining members extending from an anvil and a staple cartridge of the end-effector which are configured to releasably retain a piece of buttress material in accordance with one non-limiting embodiment of the present invention.
Figure 28:
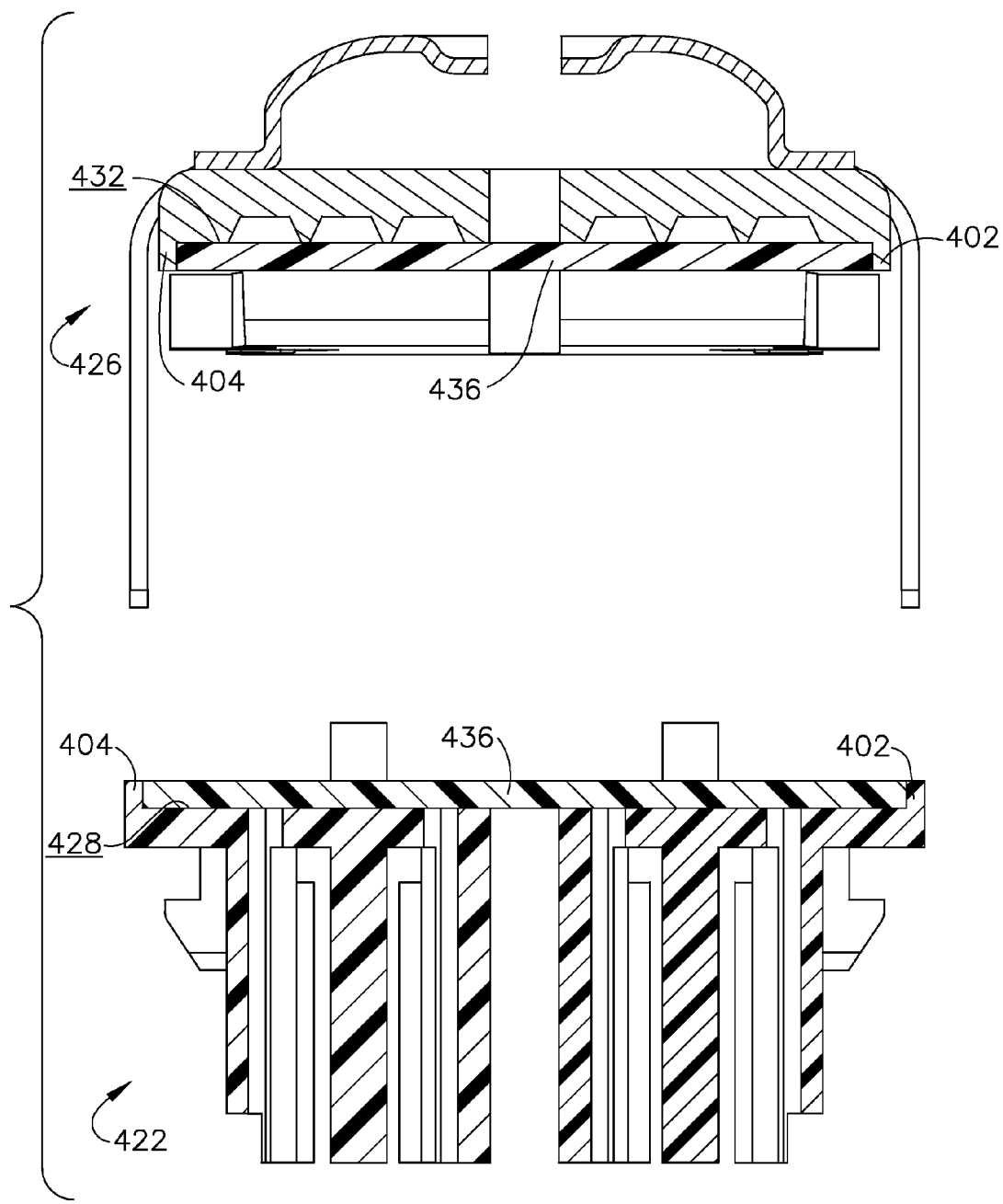
FIG. 28 is an exploded cross-sectional view of an end-effector assembly including retaining members extending from an anvil and a staple cartridge of the end-effector which are configured to releasably retain a piece of buttress material in accordance with one non-limiting embodiment of the present invention.

In various embodiments, referring to FIG. 27, staple cartridge 322" and/or anvil 326", for example, can include notches 334" which can be configured to receive buttress material 336". In at least one embodiment, notches 334" can be configured to releasably retain buttress material 336" to staple cartridge 322". In at least one such embodiment, buttress material 336" can be press-fit between retaining members 302" and 304" such that a force must be applied thereto to overcome friction between buttress material 336" and retaining members 302" and 304". In various embodiments, retaining members 302" and 304" can include lips or overhangs which can prevent, or at least inhibit, buttress material 336" from lifting upwardly. In various embodiments, referring to FIG. 28, an end-effector assembly can include staple cartridge 422 and anvil 426, wherein at least one of the staple cartridge and the anvil can include first retaining member 402 and/or second retaining member 404 extending therefrom. In at least one embodiment, the first and second retaining members 402 and 404 can extend substantially perpendicular to and/or transverse with respect to one of deck 428 and/or face 432 to retain a piece of buttress material 436 to the end effector. In various embodiments, first and second retaining members 402 and 404 can be configured to releasably retain buttress material 436 therebetween in a friction-fit fashion. In at least one embodiment, the coefficient of friction between the side walls and the retaining members can be sufficient such that the buttress material may not be dislodged as the end effector is inserted into and manipulated within a surgical site. After the staples have been deployed into the soft tissue, the end-effector can be re-opened and, in various embodiments, the friction force between buttress material 436 and retention members 402 and 404 can be overcome.

Figure 32:
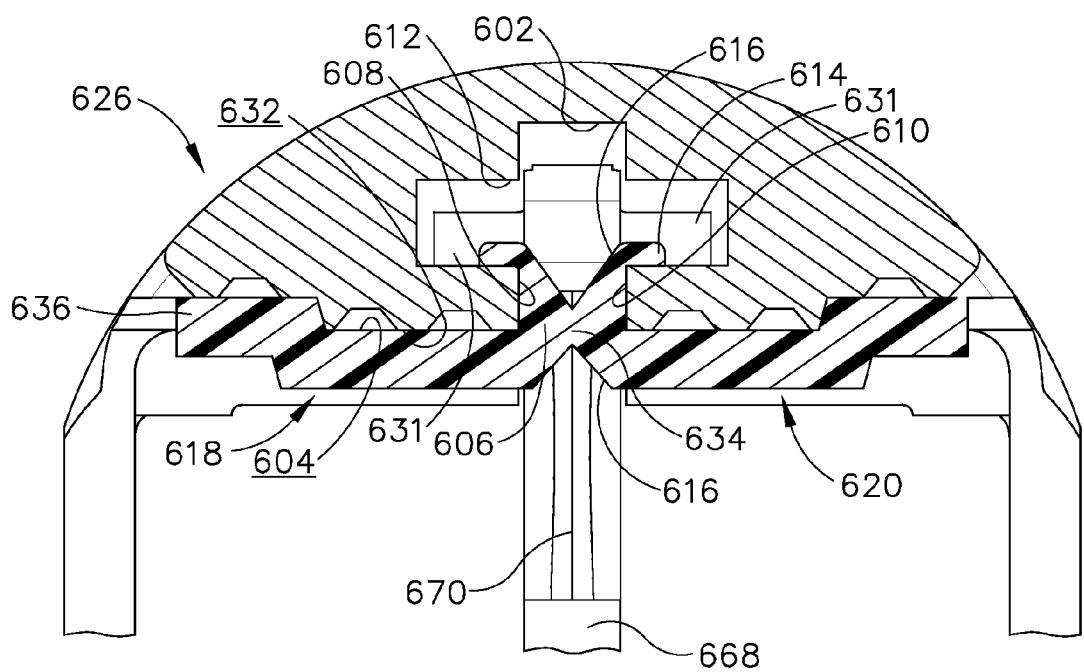
FIG. 32 is a cross-sectional view of an anvil having a piece of buttress material engaged with a cutting member slot in accordance with one non-limiting embodiment of the present invention.

In various embodiments, referring to FIG. 32, an end-effector of a surgical stapling instrument can include an anvil and a staple cartridge (not illustrated), wherein, as outlined above, the anvil can be operatively engaged with the staple cartridge such that the end-effector can be configured to clamp tissue therebetween. In at least one embodiment, anvil 626 can include face 632 and, in addition, slot 602 which can be configured to slidably receive a cutting member, such as cutting member 668, for example, therein. In various embodiments, although not illustrated, the staple cartridge can also include a slot configured to slidably receive cutting member 668 therein. In any event, cutting member 668 can include a blade, such as blade 670, for example, where blade 670 can be configured to incise soft tissue and/or buttress material 636 positioned within the end effector.

In at least one embodiment, referring again to FIG. 32, buttress material 636 can include a body portion having a surface, such as surface 604, for example, wherein the surface can be configured to be positioned adjacent to anvil face 632, for example. In various embodiments, buttress material 636 can further comprise projection 606 extending from the body portion in a perpendicular and/or transverse direction with respect to surface 604. In at least one embodiment, projection 606 can be configured to be inserted into and engaged with cutting member slot 602 to releasably retain buttress material 636 to anvil 626. Although not illustrated, a piece of buttress material can include similar features which can retain the buttress material to a staple cartridge.

In various embodiments, cutting member slot 602 can include first side wall 608 and second side wall 610 wherein projection 606 can be configured to be frictionally engaged with, and/or press-fit between, the first and second side walls and releasably retain projection 606 within slot 602. In at least one embodiment, slot 602 can include transverse portion 612 which can be configured to receive cam members 631 extending from cutting member 668, wherein cam members 631 can be configured to hold anvil 626 in a closed position. In at least one embodiment, projection 606 can include at least one tab 614 extending therefrom which can be configured to at least partially extend into transverse portion 612 and assist in retaining projection 606 within slot 602. In various embodiments, a projection can include resilient features which can apply a biasing force to the side walls of slot 602 when they are compressibly received within slot 602.

In various embodiments, further to the above, cutting member 668 can be configured to incise projection 606 as it is advanced within anvil 626 and separate first portion 618 from second portion 620. In at least one embodiment, grooves 616 can reduce the cross-sectional thickness of buttress material 636 in order to reduce the force needed to transect the buttress material. In various embodiments, one or more of grooves 616 can be sized and dimensioned such that at least a portion of projection 606 is thinner than first portion 618 and/or second portion 620. As described above, at least one of grooves 616 can be V-shaped, for example, such that cutting edge 670 can contact projection 606 at or near the point of the V-shaped profile. In various embodiments, although not illustrated, projection 606, for example, can include at least one perforation defined therein which can lower the force needed to incise the projection.

In various embodiments, either in addition to or in lieu of the buttress material attachment devices discussed above, a piece of buttress material can be attached to an end-effector of a surgical instrument using an adhesive. In at least one embodiment, referring to FIGS. 29 and 30, end-effector assembly 514 can include anvil 526 having face 532 and, in addition, staple cartridge channel 522 having deck surface 528. In at least one embodiment, a piece of buttress material, such as buttress material 536, for example, can be positioned adjacent to one of face 532 and deck surface 528, wherein buttress material 536 can include body portion 502 and at least one handle portion 506. In at least one such embodiment, handle portion 506 can extend from body 502 such that a surgeon can use handle portion 506 to position and align buttress material 536 within the end-effector assembly. In at least one embodiment, handle portion 506 can extend in a direction which is parallel to, and/or transverse to, a plane of surface 504.

Figure 29:
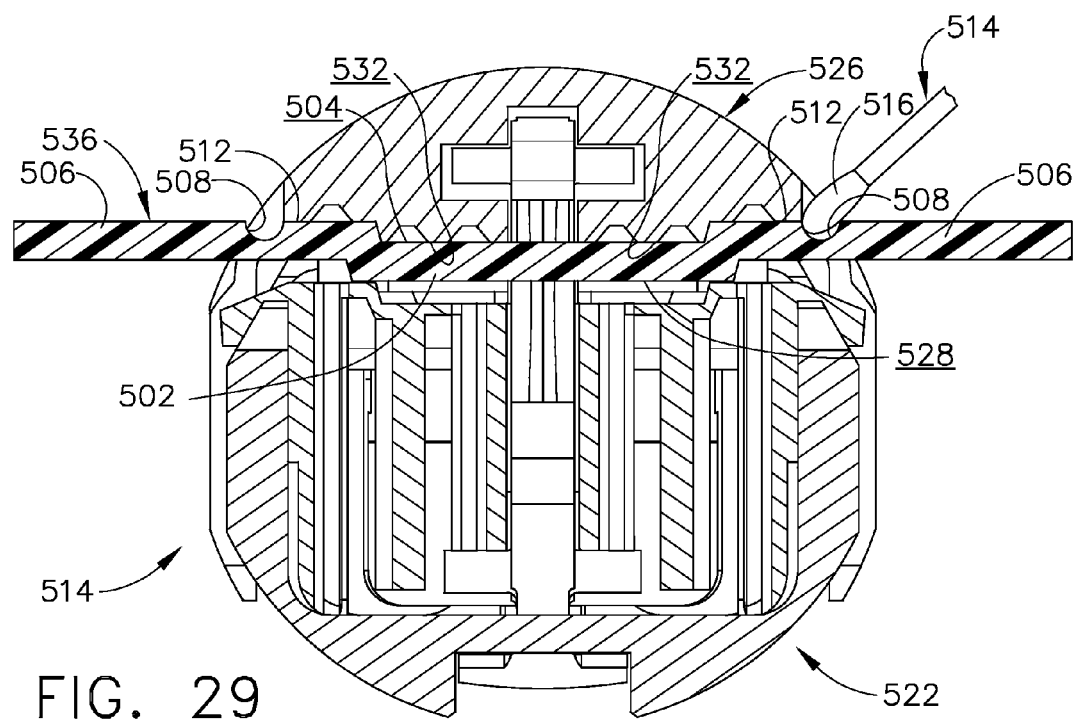
FIG. 29 is a cross-sectional view of an end-effector illustrating a piece of buttress material positioned within the end-effector, wherein the piece of buttress material includes recesses in accordance with one non-limiting embodiment of the present invention.
Figure 30:
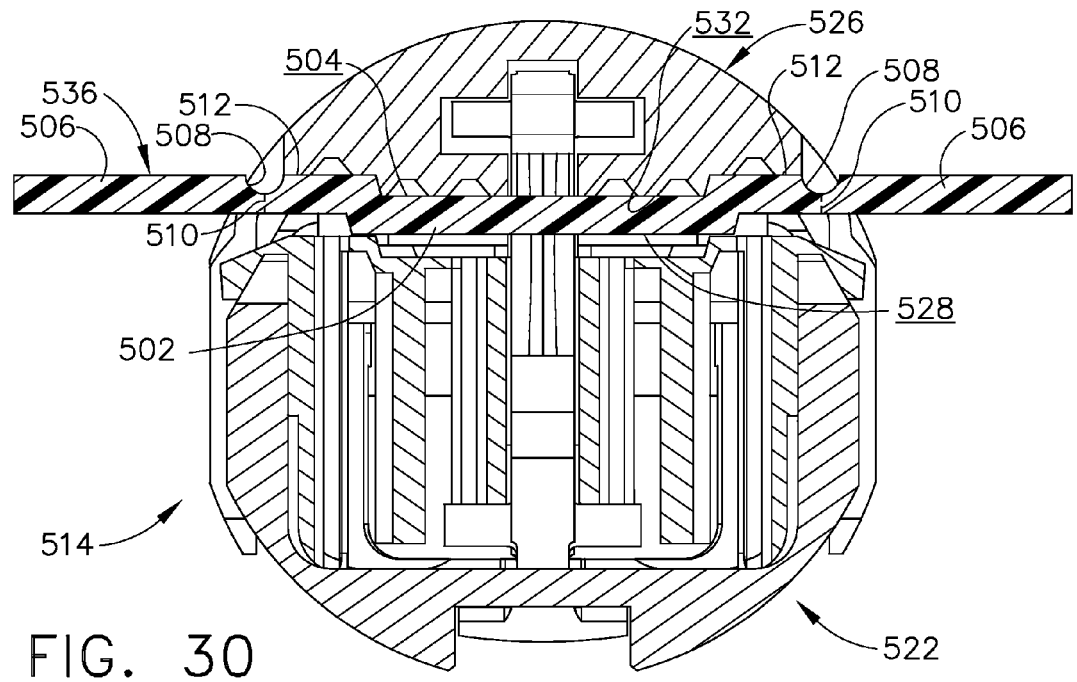
FIG. 30 is a cross-sectional view of an end-effector illustrating a piece of buttress material positioned within the end-effector, wherein the piece of buttress material includes perforations and recesses in accordance with one non-limiting embodiment of the present invention.

In various embodiments, referring to FIGS. 29 and 30, a piece of buttress material can include an un-activated or inert adhesive, such as adhesive 512, for example, on the surface of the buttress material which can be applied to the surface prior to the surface being positioned against one of the staple cartridge deck and the anvil face. In at least one embodiment, adhesive 512 can be configured to releasably bond surface 504, for example, to face 532 and/or deck 528 when the adhesive is activated by a reactant. Similar to the above, such an activated adhesive can be used to releasably retain surface 504 in contact with face 532 and/or deck 528. In various embodiments, the activated adhesive can be configured to release the buttress material from the deck and/or face in response to a force applied thereto such as when the staples are deployed from the staple cartridge and/or when the end-effector is opened, for example. In various embodiments, the un-activated adhesive can be applied to the buttress material along the outer perimeter of body portion 502 such that a reactant, for example, can be easily applied to the un-activated adhesive.

In various embodiments, the un-activated adhesive on the buttress material can comprise one component of a binary adhesive and the reactant can comprise the other component of the binary adhesive such that, when the two components are combined, the adhesive is activated. Stated another way, the un-activated adhesive can include a material which is inert until it is introduced to a reactant as described below. In at least one embodiment, the un-activated adhesive and the reactant can comprise a surgically suitable epoxy, for example. In various embodiments, the un-activated adhesive can include a hydro-stable material, for example, such that the adhesive can be substantially non-soluble and/or substantially non-reactive when introduced to water. In at least one embodiment, the adhesive can include a material such as a hot melt adhesive, silicone, urethane, cyanoacrylate, hydrogel, and/or isocyanolate, for example, or any suitable monomer and/or polymer. In various embodiments, suitable adhesives and attachment devices can include those disclosed in U.S. Pat. No. 5,263,629, entitled METHOD AND APPARATUS FOR ACHIEVING HEMOSTASIS ALONG A STAPLE LINE, which issued on Nov. 23, 1993; U.S. Pat. No. 6,656,193, entitled DEVICE FOR ATTACHMENT OF BUTTRESS MATERIAL TO A SURGICAL FASTENING DEVICE, which issued on Dec. 2, 2003; U.S. Pat. No. 6,592,597, entitled ADHESIVE FOR ATTACHING BUTTRESS MATERIAL TO A SURGICAL FASTENING DEVICE, which issued on Jul. 15, 2003; U.S. Pat. No. 6,273,897, entitled SURGICAL BETTRESS AND SURGICAL STAPLING APPARATUS, which issued on Aug. 14, 2001; and U.S. patent application Ser. No. 10/674,303, entitled APPARATUS AND METHOD FOR ATTACHING A SURGICAL BUTTRESS TO A STAPLING APPARATUS, which was filed on Sep. 30, 2003, the entire disclosures of which are hereby incorporated by reference herein. In various embodiments, the reactant can include a material comprising at least one aerobic initiator, anaerobic initiator, quaternary ammonium salt or compound, and/or any other suitable radical mechanism initiator such as anionic initiators, for example, including the materials disclosed in U.S. patent application Ser. No. 11/479,424, entitled ABSORBABLE CYANOACRYLATE COMPOSITIONS, which was filed on Jun. 30, 2006, the entire disclosure of which is hereby incorporated by reference herein. In various embodiments, adhesives and/or reactants which are commercially available from Closure Medical Corporation, for example, can be used. In at least one embodiment, an adhesive can be configured to be activated by ultra-violet light or any suitable photochemical process. Several such adhesives are commercially available from Henkel Loctite Corporation, for example.

Further to the above, in various embodiments, the use of the un-activated or inert adhesive on the piece of buttress material can enable a surgeon to position and re-position the piece of buttress material on the anvil face and/or the staple cartridge deck without the adhesive immediately bonding thereto. In at least one embodiment, the un-activated adhesive may not bond to the face and/or deck until the reactant is applied to the un-activated adhesive. This feature provides a significant advantage in that the surgeon does not have to properly position the piece of buttress material on a first attempt, but instead can position and re-position the piece of buttress material on the deck and/or face to ensure a proper fit and alignment with the face and/or the deck. In various embodiments, at least one retention or alignment member, such as retention member 318 (FIG. 23), for example, can be used in conjunction with the adhesive/reactant to retain the piece of buttress material to the face and/or deck of the end-effector prior to application of the reactant, for example.

In various embodiments, a piece of buttress material can include at least one groove or channel which can be configured to receive the reactant. In at least one embodiment, referring to FIG. 29, buttress material 536 can include recesses 508 which can be located intermediate body portion 502 and handle portions 506. More particularly, a first recess 508 can be provided intermediate a first side of body 502 and a first handle portion 506 and, additionally, a second recess 508 can be provided intermediate a second side of body 502 and a second handle portion 506. In various embodiments, at least a portion of un-activated adhesive 512 on buttress material 536 can extend along recesses 508 such that an applicator, such as applicator 514, for example, can be inserted into recesses 508 to apply the reactant to adhesive 512 and activate the adhesive. In at least one embodiment, as a result, recesses 508 can facilitate the application of the reactant. In various embodiments, reactant applicator 514 can include absorbent tip 516 which can be configured to releasably store and apply a quantity of reactant.

Figure 31:
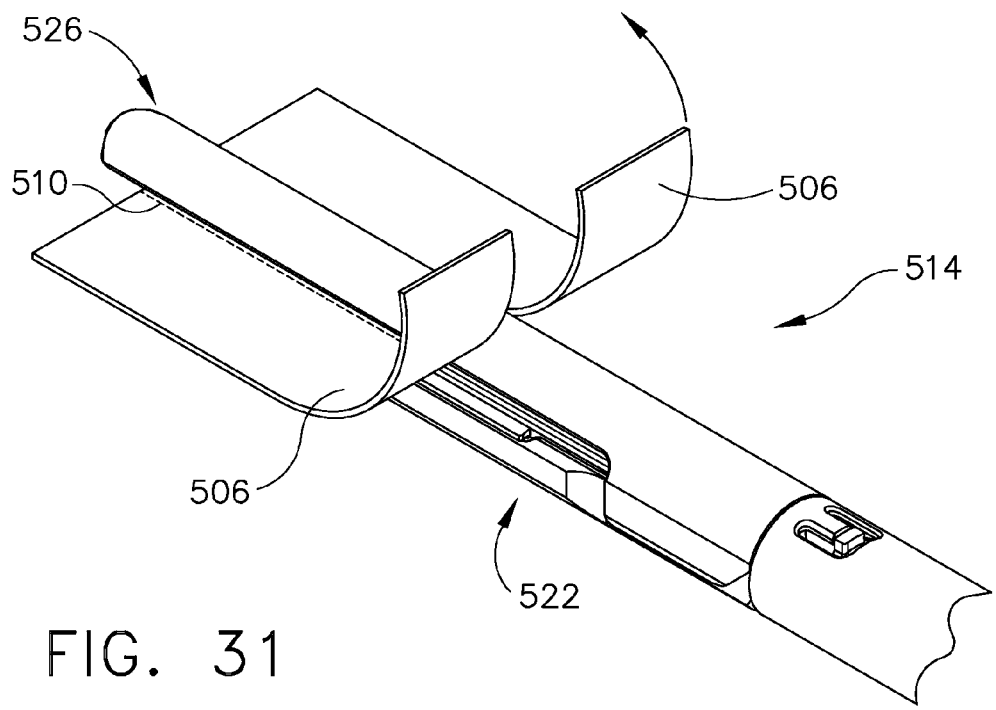
FIG. 31 is a perspective view of portions of the piece of buttress material of FIG. 30 being removed from an intermediate portion.

In various embodiments, referring to FIGS. 30 and 31, at least one perforation can be defined within a piece of buttress material 536 to allow at least one of handle portions 506 to be detached from body portion 502, for example. In at least one embodiment, perforations 510 can be located intermediate body portion 502 and handle portions 506 such that, when a sufficient force is applied to a handle portion 506, the piece of buttress material can tear along a line, or path, defined by perforations 510. In various embodiments, perforations 510 can be positioned adjacent to and/or within recesses 508 such that handle portion 506 can easily be separated from body 502 owing to the reduced material thickness of the buttress material within and/or adjacent to recesses 508. In at least one embodiment, as a result of the above, a piece of buttress material can be positioned within an end-effector, a reactant can be applied to un-activated adhesive on the buttress material, and at least one of the handle portions can be removed from a central body portion of the buttress material.

In various embodiments, a piece of buttress material, an un-activated adhesive, and a reactant can be included in a surgical accessory kit, for example. In at least one embodiment, the un-activated adhesive can be pre-applied to the buttress material. In other embodiments, a surgeon can use the kit to apply the un-activated adhesive to a surface of the buttress material and allow the adhesive to "set", i.e., cure or dry such that it can be positioned on a surface without substantially adhering to the surface. In at least one embodiment, the piece of buttress material can then be positioned against one of the staple cartridge or anvil of an end-effector. In at least one such embodiment, as outlined above, the buttress material can include at least one handle extending therefrom in which the surgeon can grasp to manipulate the buttress material relative to the end-effector. Thereafter, the anvil of the end-effector can be closed onto the buttress material to hold it in position until the reactant is applied thereto. At such point, referring to FIG. 31, the handle portion can be removed while the anvil is closed. Alternatively, the surgeon can wait for the activated adhesive to at least partially cure before removing the handle. In either event, the end-effector can then inserted into a surgical site and the buttress material can be attached to tissue with staples as described above. In other various embodiments, the handle portion(s) can be torn away from the body portion of the buttress material after staples are engaged with the tissue.

In various embodiments, a package assembly for at least one piece of buttress material can include means for activating an un-activated adhesive on the buttress material. In at least one embodiment, a package assembly can include a quantity of reactant stored therein wherein the reactant can be released such that it can come into contact with the un-activated adhesive and activate the adhesive. In other various embodiments, a package assembly can include an initiator which can be configured to cause a reaction between an un-activated adhesive and another chemical within the package assembly. In further various embodiments, an un-activated adhesive can be configured to activate when sufficient pressure is applied thereto. Such pressure can be generated when the anvil of the end effector is closed onto the buttress material and clamped against the staple cartridge. Such materials can comprise one or more pressure-sensitive adhesives such as silicone adhesives and acrylic adhesives, for example. In various embodiments, a package can include a piece of buttress material having a biocompatible hot-melt adhesive positioned thereon, wherein the adhesive can be configured to melt when heat, generated by an exothermic chemical reaction, is applied thereto. In at least one embodiment, an initiator can be mixed with a chemical to create the exothermic reaction and thereby generate heat in the localized region of the adhesive, for example. In various embodiments, the initiator can be separated from the chemical by a removable sheet or other suitable separation device such that, when the sheet is removed, the initiator and the chemical can be exposed to each other. In at least one such embodiment, the initiator can include an oxidizer, or any suitable chemical compound that readily transfers oxygen atoms, for example, and the chemical can include can include iron or an iron compound, for example, which can be oxidized by the oxidizer to create an exothermic reaction.

In various embodiments, a package can include a piece of buttress material having a biocompatible hot-melt adhesive thereon, wherein the adhesive can be configured to be melted when heat generated by an electrical power source, such as a battery, for example, is applied thereto. In at least one embodiment, the package can include the electrical power source. In further various embodiments, the energy source can be provided on a portion of an end-effector, a piece of buttress material, a sleeve for an end-effector, and/or a buttress material applicator, for example. In various embodiments, the package assembly can include first and second contacts, and/or any other suitable conductors and resistors, which can be configured to operably complete an electrical circuit with the battery. In at least one embodiment, the electrical power source can be activated by a switch on the package, for example, and the electrical energy can be applied to the contacts.

In various embodiments, the anvil of an end-effector assembly can include a detachable portion or sleeve which can be configured to be slid over a second portion of the anvil and attached to the end-effector assembly. In at least one embodiment, as described in greater detail below, a piece of buttress material can be attached to the sleeve before the sleeve is assembled to the end-effector assembly. In at least one embodiment, referring to FIG. 34, sleeve 802 can be configured to be slid over anvil portion 826 such that sleeve 802 is held in place by at least one of a snap-fit and press-fit configuration. In at least one such embodiment, sleeve 802 can be configured to at least partially surround an outer perimeter 804 of anvil portion 826 wherein sleeve 802 can be configured to engage outer perimeter 804. In various embodiments, sleeve 802 can include anvil pockets 806 defined in working surface 808 wherein pockets 806 can be configured to deform staples deployed from a staple cartridge as described above. In various embodiments, sleeve 802 can be cast or machined from a piece of metal into any suitable configuration and can be comprised of any suitable material such as aluminum, for example.

Figure 34:
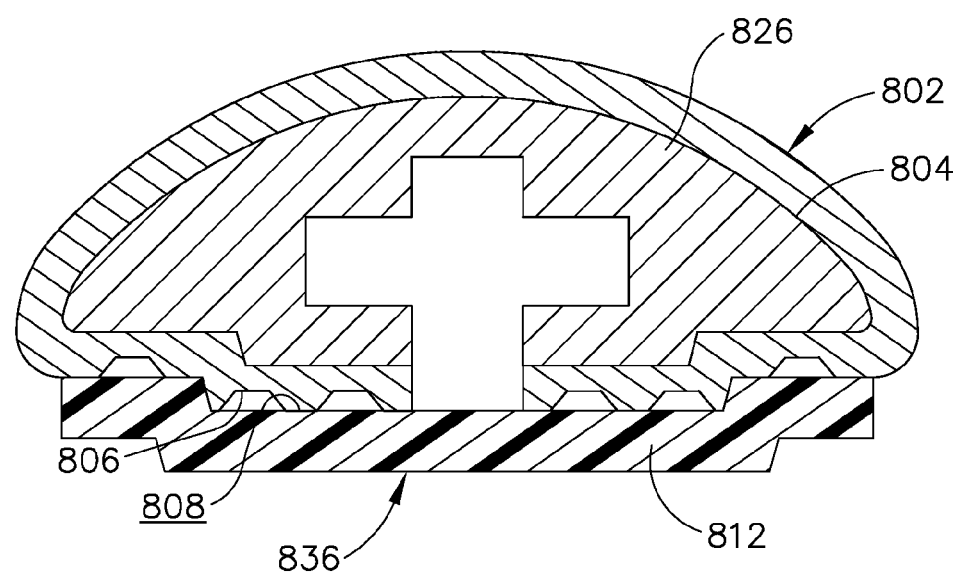
FIG. 34 is a cross-sectional view of a piece of buttress material releasably positioned on an anvil in accordance with one non-limiting embodiment of the present invention.
Figure 35:
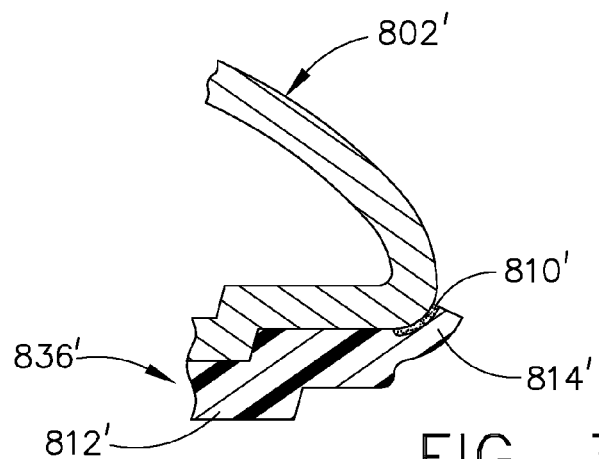
FIG. 35 is a detail view of a piece of buttress material releasably retained to an anvil in accordance with one non-limiting embodiment of the present invention.
Figure 36:
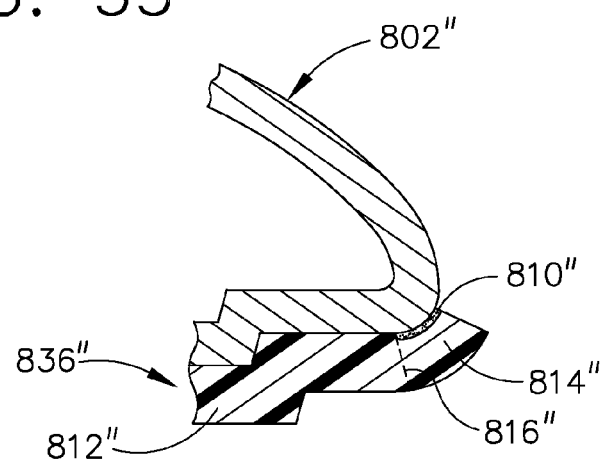
FIG. 36 is a detail view of a piece of buttress material releasably retained to an anvil in accordance with one non-limiting embodiment of the present invention.
Figure 37:
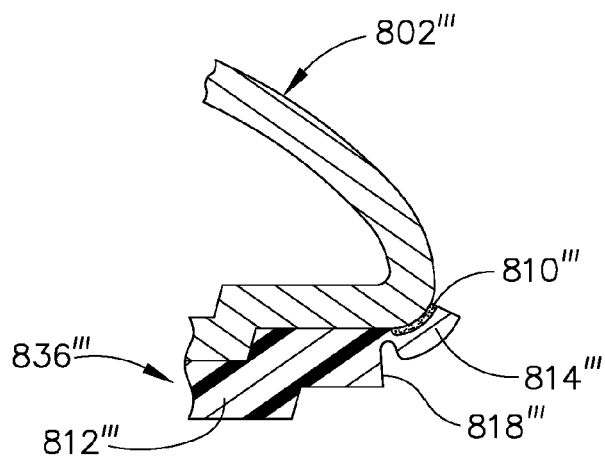
FIG. 37 is a detail view of a piece of buttress material releasably retained to an anvil in accordance with one non-limiting embodiment of the present invention.

As indicated above and referring to FIG. 34, sleeve 802 can include buttress material 836 thereon, wherein at least a portion buttress material 836 can be releasably attached to sleeve 802 using an adhesive, for example. In at least one embodiment, referring to FIG. 35, buttress material 836' can include body portion 812' and at least one side portion 814', wherein side portions 814' can be releasably attached to sleeve 802' with an adhesive 810'. In various embodiments, side portions 814' can be detached from sleeve 802' when a force is applied thereto. In at least one embodiment, similar to the above, such a force can be created when staples are deployed from the staple cartridge and engaged with the buttress material. In various embodiments, referring to FIG. 36, a piece of buttress material can further include at least one perforation and/or recess which can allow a tissue-contacting portion of the buttress material to be separated from a portion of the buttress material which is adhered to the end-effector. In at least one embodiment, buttress material 836" can include body portion 812" which can be configured to contact tissue positioned within the end-effector and, in addition, side portions 814" which can be adhered to anvil sleeve 802", for example, by adhesive 810". In various embodiments, buttress material 836" can further include one or more perforations 816" defined therein which can be located intermediate body portion 812" and side portions 814". In addition to or in lieu of side portions 814" separating from sleeve 802" as outlined above, body portion 812" can be configured to detach from side portions 814" along a path defined by perforations 816" when a force is applied thereto. In at least one such embodiment, side portions 814" can remain attached to sleeve 802" after body portion 812" has been separated therefrom. In other various embodiments, referring to FIG. 37, sleeve 802''' can include a piece of buttress material, such as buttress material 836''', for example, can include one or more recesses 818''' positioned intermediate body portion 812''' and side portions 814''' which can, similar to the above, allow body portion 812''' to separate from side portions 814'''.

Further to the above, in various embodiments, once the body portion has been released from the side portions, the end-effector can be moved away from the tissue and the buttress material stapled to the tissue. In at least one embodiment, the spent sleeve 802, for example, can then be slid off of anvil portion 826, discarded, and replaced with another sleeve. In at least one such embodiment, the replacement sleeve can include a piece of buttress material, such as buttress material 836, for example, positioned thereon such that the end-effector can be re-used. In various embodiments, the discarded sleeve can be sterilized, as described below, and another piece of buttress material can be attached to the sleeve such that it can be used once again.

Figure 38:
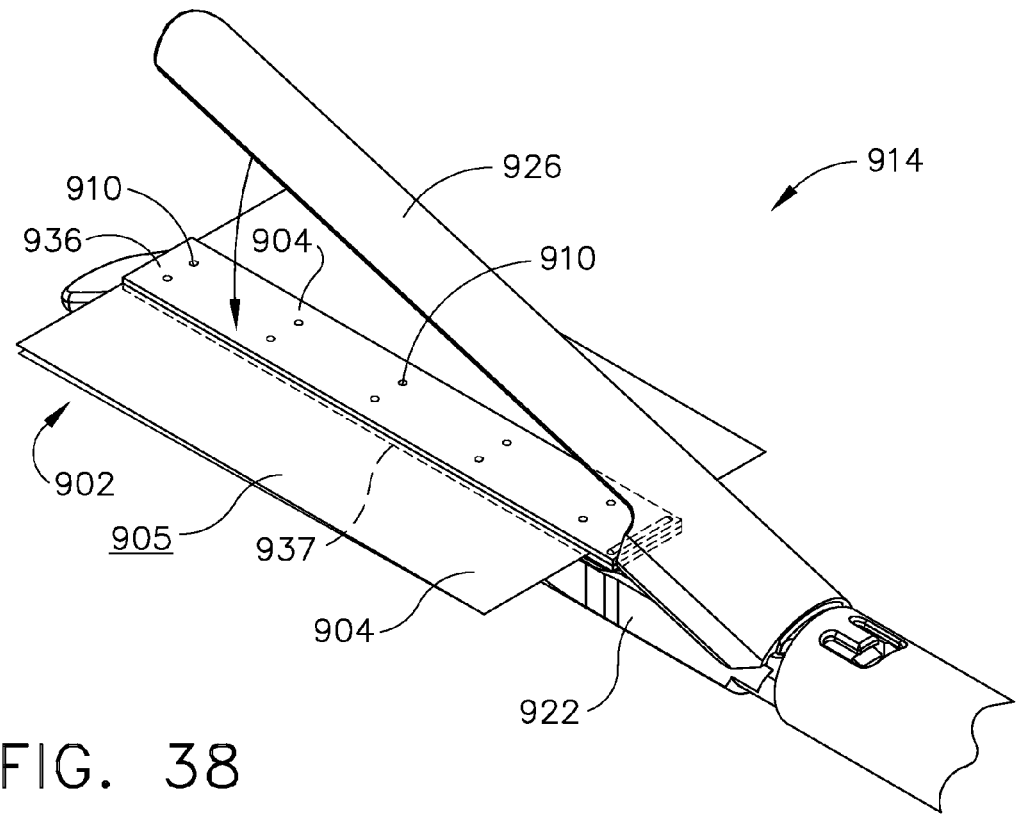
FIG. 38 is a perspective view of a package assembly including a piece of buttress material, wherein the package assembly is positioned within an open end-effector of a surgical instrument in accordance with one non-limiting embodiment of the present invention.
Figure 39:
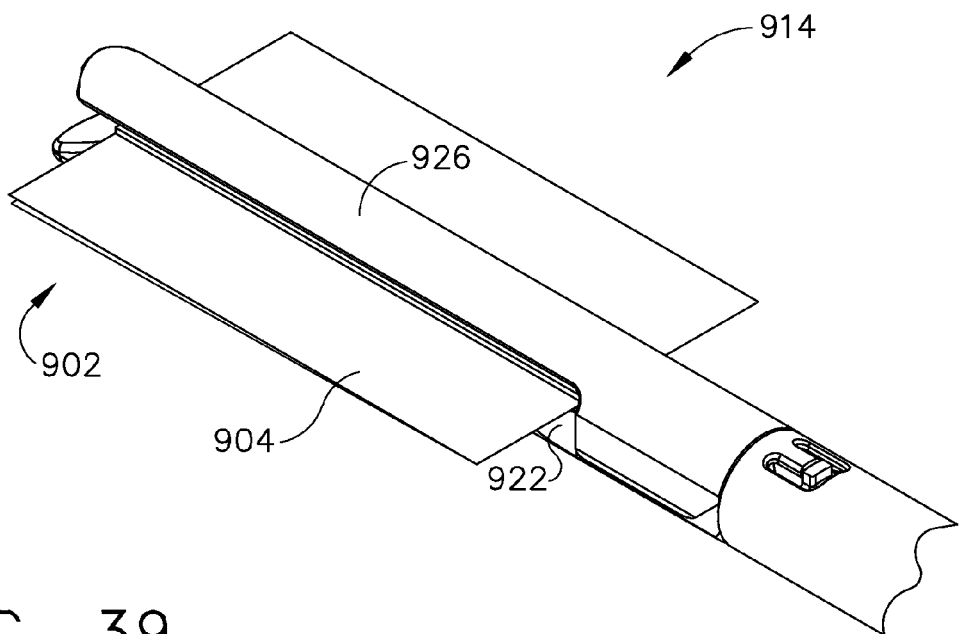
FIG. 39 is a perspective view of the package assembly of FIG. 38 illustrating the end-effector closed onto the package and the piece of buttress material.
Figure 40:
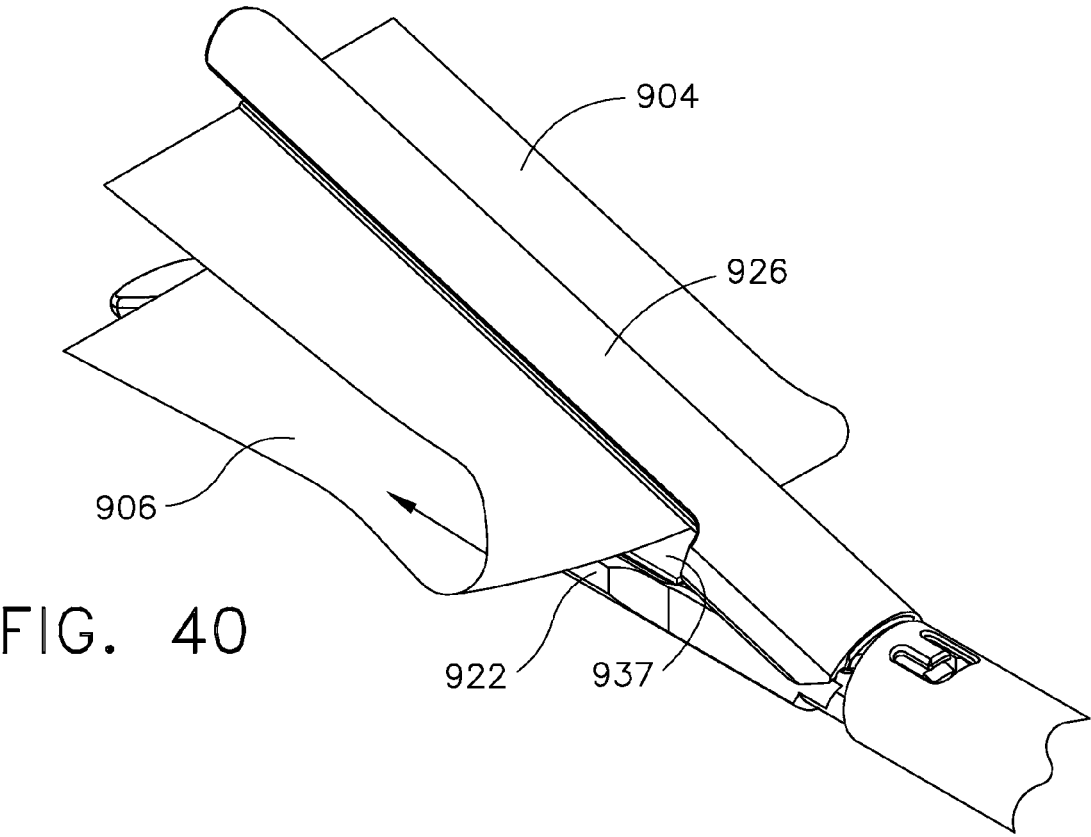
FIG. 40 is a perspective view of the package of FIG. 39 illustrating the piece of buttress material engaged with an anvil of the end-effector and the package being removed from the piece of buttress material in accordance with one non-limiting embodiment of the present invention.
Figure 41:
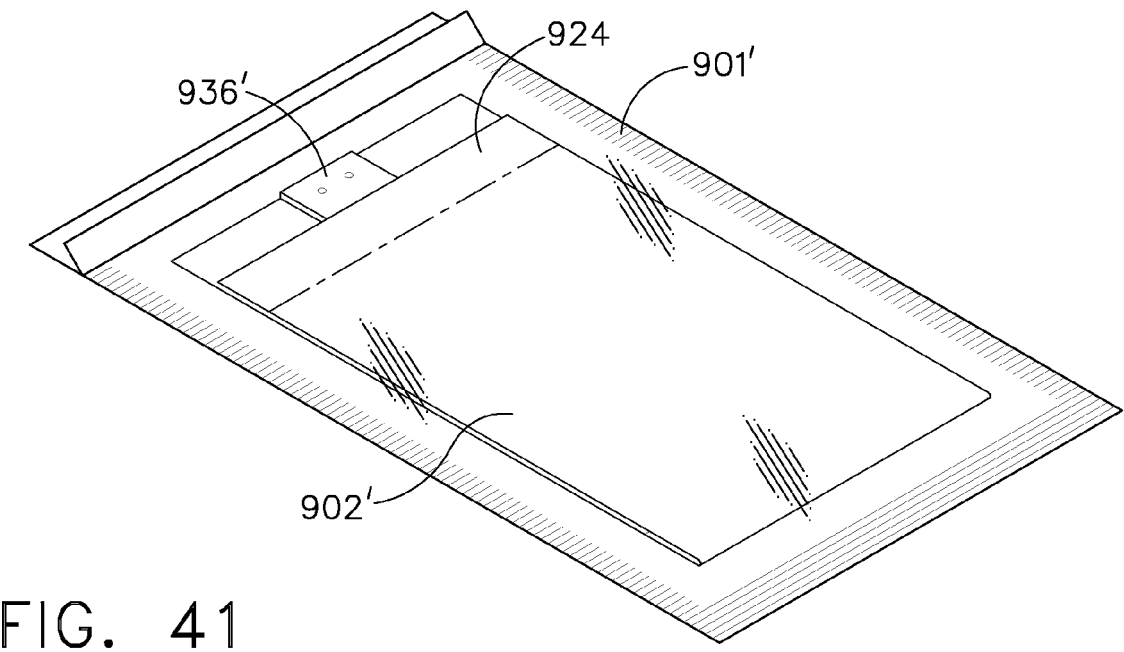
FIG. 41 is a perspective view of a package assembly for a piece of buttress material in a sterile outer package in accordance with one non-limiting embodiment of the present invention.

In various embodiments, a package including a piece of buttress material can be configured to apply the piece of buttress material to one of an anvil and a staple cartridge of an end-effector. In at least one embodiment, referring to FIGS. 38-40, package 902 can include first portion 904 having surface 905 which can be configured to releasably retain piece of buttress material 936 thereto. In various embodiments, surface 908 of buttress material 936 can include adhesive 910, wherein adhesive 910 can be configured to releasably attach buttress material 936 to anvil 926. In addition to first portion 904, package 902 can include second portion 906 attached to first portion 904 where second portion 906 can have a second piece of buttress material, such as buttress material 937, for example, attached thereto. In various embodiments, similar to buttress material 936, buttress material 937 can include adhesive thereon which can be utilized to releasably attach buttress material 937 to staple cartridge 922. In order to remove portions 904 and 906 from the pieces of buttress material, at least one of portions 904 and 906 can be grasped by the surgeon and pulled away from the pieces of buttress material as illustrated in FIG. 40. In effect, package 902 can be moved between a first, attached position and a second, detached position.

Figure 42:
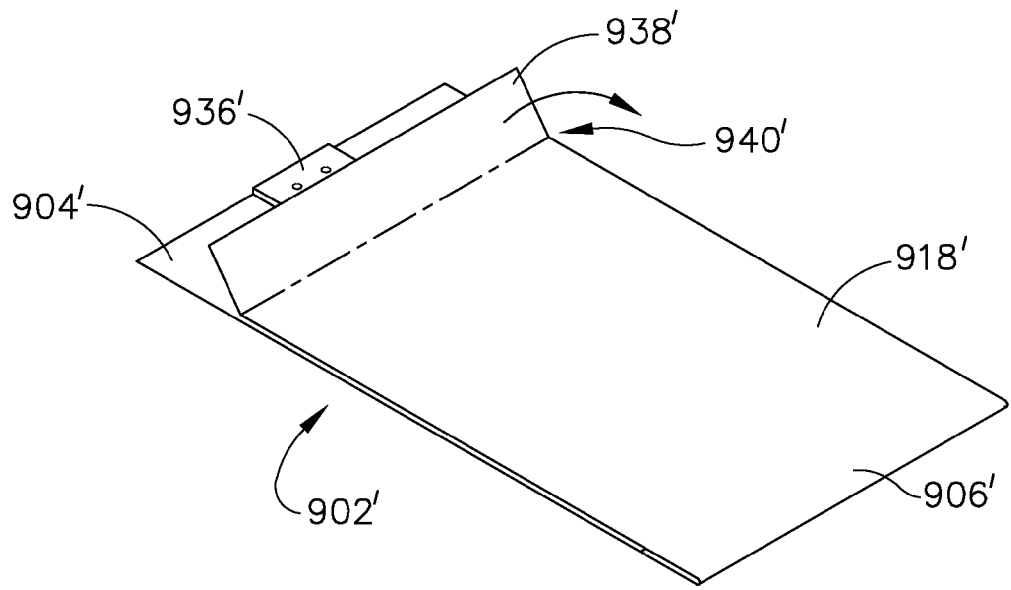
FIG. 42 is a perspective view of an inner package of the package assembly of FIG. 41 in an unopened position.
Figure 44:
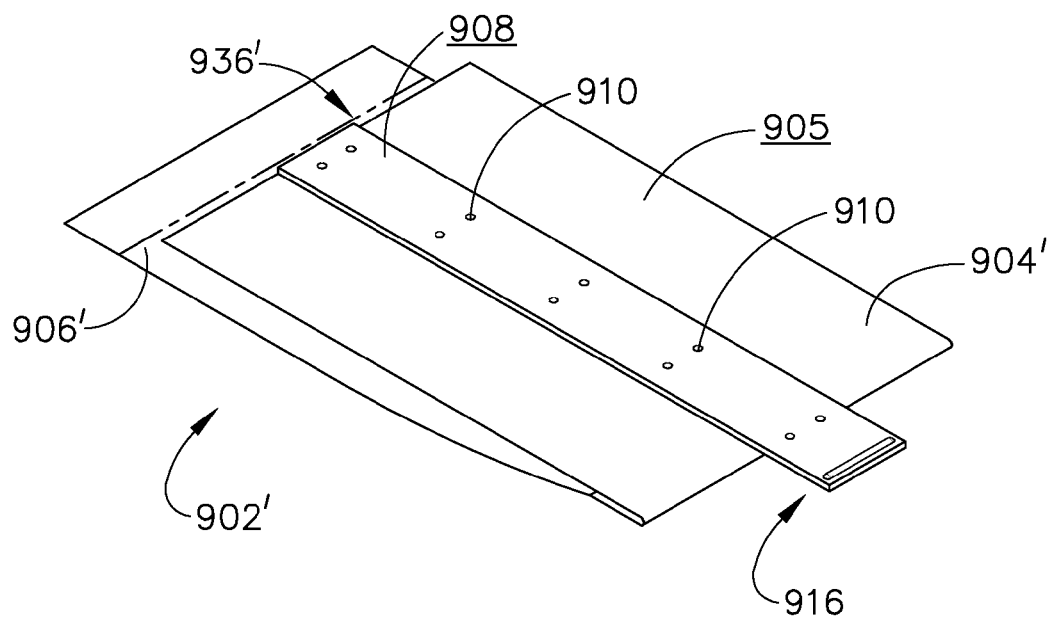
FIG. 44 is a perspective view of the package of FIG. 42 in an opened position.
Figure 43:
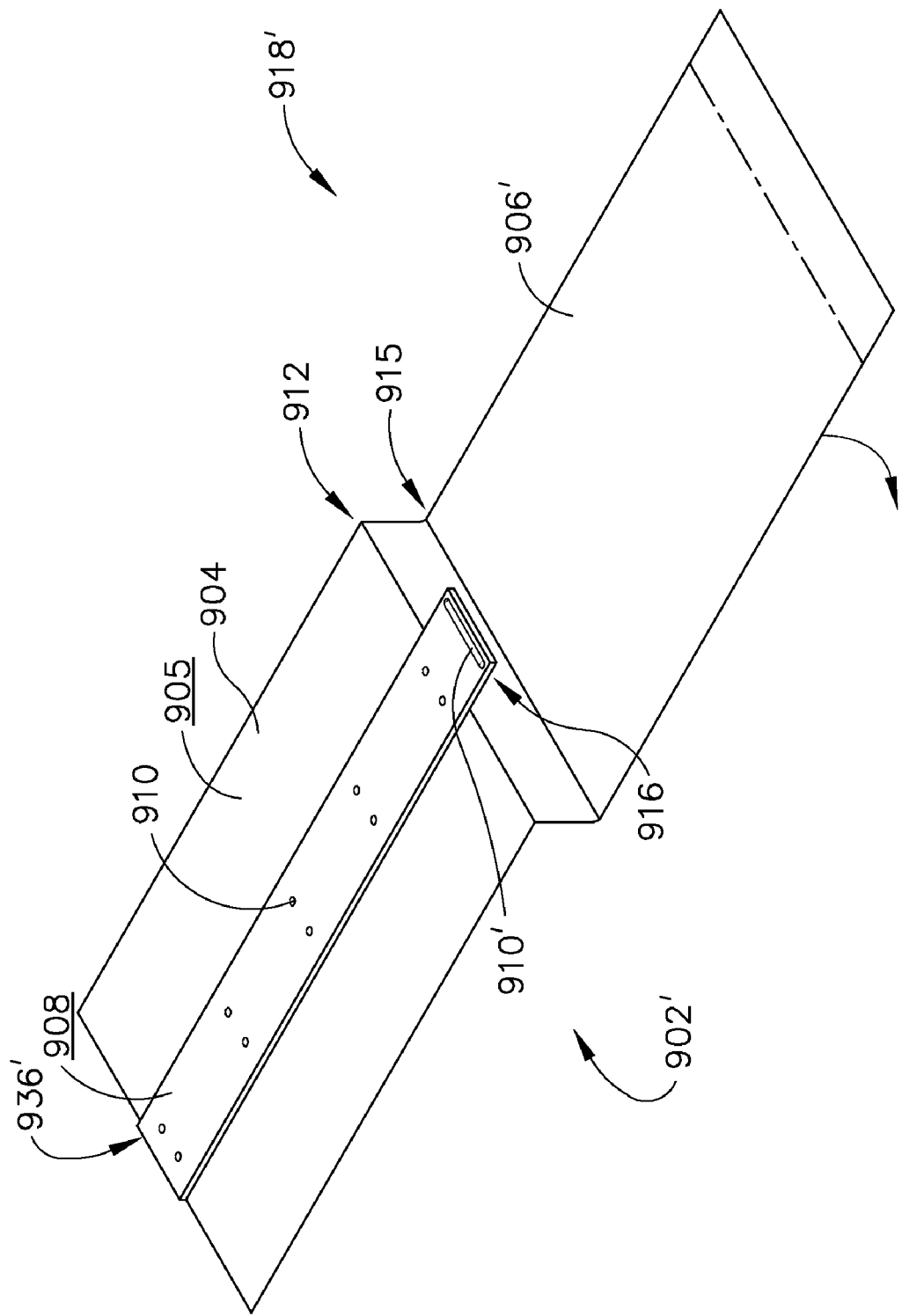
FIG. 43 is a perspective view of the package of FIG. 42 in a partially opened position.
Figure 45:
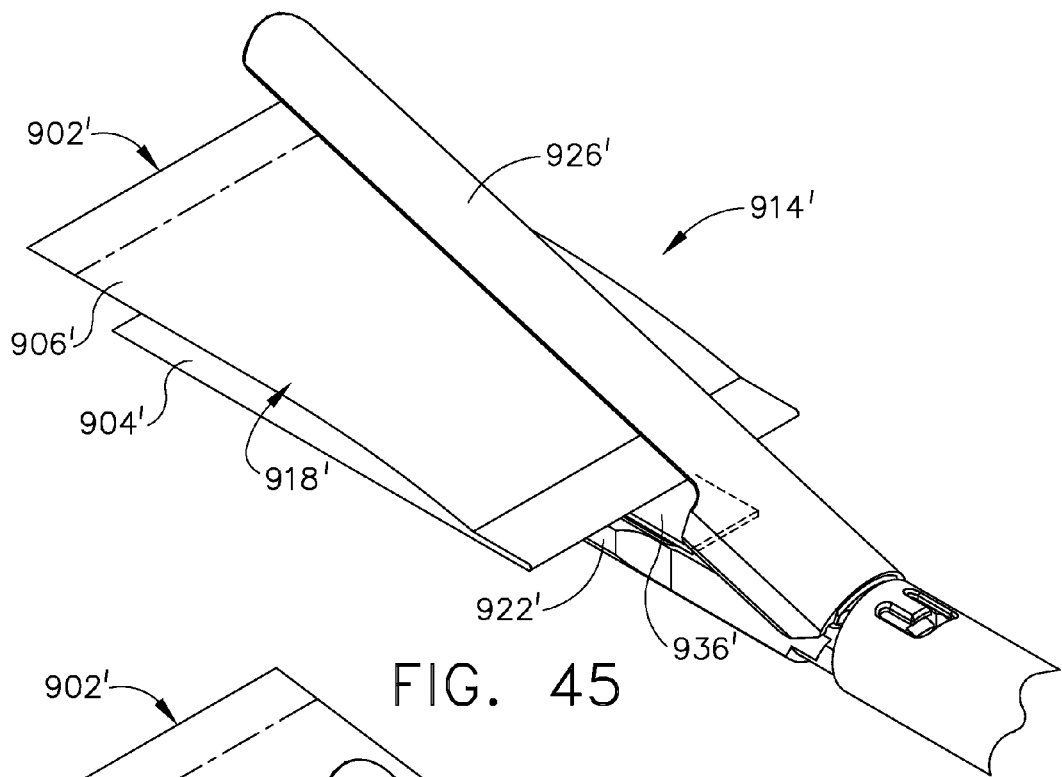
FIG. 45 is a perspective view of the package of FIG. 42 positioned within an open end-effector.
Figure 46:
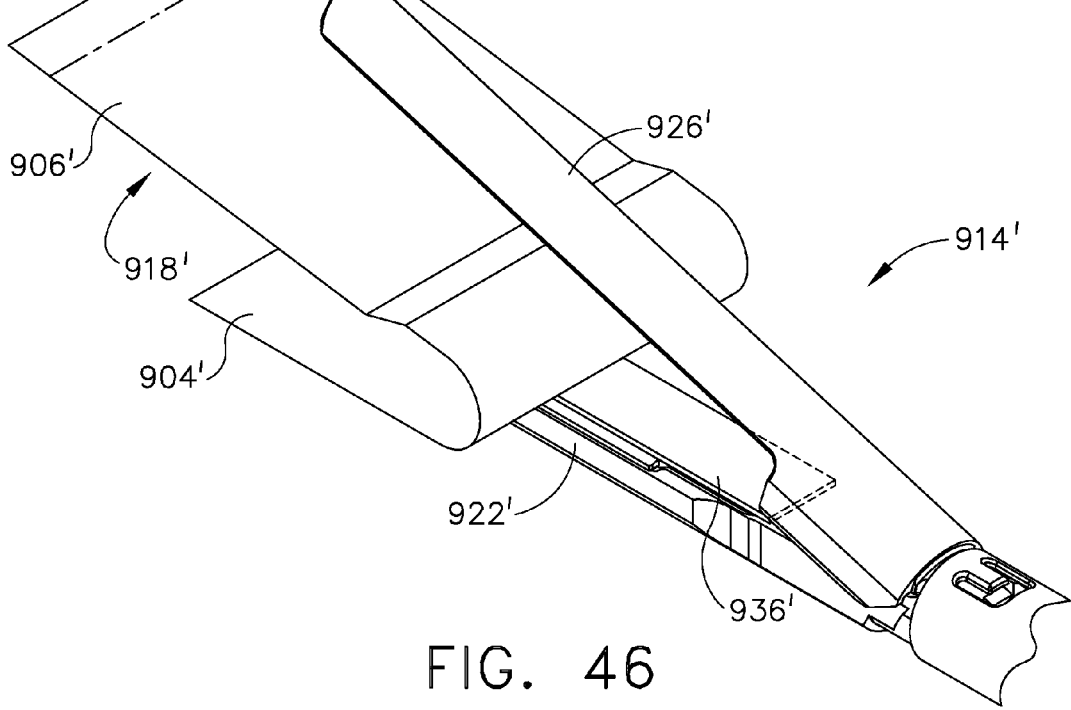
FIG. 46 is a perspective view of the package of FIG. 45 wherein the package is partially removed from the end-effector.

In various embodiments, referring to FIGS. 41-46, a package assembly for at least one piece of buttress material can include an outer package 901' which can be configured to enclose an inner package 902' in a sterile environment. In use, a surgeon can open outer package 901', remove inner package 902', and manipulate inner package 902' to expose buttress material 936'. In at least one embodiment, inner package 902' can include a cover sheet comprising first portion 904' and second portion 906', wherein the first and second portions can be configured to at least partially enclose buttress material 936' when they are in a first position as illustrated in FIG. 42. In various embodiments, a surgeon can rotate second portion 906' relative to first portion 904' by grasping and pulling tab 938' positioned on second end 940' of second portion 906', as illustrated in FIG. 42, and moving second portion 906' into a second position as sequentially illustrated in FIGS. 43 and 44. In at least one such embodiment, the surgeon can rotate second portion 906' relative to first portion 904' until second portion 906' is at least partially positioned adjacent to first portion 904'.

Thereafter, in various embodiments, buttress material 936' can then be aligned with one of an anvil and/or staple cartridge of an end-effector as described above. In at least one embodiment, referring to FIGS. 45 and 46, inner package 902' can be inserted within end-effector 914' intermediate anvil 926' and staple cartridge 922' such that buttress material 936' can be aligned with staple cartridge 922', for example. In various embodiments, similar to the above, anvil 926' can be rotated toward staple cartridge 922' and clamped onto package 902' and buttress material 936' such that buttress material 936' can be pressed against staple cartridge 922' and adhesive 910 can secure buttress material 936' thereto. Thereafter, anvil 926' can be reopened and sheet 918' can be peeled, or otherwise removed, from buttress material 936'.

Figure 47:
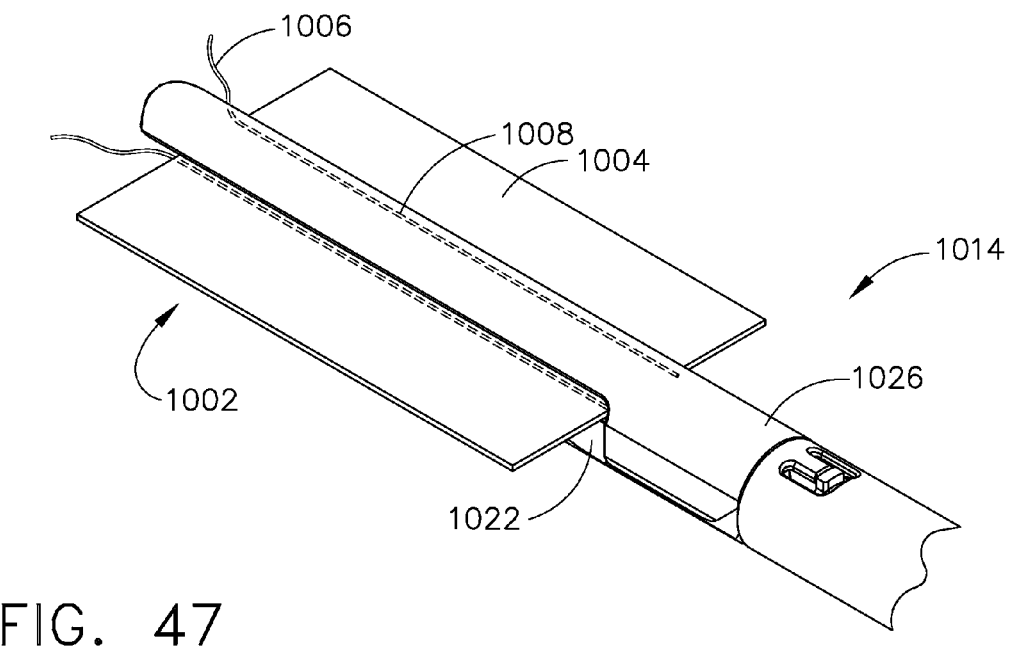
FIG. 47 is a perspective view of an applicator assembly for a piece of buttress material, wherein the applicator assembly is positioned within an end-effector of a surgical instrument in accordance with one non-limiting embodiment of the present invention.
Figure 48:
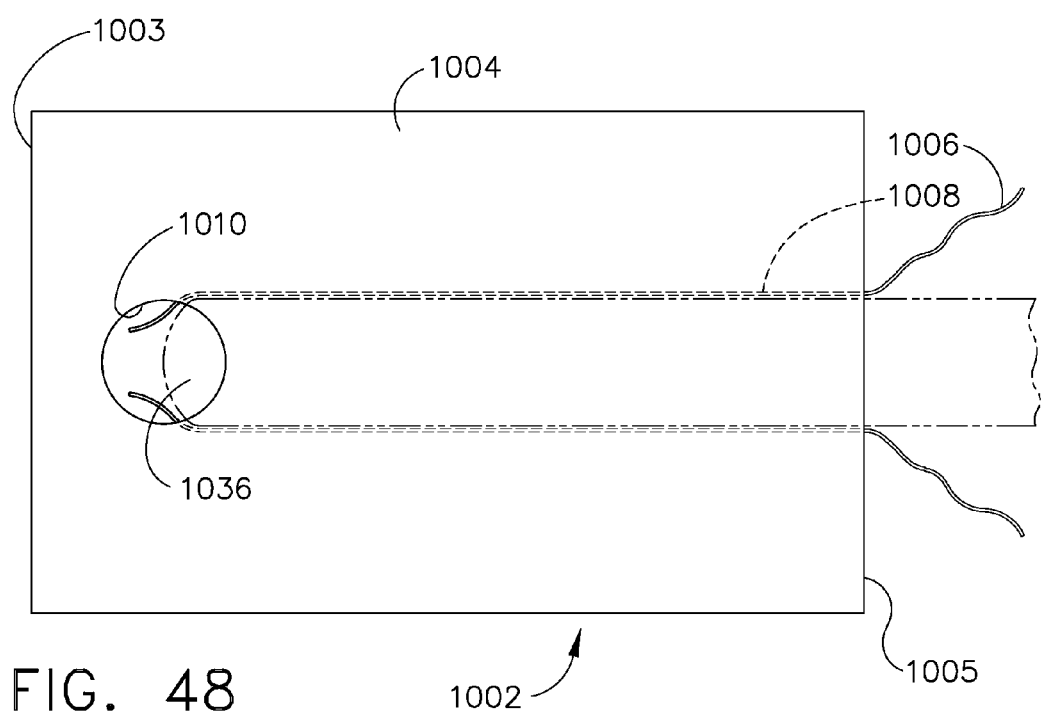
FIG. 48 is a top view of the applicator assembly of FIG. 47.
Figure 49:
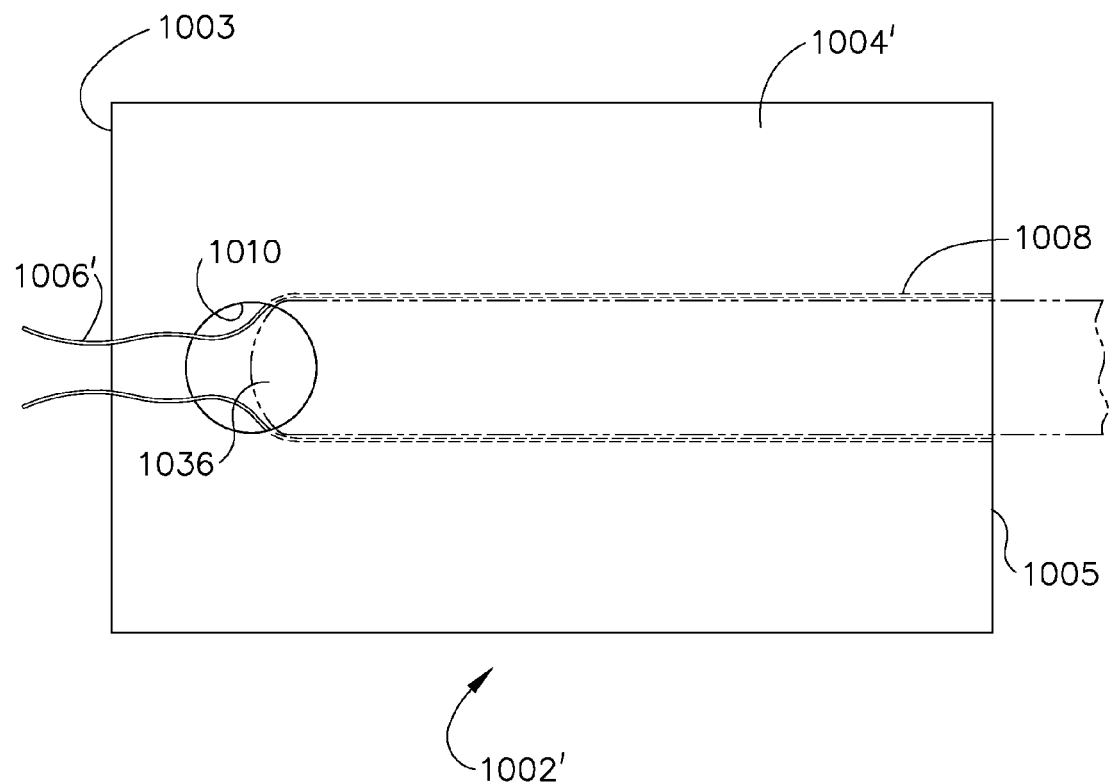
FIG. 49 is a top view of an applicator assembly in accordance with one alternative non-limiting embodiment of the present invention.

In various alternative embodiments, a package assembly can include one or more draw strings configured to detach a cover sheet from a buttress material contained within the package assembly. In at least one such embodiment, the cover sheet can be manipulated to expose the buttress material, the buttress material can be secured to an end effector, and the draw strings can be pulled proximally, or distally, to detach the cover sheet from the buttress material. In various other embodiments, referring to FIGS. 47 and 48, draw strings can be attached to a portion of the buttress material such that a handle portion, for example, of the buttress material can be removed from a tissue-contacting portion of the buttress material. In at least one such embodiment, buttress material 1002 can be clamped between an anvil and a staple cartridge of an end effector, and a force can be applied to draw strings 1006 which are attached to handle portion 1004 of buttress material 1002. In various embodiments, as a result, distal end 1003 of buttress material 1002 can be pulled toward proximal end 1005 by draw strings 1006 such that handle portion 1004 can detach from tissue-contacting portion 1036 along perforations 1008. In at least one embodiment, buttress material 1002 can further include aperture 1010 which can be located at the distal end of tissue-contacting portion 1036, wherein aperture 1010 can define a pre-detached point between handle portion 1004 and tissue-contacting portion 1036 in order to reduce the force required to detach handle portion 1004. In at least one embodiment, referring to FIG. 49, at least one draw string 1006' can be attached to handle portion 1004' of buttress material 1002' such that proximal end 1005 can be pulled toward distal end 1003 to remove handle portion 1004.

Figure 50:
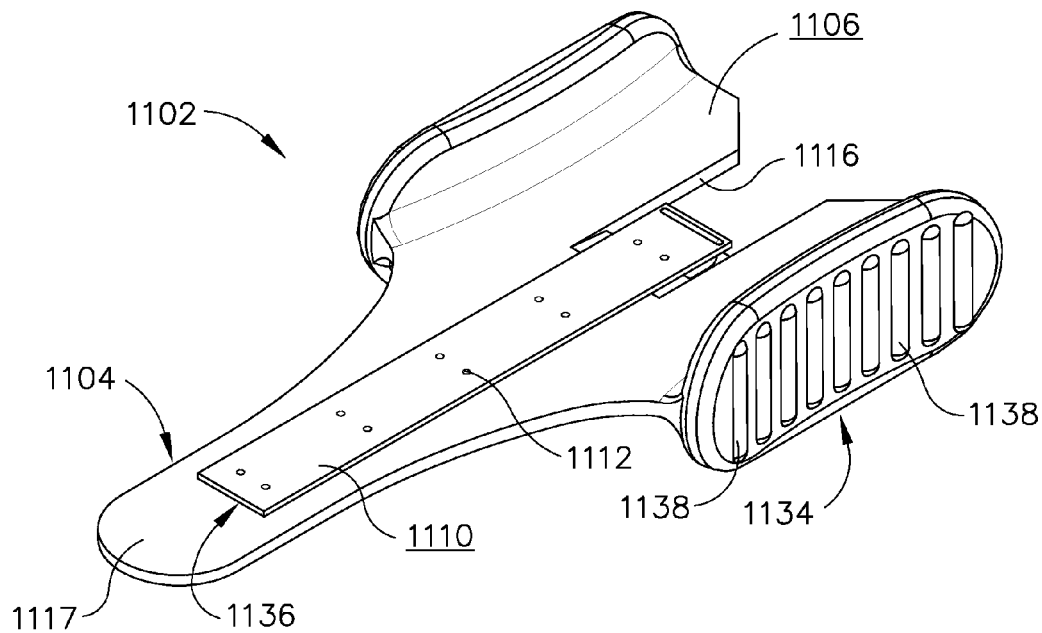
FIG. 50 is a perspective view of a buttress material applicator assembly in accordance with one non-limiting embodiment of the present invention.
Figure 51:
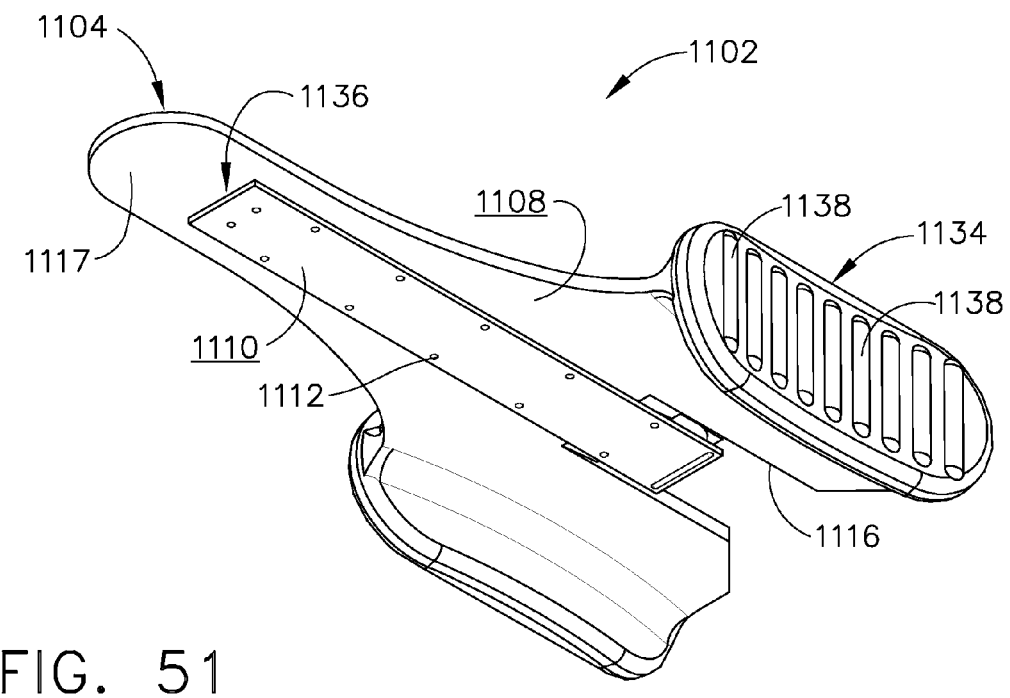
FIG. 51 is another perspective view of the buttress material applicator assembly of FIG. 50.
Figure 52:
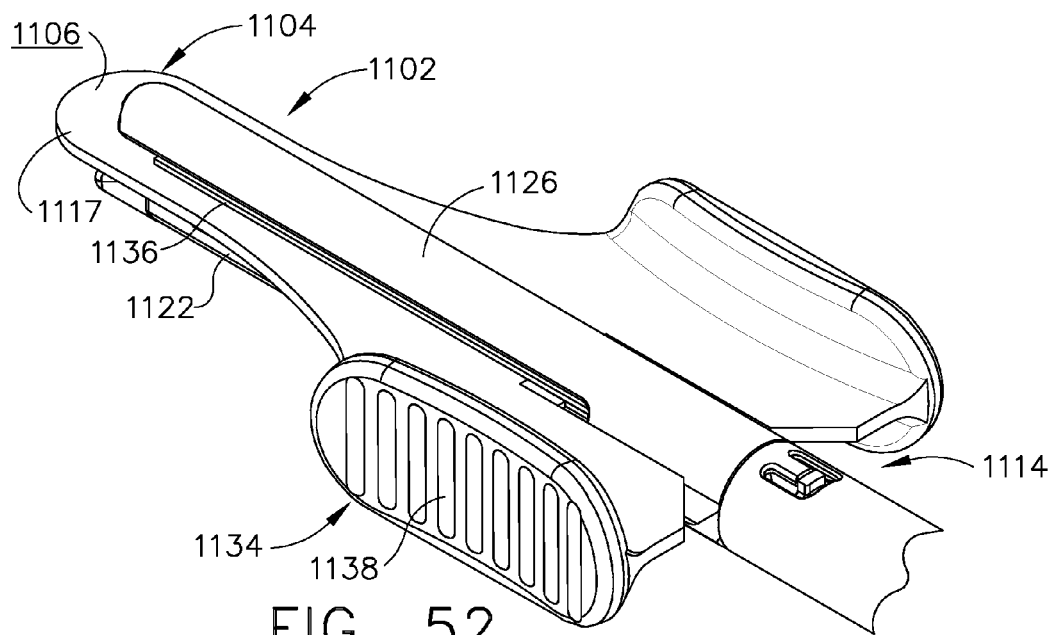
FIG. 52 is a perspective view of the buttress material applicator assembly of FIG. 50 positioned within an end-effector of a surgical instrument.
Figure 53:
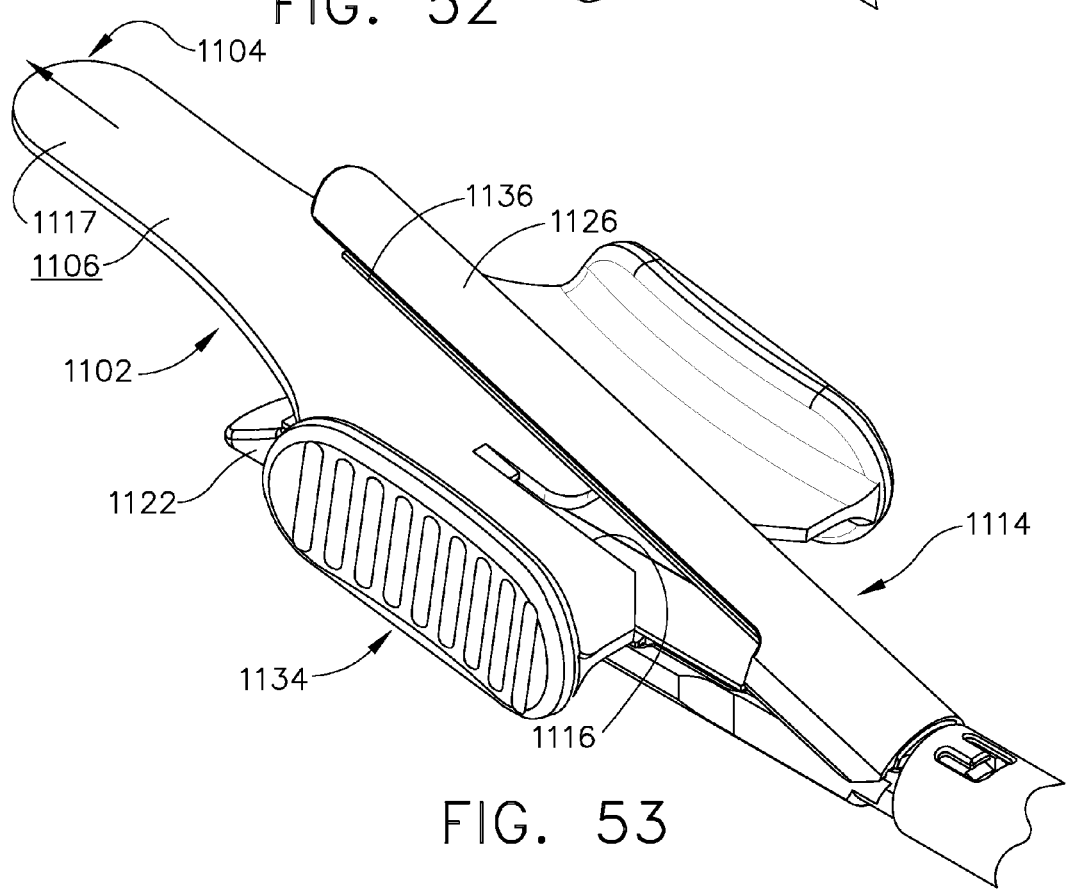
FIG. 53 is a perspective view of the buttress material applicator assembly of FIG. 50 partially removed from the end-effector.

In various embodiments, an applicator can be used to apply a piece of buttress material to at least one of an anvil and a staple cartridge of an end-effector. In at least one embodiment, referring to FIGS. 50-53, applicator assembly 1102 can comprise applicator 1104 and at least one piece of buttress material 1136, wherein applicator 1104 can include at least one surface for supporting buttress material 1136 thereon. In at least one such embodiment, applicator 1104 can include top surface 1106 and bottom surface 1108 wherein each of the top and bottom surfaces can be configured to releasably receive at least one piece of buttress material 1136. In various embodiments, each piece of buttress material 1136 can be releasably attached to the top and bottom surfaces of applicator 1104 through the use of an adhesive and/or mechanical attachment member, for example. Referring to FIGS. 50 and 51, each piece of buttress material 1136 can include a face 1110 which can be at least partially coated with an adhesive to retain face 1110 to the end-effector. In at least one such embodiment, the adhesive can be applied to buttress material 1136 at a plurality of locations 1112.

In order to apply a piece of buttress material to a staple cartridge and/or anvil of an end-effector assembly using an applicator such as applicator 1104, for example, the applicator can be at least partially positioned intermediate the staple cartridge and the anvil such that the anvil can be closed onto the buttress material. In various embodiments, referring to FIGS. 52 and 53, applicator assembly 1102 can be at least partially positioned intermediate anvil 1126 and staple cartridge 1122 of end-effector 1114 such that anvil 1126 can be aligned with and closed onto buttress material 1136. In at least one embodiment, applicator 1104 can further include alignment slot 1116 at a first end and tongue portion 1117 at a second end, wherein a surgeon can use alignment slot 1116 to align and position applicator assembly 1102 within end-effector 1114. In at least one such embodiment, alignment slot 1116 can be configured such that end-effector 1114 is closely received between the sidewalls of alignment slot 1116. Owing to adhesive 1112, the pieces of buttress material 1136 can be adhered to anvil 1126 and staple cartridge 1122 such that when anvil 1126 is reopened, applicator 1104 can be removed from end-effector assembly 1114, leaving behind the pieces of buttress material within the end-effector.

In various embodiments, at least one protective sheet (not illustrated), similar to sheet 918, for example, can be positioned over face 1110 such that applicator 1104 can be positioned and repositioned on one of the anvil and the staple cartridge of end-effector 1114 without adhesive 1112, for example, bonding to the anvil and/or the staple cartridge. In at least one such embodiment, the sheets can be removed by the surgeon once the applicator is properly positioned and aligned within the end-effector to allow the adhesive to contact the staple cartridge and/or anvil of the end-effector. In various embodiments, in addition to or in lieu of tongue 1117, an applicator can include at least one grip, such as grips 1134, for example, which can be configured to allow a surgeon to more easily manipulate the applicator within an end-effector. In at least one embodiment, a first grip 1134 can be provided on a first side of applicator 1104, and, in addition, a second grip 1134 can be provided on a second side of the applicator. In various embodiments, a grip can include ridges 1138 which can be configured to allow the surgeon to more easily handle applicator 1104. To this end, at least a portion of grips 1134 can be comprised of a soft or elastic material such as rubber, for example.

In other various embodiments, although not illustrated, the packaging for at least one piece of buttress material can comprise a tubular sleeve which can be configured to be positioned around at least one of an anvil and a staple cartridge. In at least one embodiment, the buttress material can include an adhesive thereon which can be configured to releasably attach the piece of buttress material to at least one of the anvil and the staple cartridge. In at least one such embodiment, the tubular sleeve can be configured to receive at least one of the anvil and the staple cartridge therein such that the anvil and/or staple cartridge are aligned with a piece of buttress material within the tubular sleeve. In various embodiments, a tubular sleeve can include a middle wall extending between a first side and a second side of an inner perimeter of the sleeve. In various embodiments, the middle wall can include a top surface and a bottom surface, wherein the top and bottom surfaces can each be configured to releasably retain a piece of buttress material thereto. In at least one such embodiment, the end-effector can be aligned relative to the middle wall and can be closed onto the middle wall to attach the buttress material to the anvil and/or staple cartridge.

Figure 54:
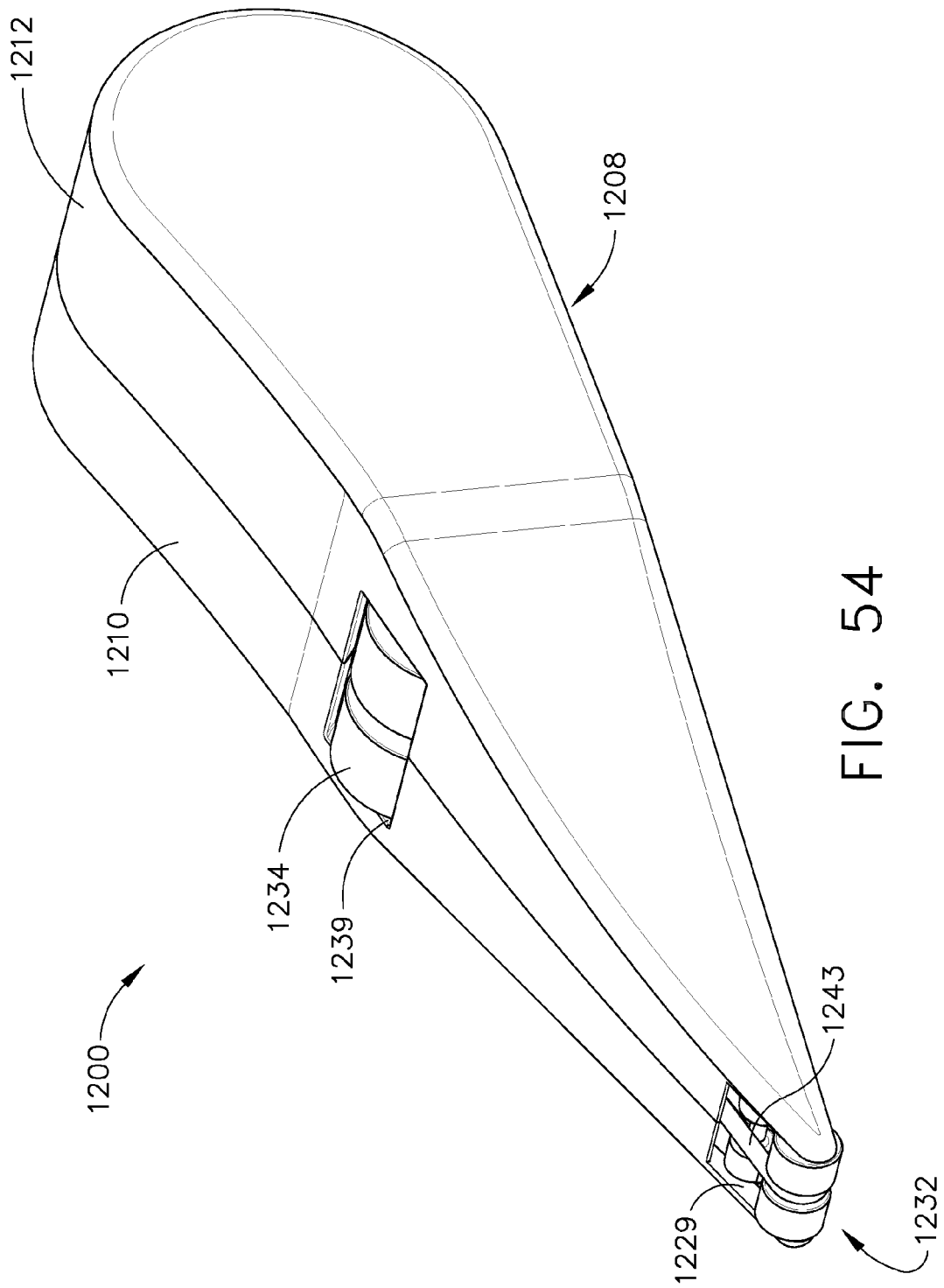
FIG. 54 is a perspective view of a buttress material applicator configured to apply at least one piece of buttress material to an end-effector of a surgical instrument in accordance with one non-limiting embodiment of the present invention.
Figure 57:
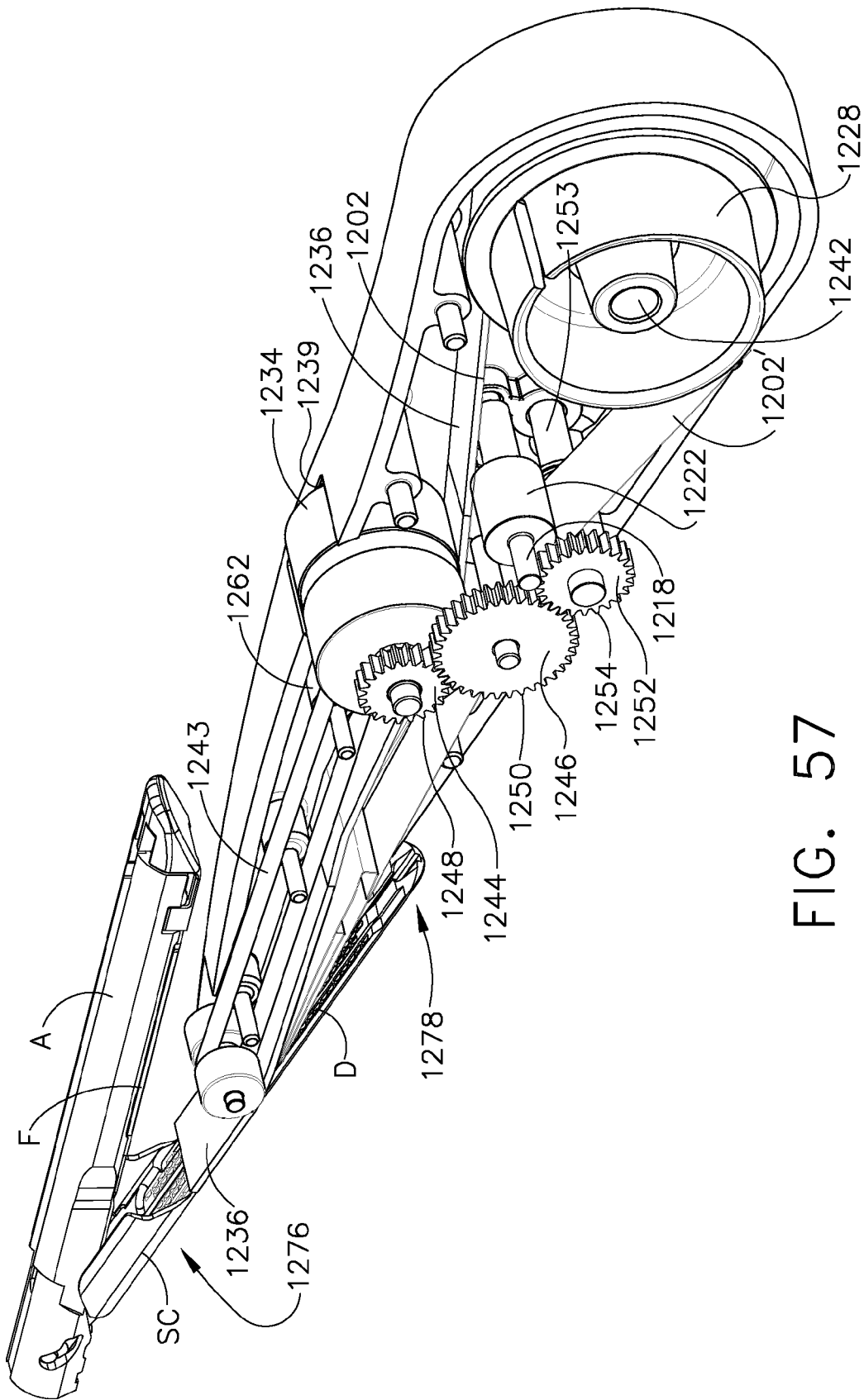
FIG. 57 is a perspective view of the buttress material applicator of FIG. 54 with some components removed.
Figure 58:
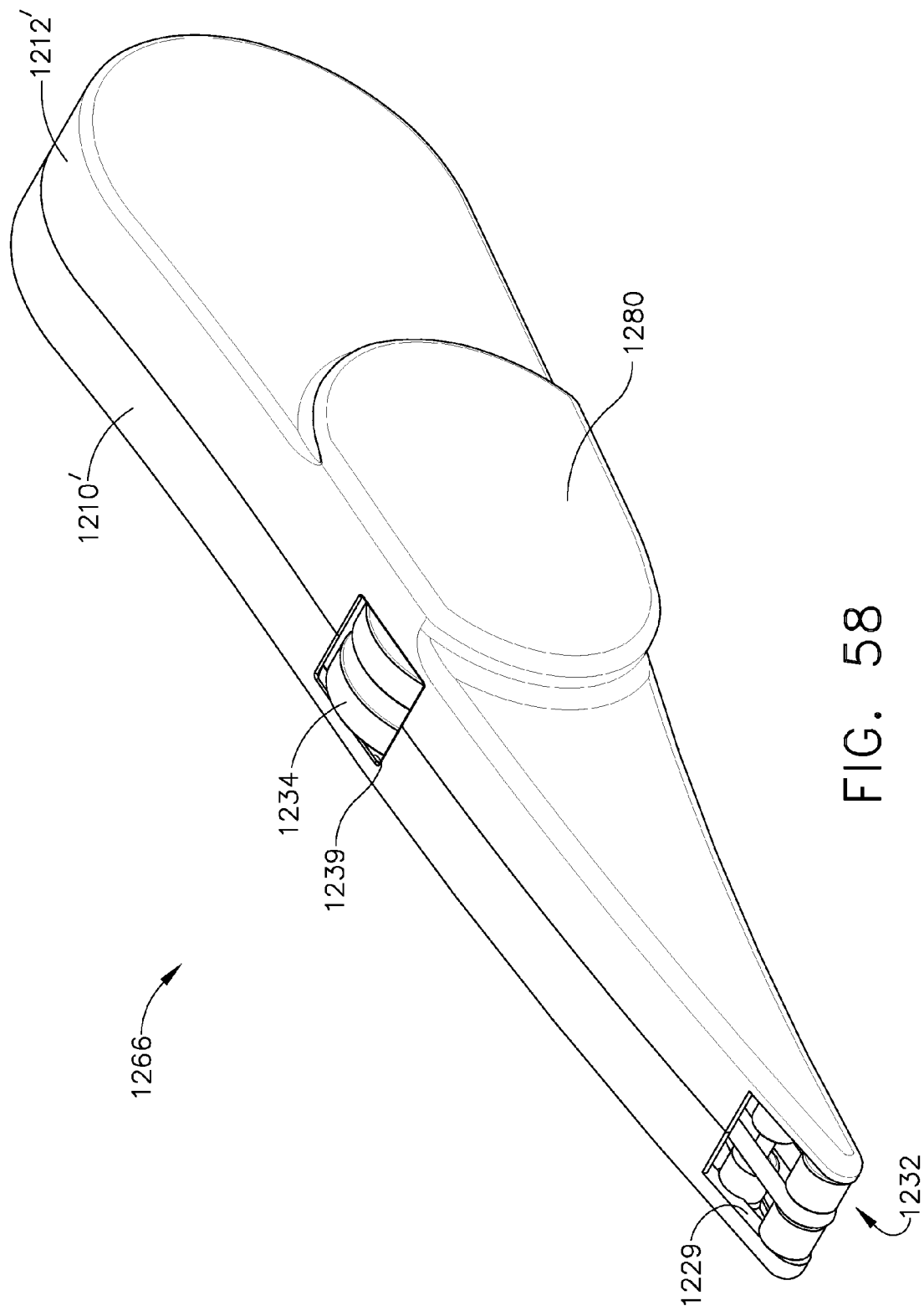
FIG. 58 is a perspective view of an alternative buttress material applicator configured to apply at least one piece of buttress material to an end-effector of a surgical instrument in accordance with another non-limiting embodiment of the present invention.
Figure 59:
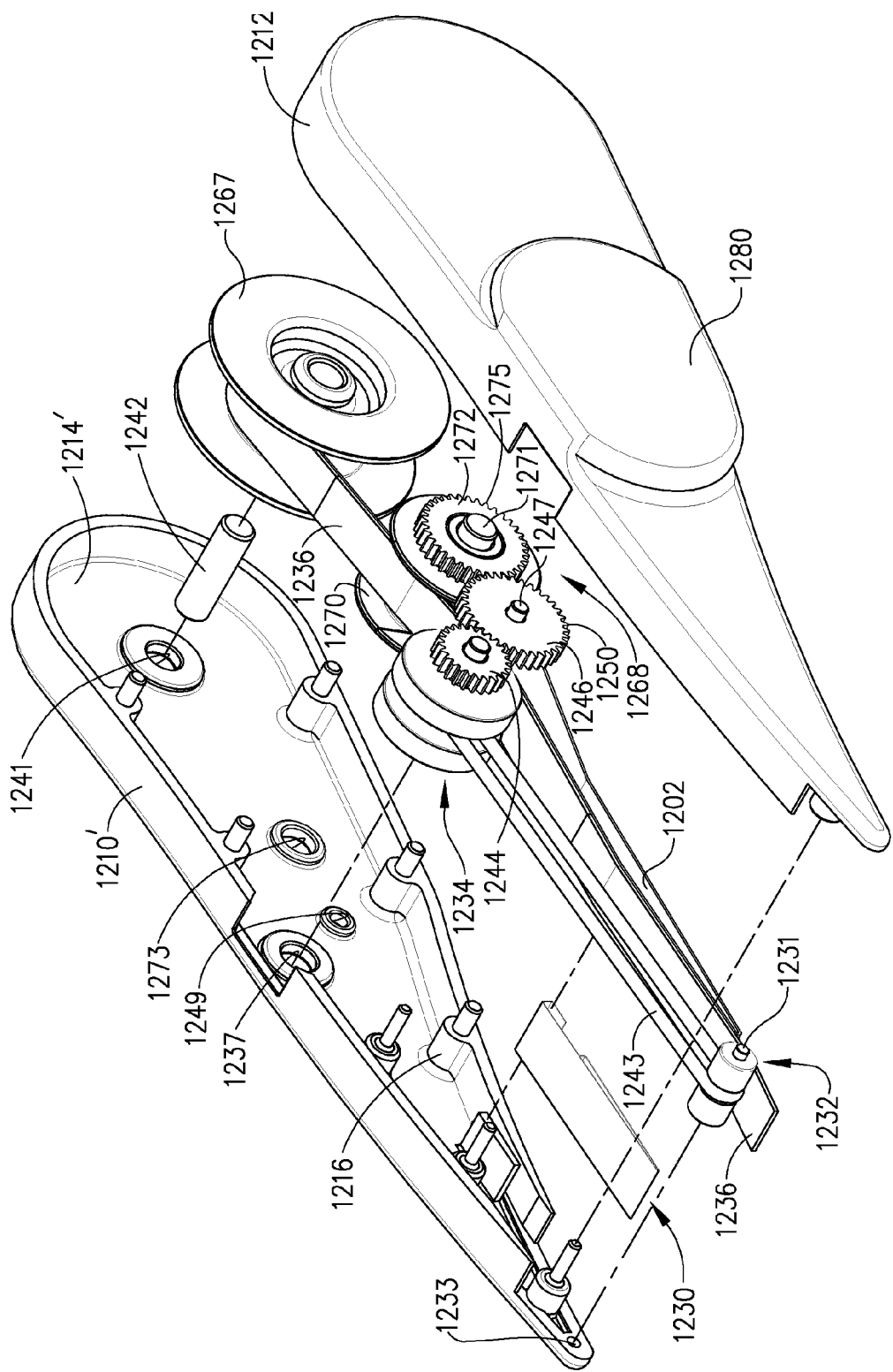
FIG. 59 is an exploded perspective view of the buttress material applicator of FIG. 58.
Figure 60:
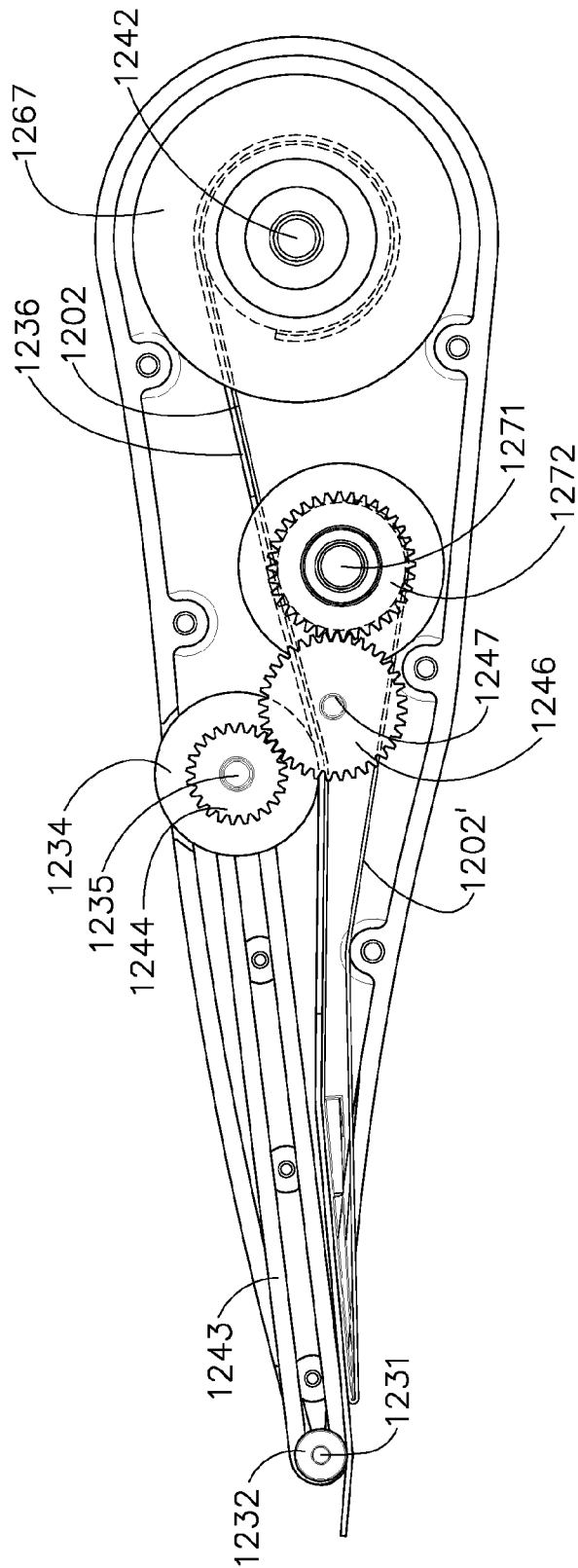
FIG. 60 is an elevational view of the buttress material applicator of FIG. 58 with some components removed.

In various embodiments, a buttress material dispenser can be utilized to dispense buttress material. In at least one embodiment, referring to FIGS. 54 and 55, dispenser 1200 can be configured to dispense buttress material 1236 from a housing assembly comprised of housing portions 1210 and 1212. As described in greater detail below, dispenser 1200 can include a roll, or spool, 1224 of buttress material wherein the buttress material can be dispensed from spool 1224 onto an end effector of a surgical instrument as illustrated in FIG. 57. In various embodiments, buttress material 1236 can be adhered to, or otherwise supported by, carrier strip 1202 such that, as buttress material 1236 is dispensed, buttress material 1236 can be separated from carrier strip 1202. In various embodiments, referring to FIGS. 54-57, carrier strip 1202 can include surface 1204 which can be configured to receive buttress material 1236 thereon. In various embodiments, buttress material 1236 can be divided into pieces before and/or after it is placed onto surface 1204. In at least one embodiment, the pieces of buttress material 1236 can each have a width which is the same as or less than the width of surface 1204 and, in various embodiments, the pieces of buttress material can be releasably attached to surface 1204 of carrier 1202 using a low-strength adhesive, for example.

In various embodiments, referring to FIGS. 54-57, internal wall 1214 of first housing portion 1210 can include a plurality of connectors 1216 extending therefrom. In at least one embodiment, connectors 1216 can be engaged with other connectors extending from, or apertures within, an internal wall of second portion 1212 in order to secure the first and second housing portions together. In various embodiments, referring to FIG. 56, dispenser 1200 can further include spool pin 1242 which can be configured to rotatably support spool 1224. In at least one such embodiment, spool pin 1242 can be engaged with aperture 1241 in housing portion 1210 and an aperture (not illustrated) in second portion 1212. In various embodiments, spool pin 1242 can be mounted to spool 1242 such that they can be rotated together. As outlined above, buttress material 1236 and carrier strip 1202 can be unspooled from spool 1224 as buttress material 1236 is dispensed. In at least one embodiment, a force can be applied to buttress material 1236 such that it can be manually pulled out of dispenser 1200. In other various embodiments, as described in greater detail below, buttress dispenser 1200 can further include thumb roller 1234 which can be sufficiently engaged with buttress material 1236 such that a surgeon, or other clinician, can rotate thumb roller 1234 and push buttress material 1236 out of dispenser 1200. In at least one embodiment, referring to FIG. 55, dispenser 1200 can further include thumb roller pin 1235 which can be configured to rotatably support thumb roller 1234 within the dispenser housing. In at least one embodiment, thumb roller 1234 can be mounted to pin 1235 such that they can be rotated together about an axis defined by aperture 1249 in first housing portion 1210 and an aperture (not illustrated) in second housing portion 1212.

Figure 55:
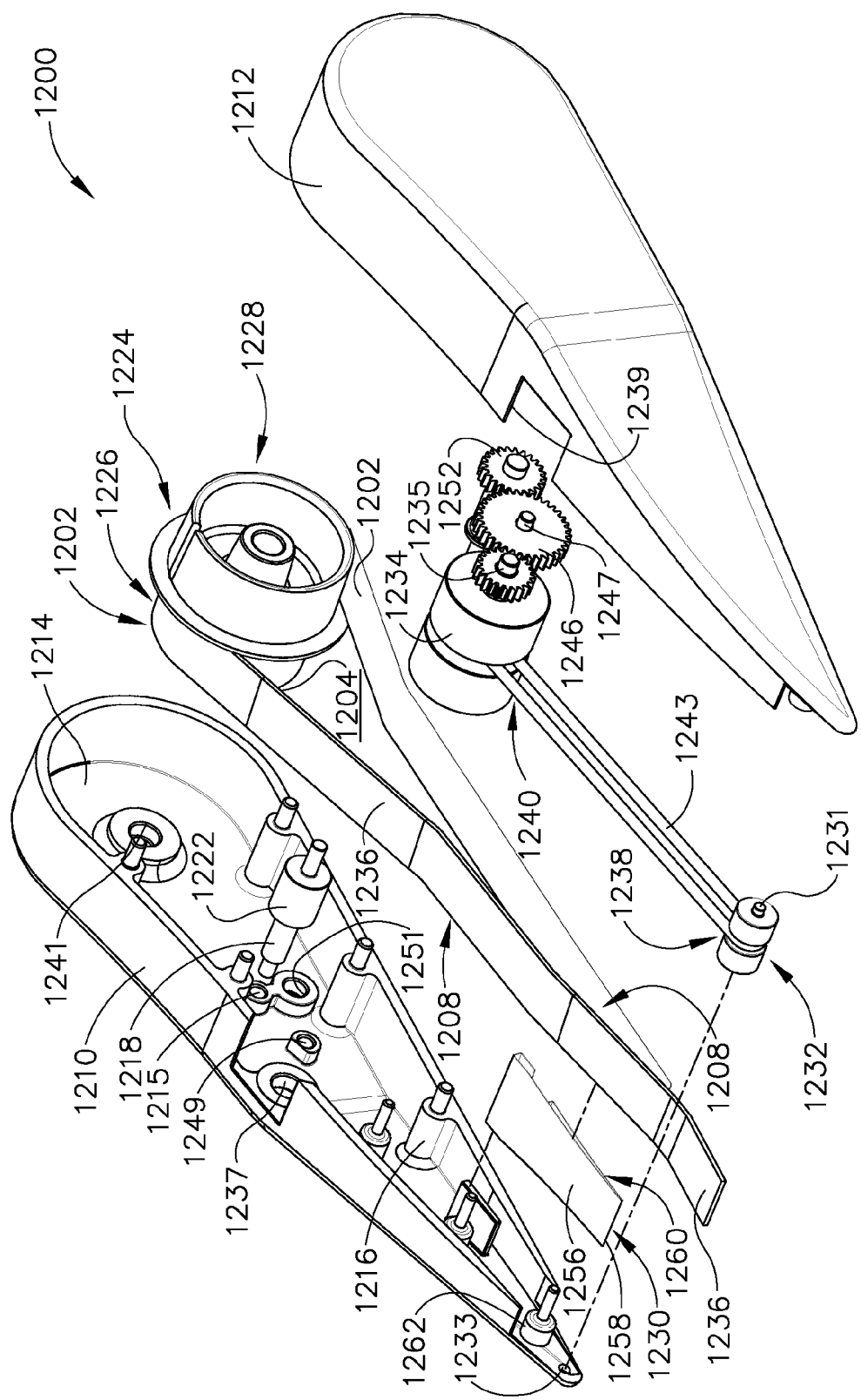
FIG. 55 is an exploded view of the buttress material applicator of FIG. 54.
Figure 56:
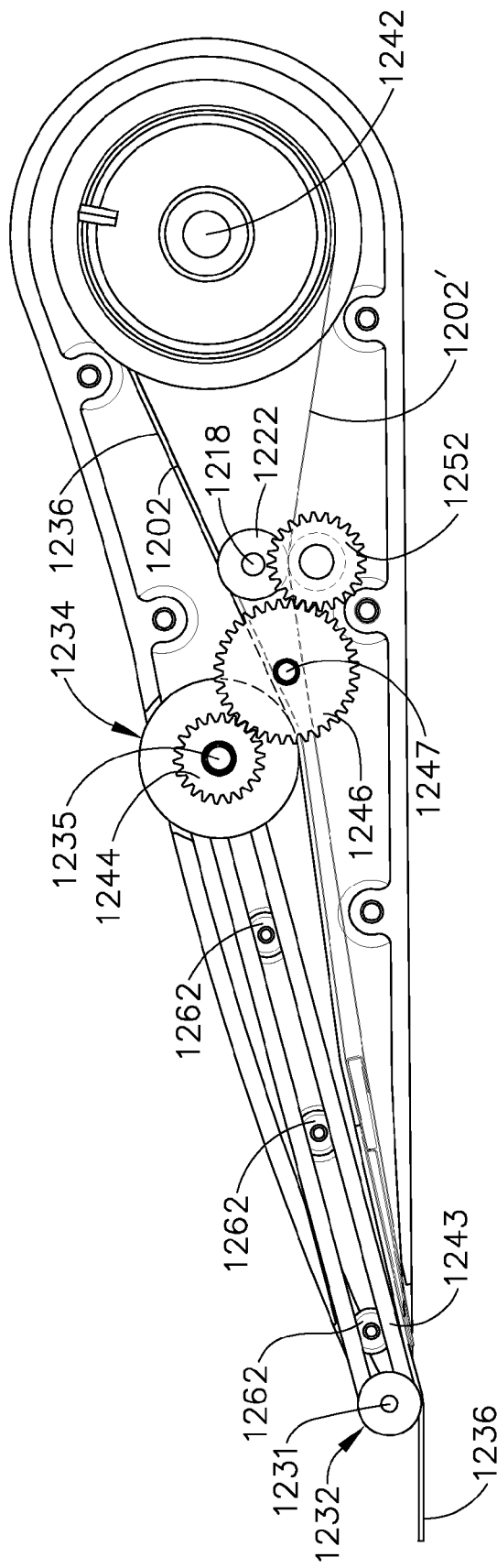
FIG. 56 is an elevational view of the buttress material applicator of FIG. 54 with some components removed.

In various embodiments, referring to FIG. 55, thumb roller 1234 can be configured to extend at least partially through aperture 1239 in the dispenser housing such that thumb roller 1234 can be rotated by the surgeon. In at least one embodiment, thumb roller 1234 can be configured to operatively contact, or frictionally engage, buttress material 1236 and/or carrier 1202 such that the rotation of thumb roller 1234 can drive or motivate buttress material 1236 distally toward drive roller 1232. In addition to or in lieu of the above, drive roller 1232 can be configured to operatively contact, or frictionally engage, buttress material 1236 and/or carrier 1202. In at least one embodiment, drive roller 1232 can be operably engaged with thumb roller 1234 via drive belt 1243, for example, such that the rotation of thumb roller 1234 can be transmitted to drive roller 1232. Although a drive belt is illustrated, any other suitable device, such as a drive chain or band, for example, can be used. In various embodiments, at least one of housing portions 1210 and 1212 can include guides 1262 which can be configured to align drive belt 1243 with thumb roller 1234 and drive roller 1232.

As described above, carrier strip 1202 can be separated from buttress material 1236 as buttress material 1236 is dispensed from dispenser 1200. In various embodiments, dispenser 1200 can further include carrier strip collector 1228 which can be configured to wind up carrier strip 1202 after it has been detached from buttress material 1236. In at least one embodiment, carrier strip collector 1238 can be mounted to at least one of spool 1224 and spool pin 1242 such that spool 1224 and strip collector 1228 can be rotated in unison. In at least one such embodiment, carrier strip 1202 can be collected around strip collector 1228 in a direction which is opposite to the direction in which buttress material 1234 is dispensed from spool 1224. As a result, buttress material 1234 can be dispensed and carrier strip 1202 can be collected simultaneously. In various embodiments, dispenser 1200 can further include separating plate 1230 which can be utilized to peel, or separate, buttress material 1234 from carrier 1202. In at least one embodiment, separating plate 1230 can include edge 1258 about which carrier 1202 can be redirected such that carrier 1202 can be pulled proximally by strip collector 1228 as described above.

In various circumstances, slack may be developed within carrier strip 1202 after it has been separated from buttress material 1236. In at least one embodiment, dispenser 1200 can include one or more tensioning devices to reduce such slack within carrier strip 1202. In various embodiments, similar to the above, dispenser 1200 can further include pin 1218 which can be rotatably supported within aperture 1251 in first housing portion 1210 and an aperture (not illustrated) in second housing portion 1212 wherein pin 1218 can be configured to rotatably support pressure roller 1222. In various embodiments, referring particularly to FIGS. 56 and 57, dispenser 1200 can further include second drive roller 1253 which can be configured to cooperate with pressure roller 1222. In at least one embodiment, second drive roller 1253 can be operably engaged with thumb roller 1236 such that the rotation of thumb roller 1234 can be transmitted to drive roller 1253. In various embodiments, dispenser 1200 can further include a gear train comprising spur gear 1244 mounted to at least one of thumb roller 1234 and pin 1235, intermediate gear 1246 rotatably supported by pin 1247, and driven gear 1252 which can be operably engaged with drive roller 1253. In at least one such embodiment, carrier strip 1202 can be positioned intermediate drive roller 1253 and pressure roller 1222 such that, when driver roller 1253 is rotated by thumb roller 1234, driver roller 1253 can drive carrier strip 1202 proximally. In at least one embodiment, pressure roller 1222 and/or driver roller 1253 can be comprised of an at least partially compressible material such that pressure roller 1222 can hold carrier strip 1202 against driver roller 1253.

As described above, referring to FIGS. 54-57, applicator 1200 can include housing 1201 comprising first portion 1210 and second portion 1212, wherein the first and second portions can be configured to be attached to one another. In at least one embodiment, the first and second portions of housing 1201 can be screwed, snapped, and/or otherwise engaged with each other. In various embodiments, the first and second housing portions can be releasably engaged with each other such that the first and second housing portions can be separated in order to remove and replace an expended spool of buttress material. In at least one embodiment, the housing can include ergonomic features such that the housing can be easily gripped by a surgeon.

In other various embodiments, referring to FIGS. 58-61, dispenser, or applicator, 1266 can include spool 1267 from which buttress material 1236 can be dispensed and, in addition, collection spool 1270 which can be configured to collect carrier strip 1202 after it has been separated from buttress material 1236. Similar to the above, buttress material 1236 can be dispensed from applicator 1266 via the engagement between buttress material 1236, thumb roller 1234, and/or drive roller 1232. In at least one embodiment, collection spool 1270 can also be operatively engaged with thumb roller 1234 such that the rotation of thumb roller 1234 can rotate spool 1270 and collect carrier strip 1202 thereabout. In various embodiments, applicator 1266 can include a gear train comprising spur gear 1244 mounted to at least one of thumb roller 1234 and pin 1235, intermediate gear 1246 rotatably supported by pin 1247, and driven gear 1272 which can be mounted to at least one of spool 1270 and pin 1271. In at least one such embodiment, as a result, the rotation of thumb roller 1234 can drive collection spool 1270, directly apply a force to carrier strip 1202, and collect carrier strip 1202 around spool 1270.

Figure 61:
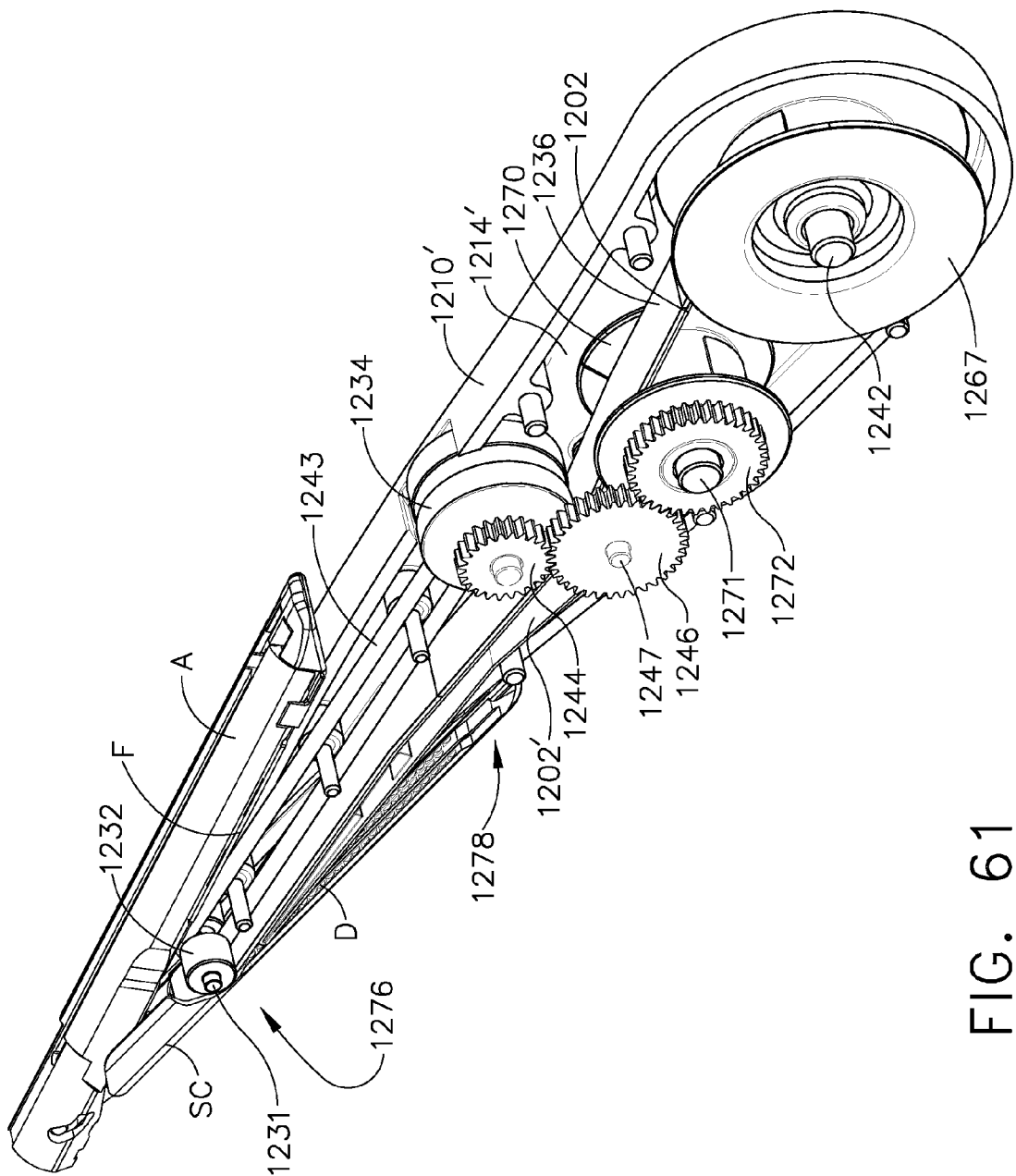
FIG. 61 is a perspective view of the buttress material applicator of FIG. 58 with some components removed.

In various embodiments, referring to FIGS. 57 and 61, buttress material applicators 1200 and/or 1266 can be used to apply a piece of buttress material to a deck "D" of a staple cartridge "SC" and/or a face "F" of an anvil "A". In at least one embodiment, as illustrated in FIG. 61, a surgeon can first place applicator 1266, for example, against first end 1276 of deck D. Thereafter, the surgeon can pull the applicator towards second end 1278 of deck D while rotating thumb roller 1234 to dispense buttress material 1236. As discussed above, buttress material 1236 can be separated into pieces and, in at least one embodiment, the length of the pieces can be such that the pieces of buttress material properly fit on the staple cartridge deck and/or the anvil face. In other various embodiments, the piece of buttress material can be comprised of one continuous strip and the applicator can include a cutting member (not illustrated) which can be configured to cut the buttress material to any suitable length. In various embodiments, the pieces of buttress material can include an adhesive thereon, or which can be applied thereto, which can be configured to releasably retain the buttress material to one of the deck and/or the face.

In various embodiments, a piece of buttress material can be manufactured utilizing an injection molding process. In at least one embodiment, an injection mold (not illustrated) can include one or more mold cavities defined therein which can be configured to receive a molten material, for example. In various embodiments, the molten material can include a plastic and/or any other suitable buttress material. In various embodiments, the mold can further include at least one sprue cavity and/or runner which can place the mold cavities in fluid communication with an injection molding machine. In at least one embodiment, the mold can include first and second portions which can be separated after the molten material has sufficiently solidified or hardened within the mold cavities.

Figure 62:
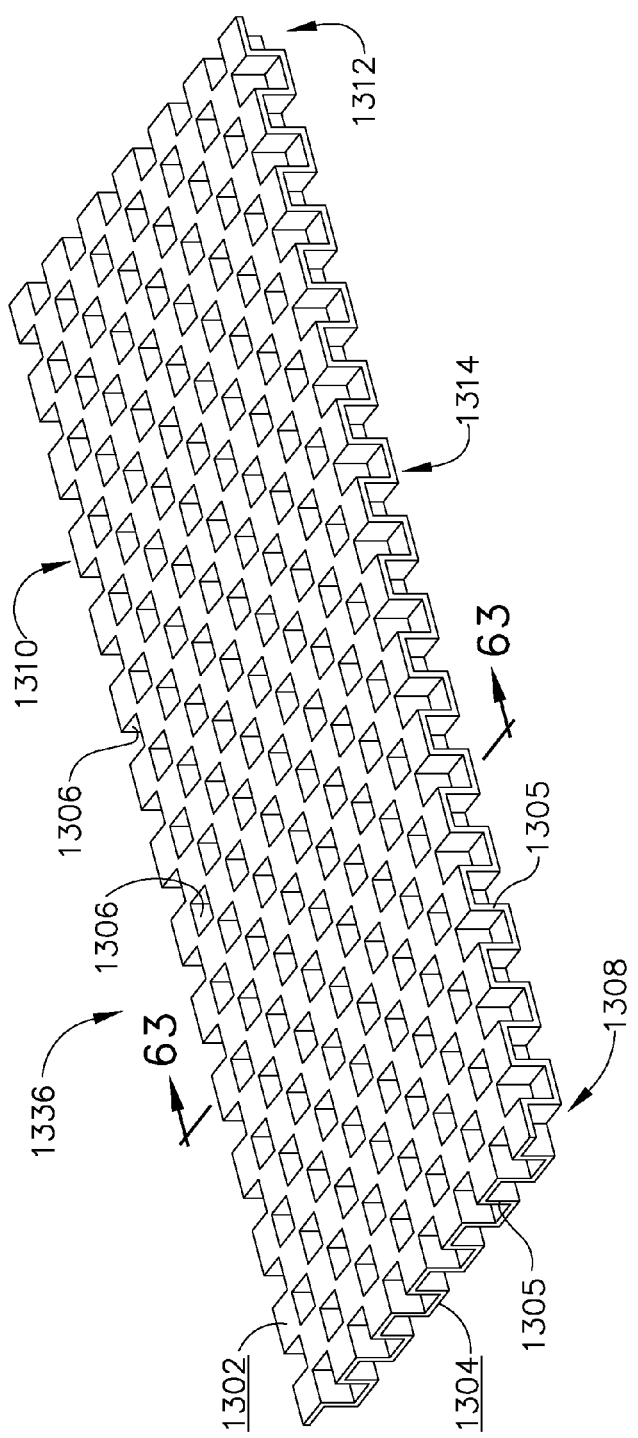
FIG. 62 is a perspective view of a piece of buttress material in accordance with one non-limiting embodiment of the present invention.
Figure 63:
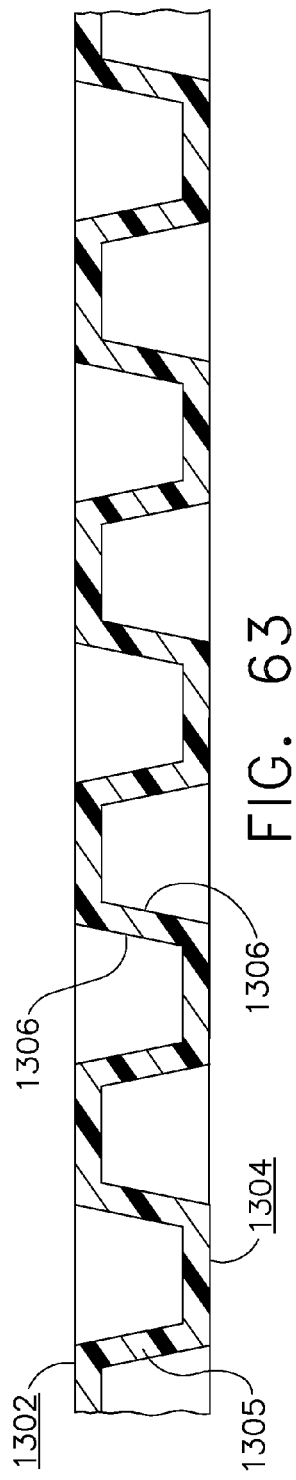
FIG. 63 is a cross-sectional view of the piece of buttress material of FIG. 62 taken along line 63-63 in FIG. 62.

In various embodiments, referring to FIGS. 62 and 63, piece of buttress material 1336 can include first surface 1302 and second surface 1304, wherein the first and second surfaces can each include plurality of apertures, or recesses, 1306 formed therein. In at least one embodiment, recesses 1306 can be formed by molten material within a mold during an injection molding process. More particularly, the mold can include one or more cavities having a plurality of projections which can be configured such that the molten material will flow around the projections and, when the piece of buttress material 1336 has solidified and is removed from the mold, recesses 1306 may be present within buttress material 1336 where the projections were previously situated.

In various embodiments, buttress material 1336 can further include a plurality of walls, such as walls 1305, for example, formed intermediate first and second surfaces 1302 and 1304 wherein walls 1305 can define recesses 1306. In at least one embodiment, walls 1305 can be perpendicular and/or transverse to the first and second surfaces such that walls 1305 can be structured and arranged to form a pattern or grid of recesses 1306 within buttress material 1336. In various embodiments, buttress material 1336 can be resilient such that first surface 1302 and/or second surface 1304 can be compressed towards one another. In at least one such embodiment, buttress material 1336 can be configured such that it can be compressed or press-fit between two or more retention members of an end-effector as described above. In various embodiments, a piece of buttress material can be compressed when applied to an end-effector of a surgical instrument and can then expand when it is released from the end-effector. In at least one embodiment, buttress material 1336 can be configured to be compressed such that first surface 1310 can be moved toward surface 1312. In any event, walls 1305 can be configured such that they can deflect or collapse and allow portions of buttress material 1336 to resiliently move toward one another.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An end-effector assembly for use with a surgical stapler, the end-effector assembly comprising:
   a staple cartridge including a deck, wherein said deck comprises a surface, a plurality of apertures defined by the surface, and a longitudinal slot substantially bifurcating the surface;
   a blade positioned to traverse distally within the longitudinal slot;
   an anvil including a face;
   a first piece of buttress material including a first opening, wherein said first piece of buttress material is configured to be positioned intermediate said staple cartridge and said anvil on a first side of said longitudinal slot such that said first opening is substantially aligned with a first aperture selected from said apertures;
   a second piece of buttress material including a second opening, wherein said second piece of buttress material is configured to be positioned intermediate said staple cartridge and said anvil on a second side of said longitudinal slot opposite said first piece of buttress material such that said second opening is substantially aligned with a second aperture selected from said apertures; and
   first and second connection members, wherein the first connection member is configured to be positioned within said first opening and said first aperture to releasably retain said first piece of buttress material to said staple cartridge, wherein the second connection member is configured to be positioned within said second opening and said second aperture to releasably retain said second piece of buttress material to said staple cartridge, and wherein at least said first connection member comprises:
      a head comprising a perimeter that is larger than said first opening of said first buttress material, wherein said head is configured to engage said first buttress material and inhibit said first buttress material from lifting away from said deck surface when said first connection member is engaged with said first aperture; and
      a body removably positioned within said first aperture, wherein said body comprises a perimeter smaller than the perimeter of the head and configured such that a sidewall of said first opening is configured to engage said body perimeter and inhibit said first buttress material from sliding along said deck surface, wherein said body comprises a first end coupled to said head and a second end to be received within said first aperture, wherein said first connection member head includes a portion that is flared away from said body, and wherein said head is detachable from said body when at least a portion of said first buttress material is detached from said staple cartridge.

2. The end-effector assembly of claim 1, further comprising a plurality of connection members, wherein a plurality of apertures are defined in said face, and wherein a third piece of buttress material includes a plurality of openings which are configured to be substantially aligned with said plurality of apertures such that said plurality of connection members can be inserted into said plurality of apertures and said plurality of openings to releasably retain said piece of buttress material to said anvil.

3. The end-effector assembly of claim 1, wherein said first connection member is configured to be disengaged from said first opening when said first piece of buttress material is detached from said staple cartridge.

4. The end-effector assembly of claim 1, wherein said first connection member is comprised of a bioabsorbable material.

5. The end-effector assembly of claim 1, wherein said first connection member is configured to remain within said first opening after said first piece of buttress material is detached from said staple cartridge.

6. The end-effector assembly of claim 1, wherein said first connection member is configured to be press-fit within said first aperture.

7. The end-effector assembly of claim 1, wherein said first connection member body includes threads configured to engage said first aperture.

8. The end-effector assembly of claim 7, wherein said threads include self-tapping threads.

9. The end-effector assembly of claim 1, wherein said first connection member body does not include threads.

10. An end-effector assembly for use with a surgical stapler, the end-effector assembly comprising:
- a staple cartridge including a deck, wherein said deck comprises a surface, a plurality of apertures defined by the surface, and a longitudinal slot substantially bifurcating the surface;
- a blade positioned to traverse distally within the longitudinal slot;
- an anvil;
- a first piece of buttress material including a first opening, wherein said first piece of buttress material is configured to be positioned intermediate said staple cartridge and said anvil on a first side of said longitudinal slot such that said first opening is substantially aligned with a first aperture selected from said apertures;
- a second piece of buttress material including a second opening, wherein said second piece of buttress material is configured to be positioned intermediate said staple cartridge and said anvil on a second side of said longitudinal slot opposite said first piece of buttress material such that said second opening is substantially aligned with a second aperture selected from said apertures; and
- a plurality of fasteners configured to releasably retain said first and second pieces of buttress material to said staple cartridge, wherein at least one of said fasteners comprises:
  - a body configured to engage said staple cartridge, wherein said body is configured to limit relative movement between said first buttress material and said staple cartridge in a first direction which is parallel to said deck surface; and
  - a head flared outwardly with respect to said body, wherein said head is configured to limit relative movement between said first buttress material and said staple cartridge in a second direction which is perpendicular to said deck surface, wherein said body comprises a perimeter smaller than the perimeter of the head and configured such that a sidewall of said first opening is configured to engage said body perimeter and inhibit said buttress material from sliding along said deck surface, wherein said body comprises a first end coupled to said head and a second end to be received within said first aperture, and wherein said fastener head includes a portion that is flared away from said body, and wherein said head is detachable from said body when at least a portion of said first buttress material is detached from said staple cartridge.

11. The end-effector assembly of claim 10, wherein said staple cartridge includes a plurality of apertures, wherein said fasteners are configured to be releasably press-fit within said apertures to retain said first and second pieces of buttress material to said staple cartridge.

12. The end-effector assembly of claim 10, further comprising:
- a third piece of buttress material configured to be positioned intermediate said staple cartridge and said anvil; and
- a plurality of fasteners configured to releasably retain said piece of buttress material to said anvil.

13. The end-effector assembly of claim 10, wherein said fasteners are bioabsorbable.

14. The end-effector assembly of claim 10, wherein said fastener body includes threads configured to engage said first aperture.

15. The end-effector assembly of claim 14, wherein said threads include self-tapping threads.

* * * * *

UNITED STATES PATENT AND TRADEMARK OFFICE
CERTIFICATE OF CORRECTION

| | | |
|---|---|---|
| PATENT NO. | : 8,371,491 B2 | Page 1 of 1 |
| APPLICATION NO. | : 12/032002 | |
| DATED | : February 12, 2013 | |
| INVENTOR(S) | : Huitema et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 323 days.

Signed and Sealed this
Eleventh Day of November, 2014

Michelle K. Lee
*Deputy Director of the United States Patent and Trademark Office*